US009776146B2

(12) United States Patent
Schultz et al.

(10) Patent No.: US 9,776,146 B2
(45) Date of Patent: *Oct. 3, 2017

(54) SYSTEM AND METHODS FOR MAKING AND PROCESSING EMULSIONS

(71) Applicant: LIFE TECHNOLOGIES CORPORATION, Carlsbad, CA (US)

(72) Inventors: Jonathan Schultz, Guilford, CT (US); John Nobile, Guilford, CT (US); Brian Reed, Woodbridge, CT (US); Prasanna Krishnan Thwar, Los Altos, CA (US); Todd Roswech, Guilford, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,642

(22) Filed: Apr. 27, 2015

(65) Prior Publication Data

US 2015/0224457 A1 Aug. 13, 2015

Related U.S. Application Data

(63) Continuation of application No. 13/442,547, filed on Apr. 9, 2012, now Pat. No. 9,017,993.

(Continued)

(51) Int. Cl.

| | |
|---|---|
| ***B01F 5/06*** | (2006.01) |
| ***C12M 1/34*** | (2006.01) |

(Continued)

(52) U.S. Cl.

CPC .......... *B01F 5/0602* (2013.01); *B01F 3/0807* (2013.01); *B01F 5/0485* (2013.01);

(Continued)

(58) Field of Classification Search

CPC .......... B01F 13/0059; B01F 2215/0037; B01F 3/0807; B01F 5/0485; B01F 5/0602; B01L 3/502784; B04B 5/0414; B04B 7/02

See application file for complete search history.

(56) References Cited

U.S. PATENT DOCUMENTS

| | | | |
|---|---|---|---|
| 3,695,509 | A | 10/1972 | Javet |
| 3,963,440 | A | 6/1976 | Stein et al. |

(Continued)

FOREIGN PATENT DOCUMENTS

| | | |
|---|---|---|
| JP | 2005279458 | 10/2005 |
| WO | 2005073410 | 8/2005 |
| WO | 2008144288 | 11/2008 |

OTHER PUBLICATIONS

Diehl, Frank et al., "Detection and quantification of mutations in the plasma of patients with colorectal tumors", *PNAS*, vol. 102, No. 45, 2005, 16368-16373.

(Continued)

*Primary Examiner* — Michael Hobbs

(57) ABSTRACT

An automated on-touch template bead preparation system is provided and includes a membrane-based emulsion generation subsystems, an emulsion PCR (ePCR) thermocycling plate and subsystem, and a continuous centrifugation emulsion breaking and templated bead collection subsystem. The emulsion generation subsystem provides uniformity in the preparation of an inverse emulsion and may be used to create large or small volume inverse emulsions rapidly and reproducibly. An emulsion-generating device is provided that can supply a continuous stream of an inverse emulsion to a thermocycling subsystem, in automated fashion. The ePCR subsystem can continuously thermocycle an inverse emulsion passed therethrough and includes static temperature zones and a consumable thermocycling plate. The continu- (Continued)

ous centrifugation subsystem can continuously break a thermally cycled inverse emulsion and collect template beads formed in the aqueous microreactor droplets of the inverse emulsion.

20 Claims, 43 Drawing Sheets

Related U.S. Application Data

(60) Provisional application No. 61/583,079, filed on Jan. 4, 2012, provisional application No. 61/489,928, filed on May 25, 2011, provisional application No. 61/472,869, filed on Apr. 7, 2011.

(51) Int. Cl.

| | |
|---|---|
| ***C12M 3/00*** | (2006.01) |
| ***B01F 3/08*** | (2006.01) |
| ***B01F 5/04*** | (2006.01) |
| ***B01F 13/00*** | (2006.01) |
| ***B04B 5/04*** | (2006.01) |
| ***B04B 7/02*** | (2006.01) |
| *B01L 3/00* | (2006.01) |

(52) U.S. Cl.
CPC ........ *B01F 13/0059* (2013.01); *B04B 5/0414* (2013.01); *B04B 7/02* (2013.01); *B01F 2215/0037* (2013.01); *B01L 3/502784* (2013.01)

(56) References Cited

U.S. PATENT DOCUMENTS

| | | | |
|---|---|---|---|
| 3,990,633 A | 11/1976 | Stahl et al. | |
| 4,070,290 A | 1/1978 | Crosby | |
| 4,822,331 A | 4/1989 | Taylor | |
| 4,938,876 A | 7/1990 | Ohsol et al. | |
| 5,342,280 A | 8/1994 | Niinai et al. | |
| 5,589,073 A | 12/1996 | Chapman et al. | |
| 6,706,519 B1 * | 3/2004 | Kellogg .............. | B01F 13/0064 422/64 |
| 6,879,262 B1 | 4/2005 | Tödteberg et al. | |
| 6,896,849 B2 | 5/2005 | Reed et al. | |
| 9,017,993 B2 * | 4/2015 | Schultz ................. | B01F 3/0807 435/283.1 |
| 9,121,047 B2 | 9/2015 | Schultz et al. | |
| 9,458,485 B2 | 10/2016 | Schultz et al. | |
| 2004/0259237 A1 | 12/2004 | Kellogg et al. | |
| 2005/0079510 A1 | 4/2005 | Berka et al. | |
| 2008/0003571 A1 | 1/2008 | McKernan et al. | |
| 2008/0280331 A1 | 11/2008 | Davies | |
| 2009/0023189 A1 | 1/2009 | Lau et al. | |
| 2010/0173394 A1 * | 7/2010 | Colston, Jr. ........... | B01F 3/0807 435/287.2 |
| 2010/0304982 A1 | 12/2010 | Hinz et al. | |
| 2011/0005932 A1 | 1/2011 | Jovanovich et al. | |
| 2011/0092392 A1 | 4/2011 | Colston, Jr. et al. | |
| 2011/0123985 A1 | 5/2011 | Lau et al. | |

OTHER PUBLICATIONS

Dressman, D et al., "Transforming single DNA molecules into fluorescent magnetic particles for detection and enumeration of genertic vari", *PNAS*, vol. 15, 2003, pp. 8817-8822.
International Preliminary Report on Patentability and Written Opinion of the International Searching Authority for International Application No. PCT/US2012/032786 mailed Oct. 8, 2013, 16 pages.
Partial International Search Report for International Application No. PCT/US2012/032786 mailed Jul. 20, 2012, 13 pages.

* cited by examiner

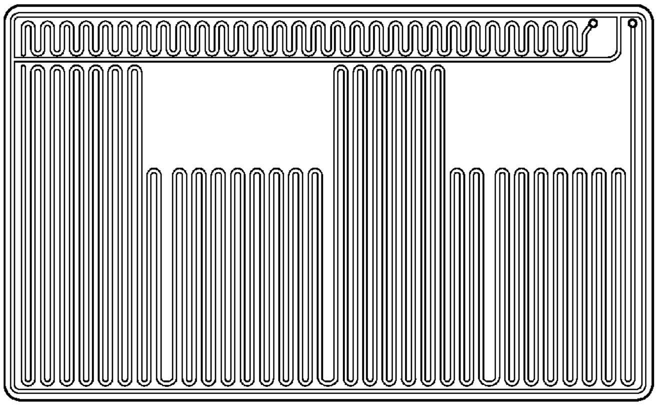
FIG. 24D
FIG. 24E
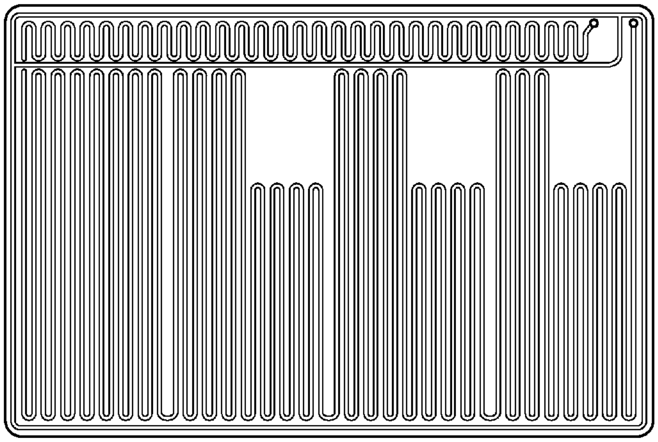
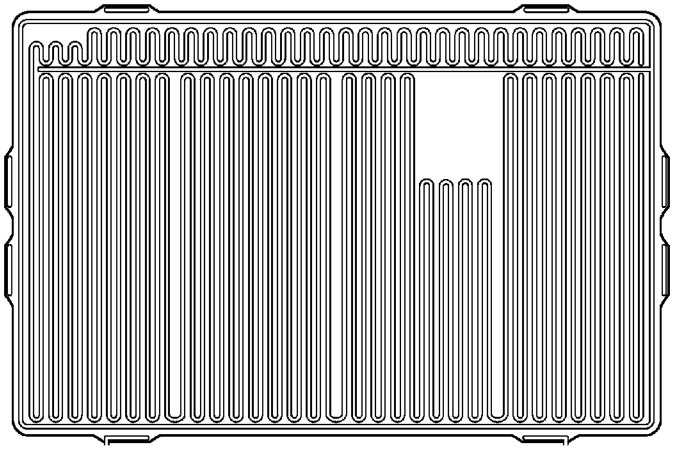
FIG. 24F

SYSTEM AND METHODS FOR MAKING AND PROCESSING EMULSIONS

CROSS-REFERENCE TO RELATED APPLICATIONS

This application is a continuation of U.S. patent application Ser. No. 13/442,547 (U.S. Pat. No. 9,017,993), filed Apr. 9, 2012, which claims benefit of U.S. Provisional Application No. 61/472,869, filed Apr. 7, 2011 and entitled "SYSTEM AND METHODS FOR AUTOMATED SAMPLE LIBRARY PREPARATION," claims benefit of U.S. Provisional Application No. 61/489,928, filed May 25, 2011 and entitled "SYSTEM AND METHODS FOR MAKING AND PROCESSING EMULSIONS," and claims benefit of U.S. Provisional Application No. 61/583,079, filed Jan. 4, 2012 and entitled "SYSTEM AND METHODS FOR MAKING AND PROCESSING EMULSIONS," each of which is incorporated herein by reference in its entirety.

FIELD

The present teachings relate to devices, systems, and methods for preparing and reacting within emulsions, including emulsions useful in biological reaction processes, for example, useful in a polymerase chain reaction (PCR).

INTRODUCTION

A number of biological sample analysis methods rely on sample preparation steps as a precursor to carrying out the analysis methods. For example, a precursor to performing many biological sequencing techniques (e.g., sequencing of nucleic acid) includes amplification of nucleic acid templates in order to obtain a large number of copies (e.g., millions of copies) of the same template.

Polymerase chain reaction is a well understood technique for amplifying nucleic acids which is routinely used to generate sufficiently large DNA populations suitable for downstream analysis. Recently, PCR-based methods have been adapted to amplifying samples contained within emulsions for sequencing applications. In such amplification methods a plurality of biological samples (e.g. nucleic acid samples) may be individually encapsulated in microcapsules of an emulsion and PCR amplification conducted on each of the plurality of encapsulated nucleic acid samples simultaneously. Such microcapsules are often referred to as "microreactors" because the amplification reaction occurs within the microcapsule.

In some cases, the microcapsule can include a template bead, also referred to as a P1 bead or a primer 1 bead and the amplification process may be referred to as bead-based emulsion amplification, for example, as described in US 2008/0003571 A1 to McKernan et al., which is incorporated herein in its entirety by reference. In such a technique, beads along with DNA templates are suspended in an aqueous reaction mixture and then encapsulated in an inverse (water-in-oil) emulsion. The template DNA may be either bound to the bead prior to emulsification or may be included in solution in the amplification reaction mixture. For further details regarding techniques for bead emulsion amplification, reference is made to PCT publication WO 2005/073410 A2, entitled "NUCLEIC ACID AMPLIFICATION WITH CONTINUOUS FLOW EMULSION," which published internationally on Aug. 11, 2005, and is incorporated by reference in its entirety herein.

SUMMARY

According to various embodiments of the present teachings, amplified DNA fragments tethered to a particle or bead can be prepared. Device, systems, apparatuses, and methods are described herein relating to the amplified polynucleic acid tethered particles or beads.

BRIEF DESCRIPTION OF THE DRAWINGS

The accompanying drawings, which are incorporated in and constitute a part of this specification, illustrate exemplary embodiments and together with the description, serve to explain various principles. The skilled artisan will understand that the drawings, described below, are for illustration purposes only. The drawings are not intended to limit the scope of the present teachings in any way.

FIGS. 24A-24F include illustrations of exemplary thermocycling plate designs.

DESCRIPTION

Figure 1:
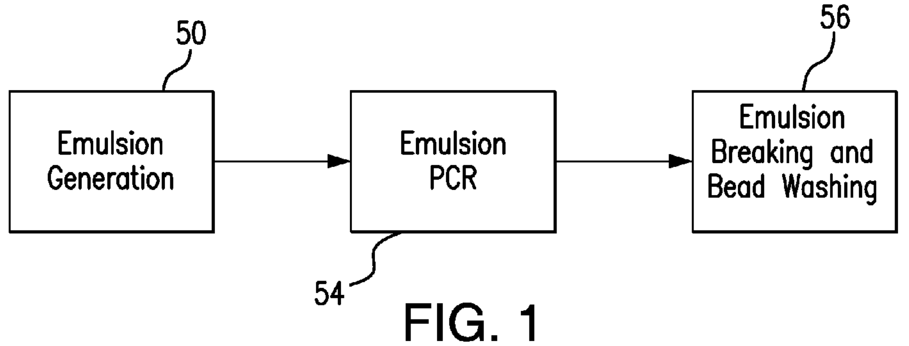
FIG. 1 is a flow diagram showing the method steps involved according to various embodiments of the present teachings.

According to various embodiments of the present teachings, amplified DNA fragments tethered to a particle or bead can be prepared. The method can begin by forming an inverse emulsion comprising a plurality of aqueous droplet microreactors encapsulated and separated from one another by a carrier fluid, for example, an immiscible oil or a fluorinated liquid. Each microreactor, or at least one of them, can contain a template bead, also referred to as a P1 bead or a primer 1 bead, and PCR ingredients. The amplification process may be referred to as a bead-based emulsion amplification, for example, as described in U.S. Patent Application Publication No. US 2008/0003571 A1 to McKernan et al., which is incorporated herein in its entirety by reference. In such a technique, beads along with DNA templates are suspended in an aqueous reaction mixture (a microreactor mixture) and then encapsulated by the immiscible liquid in an inverse (water-in-oil) emulsion. The template DNA may be either bound to the bead prior to emulsification or may be included in solution in the amplification reaction mixture. For further details regarding techniques for bead emulsion amplification, reference is made to PCT publication No. WO 2005/073410 A2, entitled “NUCLEIC ACID AMPLIFICATION WITH CONTINUOUS FLOW EMULSION,” which published internationally on Aug. 11, 2005, and is incorporated by reference in its entirety herein.

According to various embodiments, a method and system are provided for automated sample preparation for sequencing applications. In some embodiments, bead-based emulsion amplification is performed upon formation of an emulsion which encapsulates a template DNA strand, a bead upon which amplicons formed from the template DNA strand are retained, and a reagent mixture for supporting the amplification reaction and providing ingredients therefore. The emulsion can comprise an inverse (water-in-oil) emulsion with the aqueous phase (e.g., the microreactor mixture) including the reagent mixture and the bead, and the carrier fluid including oil or other non-aqueous liquid that is partially or completely immiscible with the aqueous phase.

Particle-based, e.g., bead-based, emulsion amplification can be performed using an emulsion which encapsulates a template DNA strand, a bead upon which amplicons formed from the template DNA strand are retained, and a reagent mixture for supporting the amplification reaction and providing ingredients therefor. The emulsion can comprise an inverse (water-in-oil) emulsion with the aqueous phase (e.g., the microreactor mixture) including the reagent mixture and the bead, and the carrier fluid including oil or other non-aqueous liquid that is partially or completely immiscible with the aqueous phase.

According to various embodiments, an emulsion amplification system is provided. The amplification system can comprise a first sample reaction plate, as described herein, and a heating subassembly, as described herein. The heating subassembly of the amplification system can also comprise a complementary heating block as described herein. The heating subassembly of the amplification system can also comprise a second sample reaction plate. The amplification system can be insulated using any means or mechanism. For example, a gasket can be used for insulating purposes.

In some embodiments, a sample reaction plate is provided in accordance with the present teachings. The sample reaction plate generally may comprise a slab housing and a main fluid passage passageway that passes through the slab housing. The main fluid passageway is disposed in the slab housing and can include an inlet, an outlet, and various fluid passage segments in fluid communication with adjoining fluid passages. The main fluid passageway can comprise a number of fluid passages collectively in fluid communication. Such fluid passages can include an initial fluid passage in fluid communication with the inlet, a transition fluid passage in fluid communication with the initial fluid passage, main fluid passage in fluid communication with the transition fluid passage. The main fluid passage can be in direct fluid communication with the outlet or via an exit fluid passage. The main fluid passage, the initial fluid passage, or both can have a tortuous shape. The main fluid passage, the initial fluid passage, or both can have a plurality of repeating segments or repeats (fluidic paths) between their respective partitions.

A heating subassembly is also provided by the present teachings and can be used in combination with one or more sample reaction plates described herein. The heating subassembly can comprise a first heating block, a first heat control unit, a second heat control unit, and, optionally, a negative load device. The first heating block can comprise a first static heating zone, a heating zone partition, and a second static heating zone separated from the first static heating zone by the heating zone partition. The first heat control unit is operably associable with the first static heating zone. The second heat control unit is operably associable with the second static heating zone. In various embodiments, the first temperature or temperature range, or the second temperature or temperature range, can be a temperature or temperature range sufficient to allow for denaturing of double-stranded nucleic acid, annealing of nucleic acids, or extension of nucleic acids, or any combination thereof. While a single heating block can be employed in the heating subassembly, use of a second, complementary heating block can provide additional temperature control and is particularly advantageous when two sample reaction plates are used. Accordingly, the heating subassembly of the present teachings can comprise a complementary heating block or mated heating blocks.

In some embodiments, sample amplification is provided by thermocycling in accordance with the present teachings. The method can comprise one or more of the following steps, the order of which can be varied, or wherein one or more of the steps can be repeated. A sample fluid can be passed through a sample reaction plate comprising a plurality of regions. A hot start region corresponding to an initial fluid passage of the sample reaction plate can be heated and a denaturation region corresponding to a portion of a main fluid passage proximal a second partition of the sample reaction plate can be heated to a first temperature or temperature range. An annealing/extension region corresponding to a portion of the main fluid passage proximal a third partition of the sample reaction plate can be heated to a second temperature or temperature range. The sample fluid passed through the fluid passageway can comprise a water-in-oil emulsion comprising a plurality of aqueous polymerase chain reaction (PCR) reaction droplets.

In accordance to various embodiments of the present teachings, a centrifuge system is provided that is suitable for integration into an emulsion amplifying system or equivalent device. The centrifuge can comprise a centrifuge housing, a motor comprising a rotor axle mounted in the housing motor aperture, and a rotor mounted on the rotor axle.

A fluid collection tube is provided that can comprise a main tube body and a tube extension. The main tube body can comprise a main body sidewall surrounding a tube interior with a tube opening at a first end, and a second end distal to the first end providing a sealed base. The tube extension can comprise a tube extension sidewall defining a fluid exit channel in fluid communication with the tube interior through a tube channel inlet proximal to the tube opening and extending to a tube channel outlet distal to the tube opening.

A fluid distribution device, also referred to herein as a "slinger," is provided by the present teachings. The slinger can comprise sidewalls defining a central channel comprising a first end, a central zone, and a second end along a longitudinal axis. Sidewall lateral extensions, also referred to as "wings" herein, can be provided extending away from the sidewalls on either side of the central channel. The wings are useful in mating with and ensuring a secure connection with a fluid distribution device receptacle of a centrifuge rotor. Rather than use an insertable/detachable slinger, a slinger can be employed that is permanently or integrally associated with the rotor housing.

A centrifuge rotor is provided by the present teachings, which is particularly suitable for separating water-in-oil emulsions and removing the oil phase of such an emulsion. The centrifuge rotor can comprise a rotor housing having a bisecting rotor axis perpendicular to a central rotor axis, a rotor basin formed by the rotor housing, a rotor basin floor, and a rotor basin sidewall lining the rotor housing basin and extending up toward a rotor top rim having an inner perimeter and an outer perimeter. The rotor can further comprise at least one collection tube receptacle comprising an opening formed in the basin sidewall, and at least one tube extension receptacle having a grove formed in the rotor top rim and extending from the inner perimeter to the outer perimeter. The rotor can also comprise at least one liquid distribution device (slinger) receptacle extending from the rotor basin floor and having a distribution device receptacle longitudinal axis.

A method of recovering a polymerase chain reaction (PCR) product from a water-in-oil emulsion is provided in accordance with the present teachings. The method can be performed using the centrifuge or centrifuge components of the present teachings.

The method can comprise one or more of the following steps. At least one collection tube can be filled with an aqueous solution and inserted into a tube receptacle of a centrifuge rotor. At least one fluid distribution device (slinger) can also be inserted into a fluid distribution device receptacle of the centrifuge rotor. Sample fluid, which can comprise a PCR product in a water-in-oil emulsion, can be fed into the fluid distribution device. The centrifuge rotor is spun to deliver the sample fluid to the at least one collection tube, and the emulsion is partly or completely broken in the at least one collection tube. The centrifuge rotor motor can also be spun to remove an oil phase from the collection tube. The method can further comprise recovering PCR product from the at least one collection tube.

As shown in FIG. 1, automated bead sample preparation method is provided that can comprise generating an emulsion in a first step 50, conducting emulsion PCR in a second step 54, and conducting an emulsion breaking and bead washing third step 58. According to various embodiments, an emulsion can be generated that comprises droplets of an aqueous phase, herein called microreactors, in which clonal amplification can take place. Microreactors containing a single template bead and a single template, called monoclonal microreactors, are desired and can be formed according to the present teachings. Some microreactors, however, can be polyclonal such that they contain multiple templates, non-clonal such that they contain no template, or multi-bead-containing. Some microreactors can exhibit a combination of these undesirable features.

In some embodiments, microreactors can be formed by mixing together a plurality of template beads, a library of templates from a sample, DNA polymerase, a buffer, dNTPs, one or more surfactants, and a pair of primers, in an aqueous phase solution to form an aqueous phase. The aqueous phase can then be contacted with an oil phase and emulsified to form an inverse emulsion comprising the microreactors in the oil phase. Although reference is made herein to an oil phase, it is to be understood that other PCR-compatible immiscible liquids can be used for the continuous phase of the inverse emulsion provided the liquid is immiscible with the aqueous phase. Fluorinated compounds, fluorinated liquids, minerals oils, silicone oils, and the like, can be used in some embodiments.

In some embodiments, microreactors can be formed by including at least one additive. For example, an additive includes a polymer compound comprising a homo-polymeric or hetero-polymeric compound. In some embodiments, a polymer compound includes amphiphilic and hydrophilic compounds. In some embodiments, a polymer compound includes synthetic and naturally-occurring compounds. In some embodiments, a polymer compound can be soluble in water, alcohol, ether, ketone or ester. In some embodiments, a polymer compound comprises a chain of two or more tetrahydrapyrrole monomers. In some embodiments, a tetrahydrapyrrole monomer comprises a five-membered heterocyclic ring. In some embodiments, in a chain of tetrahydropyrrole rings, one or more tetrahydropyrrole rings comprise a nitrogen atom reacted with a carbonyl or carboxylic acid compound. In some embodiments, a polymer compound includes but is not limited to polyvinylpyrrolidone (e.g., povidone or crospovidone), poly(4-vinylphenol), and vinylpyrrolidone/vinyl acetate copolymer (e.g., copovidone). In some embodiments, a polymer compound comprises two or more monomers of N-vinyl-pyrrolidone, including modified polymers thereof. Modified polymers of poly(N-vinyl-pyrrolidone) comprise monofunctionalized (e.g., hydroxyl or carboxy end group) polymers, side-chain conjugates (e.g., poly- and multifunctional side chains), and grafted copolymers. In some embodiments, polyvinylpyrrolidone includes a range of molecular weight polymers including 2500-750,000 g/mol. In some embodiments, polyvinylpyrrolidone includes various molecular weight polymers including average molecular weights of about 5 kD-55 kD, for example average molecular weights of about 10 kD, 29 kD, 40 kD, and 55 kD. In some embodiments, polyvinylpyrrolidone can be commercially-available, including: Kollidon, Luviskol, Albigen A, Devergan (BASF), PVP (General Analine and Film, Corp.), PVP 10 kD (Sigma-Aldrich, #PVP10-100G), Plasdone (General Analine and Film, Corp.), Collacral, Luviskol VA, and PVP/VA (copolymers of vinyl acetate, General Analine and Film, Corp.).

In some embodiments, a library of nucleic acid templates can be amplified in a microreactor. In some embodiments, the yield or reaction rate of a nucleic acid amplification reaction can be improved by addition of a polymer compound. For example, a polymer compound can serve as a molecular crowding agent in a nucleic acid amplification reaction, or a polymer compound can bind or neutralize polar molecules or polyphenolic compounds that may interfere with a nucleic acid amplification reaction. In some embodiments, a polymer compound can bind or neutralize a polyether compound including oligomers or polymers of ethylene oxide (e.g., polyethylene glycol). In some embodiments, a polyvinylpyrrolidone can bind a polyethylene glycol. In some embodiments, a polymer compound can bind polyethylene glycol having a molecular weight of less than about 20,000 g/mol, or more than about 20,000 g/mol.

In another example, a polymer compound can serve as a surfactant. A surfactant can stabilize an oil and aqueous mixture. A surfactant can reduce surface tension at an interface between oil and aqueous phases. A surfactant can reduce loss of enzymes (e.g., polymerase) to an oil-water interface which can make the enzymes available to catalyze a nucleic acid amplification reaction.

In some embodiments, the yield of nucleic acids deposited onto a surface or into a well can be improved by inclusion of a polymer compound. For example, one or more beads that are attached with a nucleic acid library can be deposited onto a surface or well in the presence of a polymer compound. In some embodiments, a polymer compound can inhibit electro-osmotic flow to improve deposition of beads (e.g., attached with nucleic acids) onto a surface or well. A bead can be attached with an amplified (e.g., clonally amplified nucleic acid library). In some embodiments, a nucleic acid library bound to a bead can be deposited onto a surface or into a well in the presence of an aqueous solution comprising a polymer compound (e.g., a polyvinylpyrrolidone or derivative thereof).

In another example, a surface or well can be coated with a polymer compound. In some embodiments, a polymer compound can act as a blocking agent (e.g., a passivating agent) to reduce adherence of a surface to nucleic acids, beads or nucleic acid amplification reagents (e.g., polymerase). A surface can include a surface of any component of a membrane-based emulsion-generating system (e.g., emulsion-generating membrane, gasket, wall of container), emulsion thermocycling subsystem (e.g., thermocycling plate, gasket, fluidics passageway) or a system for recovering a polymerase chain reaction (e.g., fluidic distribution device, collection tube). For example, any surface of a thermocycling plate (e.g., a fluid passageway) can be coated with a polymer compound to reduce adherence between the surface and beads, nucleic acids, or reagents in a nucleic acid amplification reaction.

In some embodiments, microreactors can include at least one polymer compound (e.g., polyvinylpyrrolidone) at about 0.1-8%, or about 1-2%, or about 2-3%, or about 3-4%, or about 4-5%, or about 5-6%, or about 6-7%, or about 7-8%.

In some embodiments, a microreactor comprises a plurality of template beads, a library of templates from a sample, DNA polymerase, a buffer, dNTPs, one or more surfactants, a pair of primers, and about 0.5-4% polymer compound, in an aqueous phase solution to form an aqueous phase.

In some embodiments, a microreactor comprises a plurality of template beads, a library of templates from a sample, DNA polymerase, a buffer, dNTPs, one or more surfactants, a pair of primers, and about 0.5-4% polyvinylpyrrolidone (e.g., 2% final concentration of PVP 10 kD or 40 kD), in an aqueous phase solution to form an aqueous phase.

The aqueous phase can be contacted with an oil phase and emulsified to form an inverse emulsion comprising microreactors in an oil phase.

Once the inverse emulsion has been formed, DNA can be amplified within the individual microreactors by conducting emulsion polymerase chain reaction (ePCR) as shown in step 54 of FIG. 1. In some embodiments, the emulsion PCR step, step 54, can comprise thermally cycling the emulsion to cause respective polymerase chain reactions to occur within the microreactors. The polymerase chain reactions can cause the formation of a plurality of templated beads each comprising a plurality of amplicons, attached thereto, of the respective template originally contained in the respective microreactor. According to some embodiments, the polymerase chain reactions can produce, for example, more than 1,000 copies, more than 10,000 copies, more than 30,000 copies, or more than 50,000 copies of the template attached to each respective template bead.

Emulsion Generation Subsystem

To begin the ePCR, each template bead can comprise a respective primer, for example, a P1 primer, attached to a bead. In non-clonal microreactors, the template bead cannot amplify. Although beads are referred to often herein, it is to be understood that other template or target supports can be used, for example, particles, granules, rods, spheres, shells, combinations thereof, and the like, which are collectively referred to herein as "beads." Furthermore, although the microreactors are described herein as containing components for PCR, it is to be understood that the microreactors can contain components for reactions other than PCR, for example, components for an isothermal reaction, components for a different type of amplification reaction, components for an enzymatic reaction, components for a ligation reaction, or the like.

After emulsion PCR (ePCR) is complete, some of the template beads comprise amplicons of the respective template, formed thereon. Such beads with amplicons are herein referred to as templated beads. Templated beads are template beads on which amplification has successfully taken place in the respective microreactors. Some of the template beads do not comprise amplicons of the template formed thereon, and are herein referred to as non-templated beads. Non-templated beads are template beads on which no amplification took place in the respective microreactors. The non-templated beads can also be referred to as non-amplified or non-amplifying beads.

According to various embodiments, the templated beads can be collected by breaking the emulsion to release the templated beads from the microreactors. The collected template beads can then be washed. Breaking the emulsion can comprise a chemical or physical treatment of the emulsion, for example, dispensing the emulsion in a centrifuge and contacting the emulsion with a surfactant or other emulsion breaking agent. According to some embodiments, the emulsion can be contacted with an alcohol, for example, with propanol, butanol, pentanol, or the like.

In some embodiments, each of the templated beads and each of the non-templated beads can have a diameter of from 0.1 μm to 5.0 μm, from 0.25 μm to 2.0 μm, from 0.5 μm to 1.0 μm, from 0.7 μm to 1.2 μm, or from 0.9 μm to 1.1 μm.

According to various embodiments, a wide range of different emulsion volumes, for example, of from approximately 1 mL to 250 mL or more, can be prepared without maintaining a stock of differently sized or configured consumables to accommodate a particular emulsion volume. The emulsion can be made to exhibit a small drop size variation, a slow rate of reversion or phase separation, and an adaptability to a wide variety of volume sizes.

In some embodiments, the present teachings provide devices, methods, and formulations for the preparation of inverse (water-in-oil) emulsions for polymerase chain reactions. In various embodiments, a discrete aqueous phase (droplet) can entrap a particle, for example, a magnetic particle of about 1 μM diameter size and having a template oligonucleotide immobilized on its surface. The discrete aqueous phase droplet can also comprise PCR reagents such as dNTPs, enzymes, co-enzymes, salts, buffers, surfactants, and a template molecule such as a DNA sample. The template molecule can be a sample DNA molecule, for example, a template from a library of templates from a single sample. The carrier fluid can comprise oil with or without added surfactants that have hydrophilic-lipophilic-balance (HLB) values of about 5.0 or less. According to various embodiments of the invention, the surfactants can comprise a mixture of surfactants having various HLB values. Those skilled in the art can appreciate that the surfactant affinity difference (SAD) of the oil phase can be adjusted by using various surfactants with various HLB values such that a stable inverse (water-in-oil) emulsion can be prepared.

In some embodiments, the carrier fluid can comprise a mineral oil such as Petroleum Special, an alkane such as heptadecane, a halogenated alkane such as bromohexadecane, an alkylarene, a halogenated alkyarene, an ether, or an ester having a boiling temperature above 100° C. The carrier fluid can be insoluble or only slightly soluble in water. The ratio between the carrier fluid and the discrete aqueous phase can range, for example, from 1/0.1 v/v to 4/1 v/v, from 0.5/1 to 3/1, from 0.8/1 to 1/1, or as desired.

Figure 2:
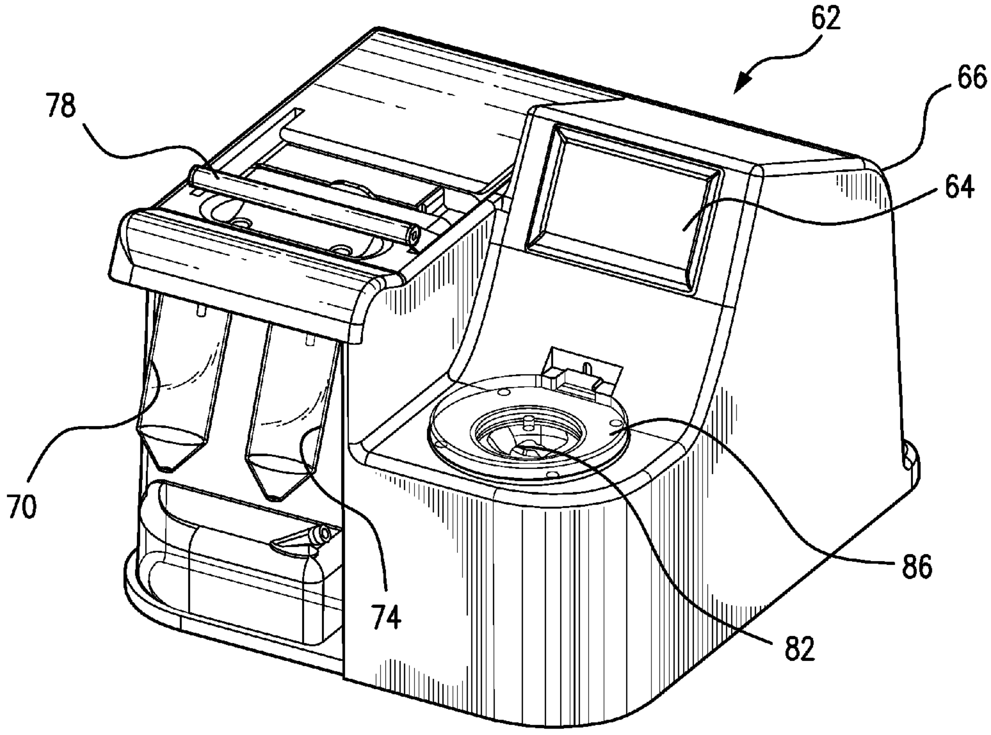
FIG. 2 is a perspective view of an automated sample preparation system for conducting automated sample preparation according to various embodiments of the present teachings.

FIG. 2 depicts one embodiment of a machine or an automated sample preparation system 62 for conducting automated sample preparation. Automated sample preparation system 62 can comprise a housing 66 for retaining an emulsion-generating station, an emulsion PCR station, and a bead breaking/washing station, disposed within housing 66. The emulsion-generating station can comprise a carrier fluid supply 70 and a microreactor mixture supply 74 for use in the emulsion-generating station of the system. The emulsion PCR station can comprise a lever 78 extending from a surface of housing 66 which can be lifted to an open position whereby a PCR thermocycling plate can be inserted between a first and a second heating block of the emulsion PCR station within housing 66. The bead breaking/washing station can comprise a centrifuge 82 having a centrifuge cover 86 (shown closed), that is hingedly attached to centrifuge 82. A display 64 can be provided to facilitate control or monitoring of automated sample preparation system 62. Display 64 can comprise a touch screen display, an LED display, a LCD screen, or a combination thereof. Display 64 can show the progress of the operation as it is carried out, and can display, for example, the percent completion of an operation while it is being carried out. According to various embodiments, with loading and one touch, a user can make automated sample preparation system 62 run without user interaction for a processing period, for example, for a period of one hour, two hours, three hours, or longer, to produce templated and amplified beads useful for sequencing.

Embodiments of the present teachings provide a filter based emulsion-generating device. The filter can be any device having a plurality of pores of suitable sizes, including but not limited to a membrane and a filter plate. The emulsion-generating device may comprise a first channel plate, a second channel plate, and a first filter disposed between the first channel plate and the second channel plate. The first filter may form a first chamber with the bottom surface of the first channel plate and a second chamber with the top surface of the second channel plate. In the present disclosure, a channel plate can be a gasket. The channel plate can be made of a hard material, including but not limited to glass, metal, and hard plastic. The channel plate can also be made of a soft material, including but not limited to rubber and soft plastic.

The first channel plate may comprise a first fluid port comprising an orifice passing through the first channel plate in a thickness direction. Thus, the first fluid port allows fluid to flow in or out of the first chamber. In an embodiment, the first fluid port is an inlet for introducing an aqueous reaction mixture, e.g., an aqueous ePCR mixture, into the emulsion-generating device.

The first channel plate may also comprise at least one first flow channel disposed on its bottom surface, i.e., facing the first chamber. In some embodiments, the first channel plate may comprise two or more first flow channels disposed on its bottom surface. The first flow channels may or may not contact or cross each other. In an embodiment, at least two of the first flow channels may form a contact or cross each other. In another embodiment, the first flow channels do not form contact or cross each other. In still another embodiment, the first channel plate may comprise a first flow channel that does not connect to the first fluid port.

The second channel plate may comprise a second fluid port comprising an orifice passing through the second channel plate in a thickness direction. Thus, the second fluid port allows fluid to flow in or out of the second chamber. In an embodiment, the second fluid port is an inlet for introducing a carrier fluid, e.g., a water immiscible fluid, into the emulsion-generating device.

The second channel plate may also comprise at least one second flow channel disposed on its top surface, i.e., facing the second chamber. In some embodiments, the second channel plate may comprise two or more second flow channels disposed on its top surface. The second flow channels may or may not contact or cross each other. In an embodiment, at least two of the second flow channels may form a contact or cross each other. In another embodiment, the second flow channels do not form contact or cross each other. In still another embodiment, the second channel plate may comprise a second flow channel that connects to the second fluid port. In still another embodiment, the second channel plate may comprise at least one second flow channel that does not connect to the second fluid port.

In another embodiment, the first or the second channel plate may further comprise a third fluid port comprising an orifice passing the second channel plate in a thickness direction. Thus, the third fluid port allows fluid to flow in or out of the first or the second chamber. In an embodiment, the third fluid port is an outlet for discharging the emulsion containing aqueous microreactor droplets in the carrier fluid from the emulsion-generating device. In an embodiment, the first or the second channel plate may comprise a flow channel that connects to the third fluid port. In another embodiment, the first or the second channel plate may comprise a flow channel that does not connect to the third fluid port.

In still other embodiments, the emulsion-generating device of the present teachings may further comprise one or more second filters disposed between the first channel plate and the first filter, i.e., in the first chamber, or one or more third filters disposed between the second channel plate and the first filter, i.e., in the second chamber.

In the present teachings, the filter, e.g., the first, second or third filter, may comprise a plurality of pores, e.g., a plurality of pores having a size of about 1 to about 50 microns. In an embodiment, the filter, e.g., the first, second or third filter, is a membrane. In a specific embodiment, the filter is a track-etched filter. In the present disclosure, a pore of the filter is also referred to as a through hole.

The emulsion-generating device of the present teachings can further comprise a housing, in which the first channel plate, the second channel plate, and the first filter are mounted. Alternatively, the first channel plate and the second channel plate can also form the housing in which the first filter is mounted.

In some embodiment, the least one first flow channel or the at least one second flow channel is configured to have a low fluid resistance.

In some other embodiment, the at least one first flow channel or the at least one second flow channel may comprise two ends connected by a channel, where the two ends and the channel are disposed in the respective first or second channel plate. In some other embodiment, the at least one first flow channel or the at least one second flow channel is disposed such that fluid passes said first filter a plurality of times.

In yet another embodiment, the first chamber or the second chamber has a depth from said first or second channel plate to said first filter of 500 μm, and the at least one first flow channel or said at least one second flow channel has a depth of less than 500 μm.

The present teachings also provide a system for making emulsion droplets. The system may comprise an emulsion-generating device of the present teachings, a reaction mixture supply in fluid communication with the first chamber by way of said first fluid port; a carrier fluid supply in fluid communication with the second chamber by way of said second fluid port, and an emulsion collection device in fluid communication with the second chamber by way of the third fluid port. The emulsion collection device is any device to which the emulsion is output. For example, the emulsion collection device can be the emulsion PCR device 54. The system can also comprise a device for applying a suitable pressure in the reaction mixture supply or the carrier fluid supply.

The present teachings also provide a method of making emulsion droplets, comprising: flowing an aqueous reaction mixture into the first fluid port of an emulsion-generating device of the teachings, flowing a carrier fluid immiscible with the aqueous reaction mixture into the second fluid port of the emulsion-generating device, and recovering an emulsion fluid comprising droplets of the aqueous reaction mixture in the carrier fluid from the third fluid port. In an embodiment, the method may further comprise adjusting a fluid pressure of the reaction mixture or adjusting a fluid pressure of the carrier fluid such that the droplets of the reaction mixture in the carrier fluid in said step (d) have a predetermined size.

Figure 3:
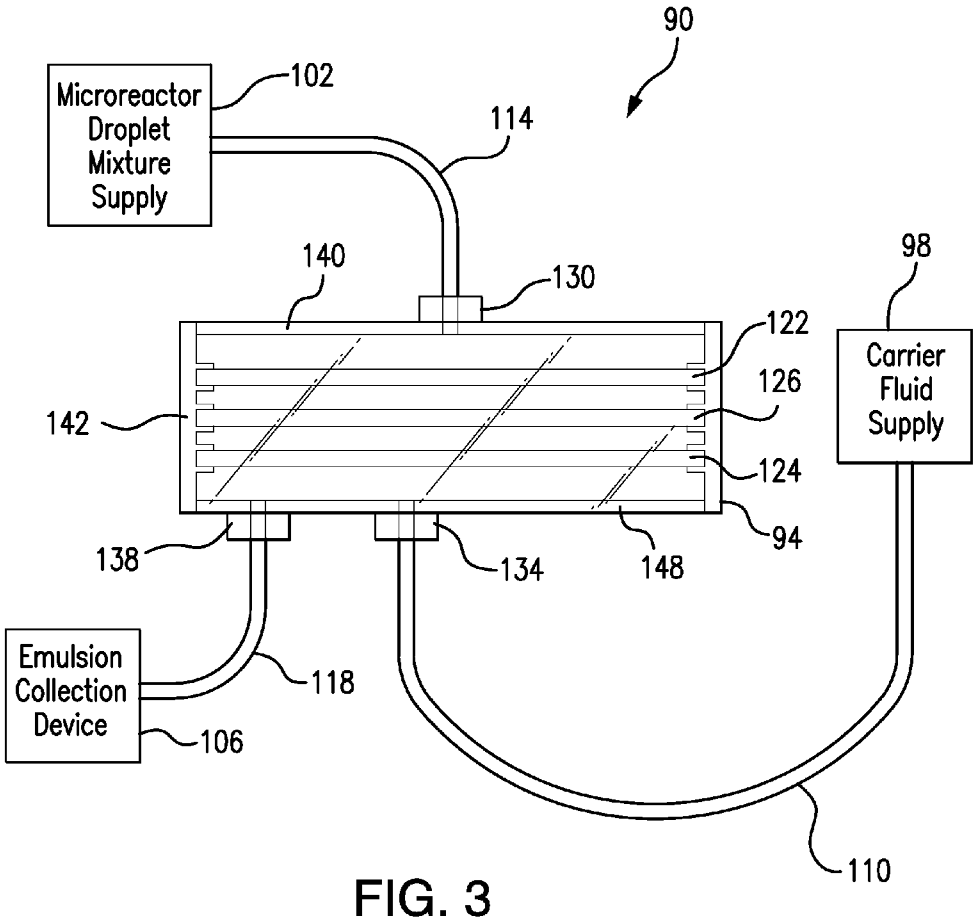
FIG. 3 depicts a schematic diagram and side view of a membrane-based emulsion-generating system for generating emulsion droplets, according to various embodiments of the present teachings.

FIG. 3 depicts a schematic diagram and side view of a membrane-based emulsion-generating system 90 for generating emulsion droplets, according to various embodiments. Emulsion-generating system 90 can comprise an emulsion-generating device 94, a carrier fluid supply 98, a microreactor droplet mixture supply 102, and an emulsion collection device 106. Tubes 110, 114, and 118 can be provided to connect emulsion-generating device 94 to carrier fluid supply 98, microreactor droplet mixture supply 102, and emulsion collection device 106, respectively.

According to various embodiments, emulsion-generating device 94 can comprise a top channel gasket 122, a bottom channel gasket 124, and an emulsion-generating membrane 126 disposed between top channel gasket 122 and bottom channel gasket 124. According to various embodiments, emulsion-generating device 94 can be part of a machine where, with loading and one touch, a user can program the machine to run without further user interaction for a processing period, for example, for one hour, two hours, three hours, or longer, as is desired, to produce templated beads useful for sequencing.

Top channel gasket 122, bottom channel gasket 124 and emulsion-generating membrane 126 can independently comprise a polymer, although other suitable, PCR-compatible materials can be used. Exemplary polymers include poly(ether sulfone), polyester, polyisoprene, polycarbonate, polyvinylpyrrolidone, polyimide, polyamide, polytetrafluoroethylene (PTFE) or other fluorinated polymers or perfluorinated polymers, poly-cyclo-olefin polymers, silicone, and the like. An exemplary silicone includes liquid silicone rubber (LSR). According to some embodiments, top channel gasket 122 and bottom channel gasket 124 can comprise rubber or polyisoprene. According to some embodiments, emulsion-generating membrane 126 can comprise polyvinylpyrrolidone. Emulsion-generating membrane 126 can comprise a hydrophilic material or can be treated to exhibit hydrophilic properties. In other embodiments, emulsion-generating membrane 126 can comprise a hydrophobic material or can exhibit hydrophobic properties. The surface of emulsion-generating membrane 126 can be physically or chemically modified to tailor its hydrophilicity.

According to some embodiments, top channel gasket 122 and bottom channel gasket 124 can, themselves, form end-walls to support emulsion-generating membrane 126 there between. In other embodiments, a container 142 in the form of an outer container, housing, or enclosure, can be provided inside of which emulsion-generating membrane 126, top channel gasket 122, and bottom channel gasket 124, can be disposed. Container 142 can comprise a first portion and a second portion that can be glued, molded, ultrasonically bonded, screwed, or otherwise connected together to form a sealed housing around emulsion-generating membrane 126, top channel gasket 122, and bottom channel gasket 124. Shoulders, ridges, rims, protrusions, catches, or other features can be provided in the inner surfaces of container 142 to hold or maintain emulsion-generating membrane 126, top channel gasket 122, and bottom channel gasket 124 in place. A microreactor input port 130 can be provided in a first portion or top portion 140 of container 142. A carrier fluid input port 134 and an emulsion output port 138 can be provided in a second portion or bottom portion 148 of container 142. Alternatively, an emulsion output port 138 can be defined in top portion 140 of container 142.

It should be understood that carrier fluid supply 98 comprise a pressurized supply of a carrier fluid. Similarly, microreactor droplet mixture supply 102 can comprise a pressurized supply of a microreactor mixture. Pressure to the supplies can be independently provided by a pump, for example, by a syringe pump, by a peristaltic pump, by a pneumatic pump, by an air pump, or the like. According to some embodiments, a control unit can be provided to alternate pressure provided to carrier fluid supply 98 and microreactor droplet mixture supply 102. Emulsion-generating system 90 can comprise a first pressure source to provide an external pressure for moving the microreactor stream through the plurality of through holes. Emulsion-generating system 90 can comprise a second pressure source to provide an external pressure for moving the carrier fluid stream through the plurality of through holes. In some embodiments, the pressure sources can each comprise one or more syringe pumps.

All consumables in the system, including, device 94, container 142 and tubing 110, 114, and 118, can be disposable to minimize cross-contamination. Container 142 can comprise a polymer, such as a polyalkylene material, polyamide, silicone, fluoropolymer, or the like. Tubing 110, 114, and 118, can comprise a polymeric material, such as a silicone material, a polyalkylene material, a polyamide material, a fluoropolymer, or the like.

Figure 4A:
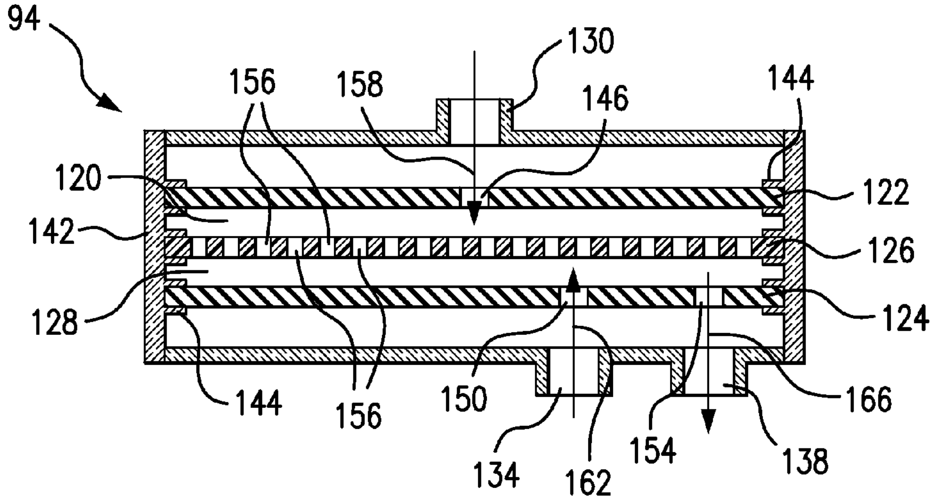
FIG. 4A is a cross-sectional view showing the details of a membrane-based emulsion-generating device according to various embodiments of the present teachings.

As shown in FIG. 4A, according to some embodiments, container 142 can include positioning grooves 144 or rims or shoulders, so that emulsion-generating membrane 126, top channel gasket 122, and bottom channel gasket 124, are properly spaced apart from each other. According to some embodiments, pins or other spacing elements can further be disposed between emulsion-generating membrane 126 and top channel gasket 122, and between emulsion-generating membrane 126 and bottom channel gasket 124, to further support, space, and position emulsion-generating membrane 126. According to some embodiments, emulsion-generating membrane 126 can be rigidly mounted in container 142, so that spacing is maintained between emulsion-generating membrane 126, top channel gasket 122, and bottom channel gasket 124. According to some embodiments, a space between emulsion-generating membrane 126 and top gasket 122 can define a first chamber 120. According to some embodiments, a space between emulsion-generating membrane 126 and bottom gasket 124 can define a second chamber 128.

According to various embodiments, top channel gasket 122 can comprise a first gasket port 146 that can be aligned with microreactor input port 130. Bottom channel gasket 124 can comprise a second gasket port 150 that can be aligned with carrier fluid input port 134 and a third gasket port 154 that can be aligned with emulsion output port 138. According to some embodiments, when emulsion output port 138 is defined in top portion 140 of container 142, third gasket port 154 can be defined in top channel gasket 122 instead of bottom channel gasket 124.

As shown in FIG. 4A, emulsion-generating membrane 126 can comprise a plurality of through holes 156. Each of the plurality of through holes 156 can comprise a straight through pore that connects a first surface of emulsion-generating membrane 126 with a second opposing surface of emulsion-generating membrane 126, and through which a straight line can be drawn that does not touch or intersect the wall of the pore. Each of the plurality of through holes 156 can be circular in cross-section and the plurality of them can be substantially uniform in size. According to some embodiments, each of the plurality of through holes 156 can have a diameter of, for example, from about 1 to about 50 microns, from about 3 to about 15 microns, from about 8 to about 14 microns, or from about 10 to about 12 microns. According to some embodiments, a rim can extend from one or both surfaces of emulsion-generating membrane 126 around each of through holes 156 although no rims are shown in the embodiments depicted. Emulsion-generating membrane 126 can be track-etched to form the plurality of through holes 156. The track-etched through holes can be fabricated using photo-lithography, chemical etching, reactive ion etching (RIE), or the like. According to some embodiments, emulsion-generating membrane 126 can be flexible. According to some embodiments, emulsion-generating membrane 126 can be rigid.

The emulsion generating membrane 126 can alternatively be formed by a laser etch process. For example, the laser etched holes formed in the membrane 126 can have a diameter from about 1 to about 50 microns, from about 3 to about 15 microns, from about 8 to about 14 microns, or from about 10 to about 12 microns. In a particular example, the membrane 126 can include laser etched holes that correspond with the flow regions where channels are formed within the top channel gasket 122 and the bottom channel gasket 124. In particular, the laser etched membranes provide more uniform spacing and less variance in the diameter of through holes within the membrane.

Figure 4B:
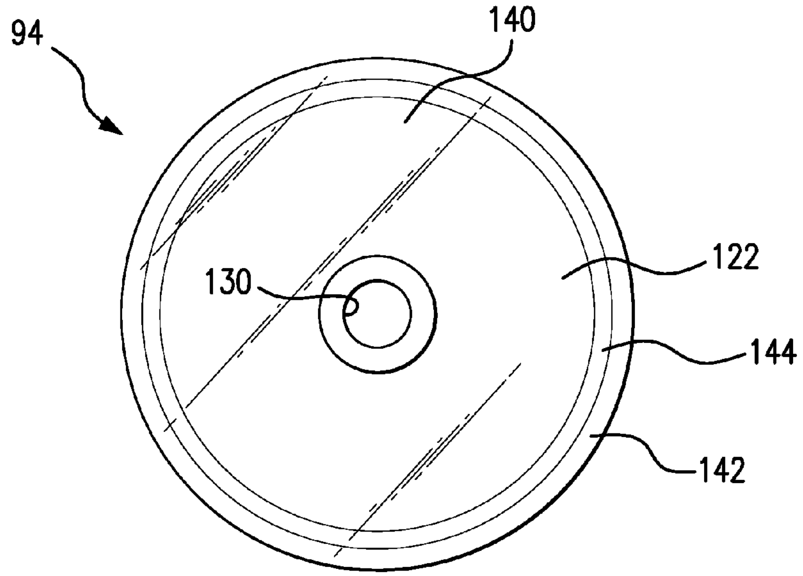
FIG. 4B is a top view of the device shown in FIG. 4A.

FIG. 4B shows a top view of emulsion-generating device 94. Microreactor input port 130 is shown provided in a top portion of container 142. It should be noted that container 142, shown in FIG. 4B, is transparent such that top channel gasket 122 can be seen through it.

Figure 4C:
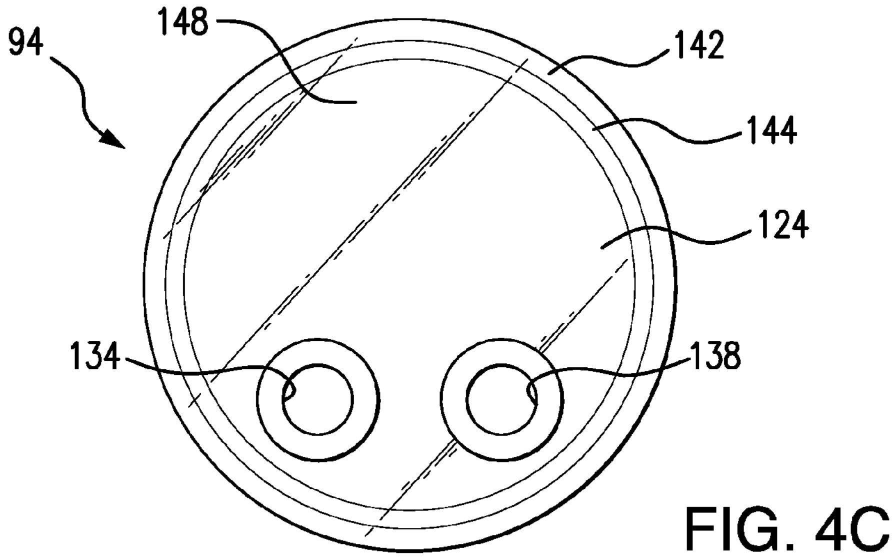
FIG. 4C is a bottom view of the device shown in FIG. 4A.

FIG. 4C shows a bottom view of emulsion-generating device 94. Carrier fluid input port 134 and emulsion output port 138 are shown provided in transparent bottom portion 148 of container 142. It should be noted that container 142, shown in FIG. 4C is transparent such that bottom channel gasket 124 can be seen through it.

Figure 4D:
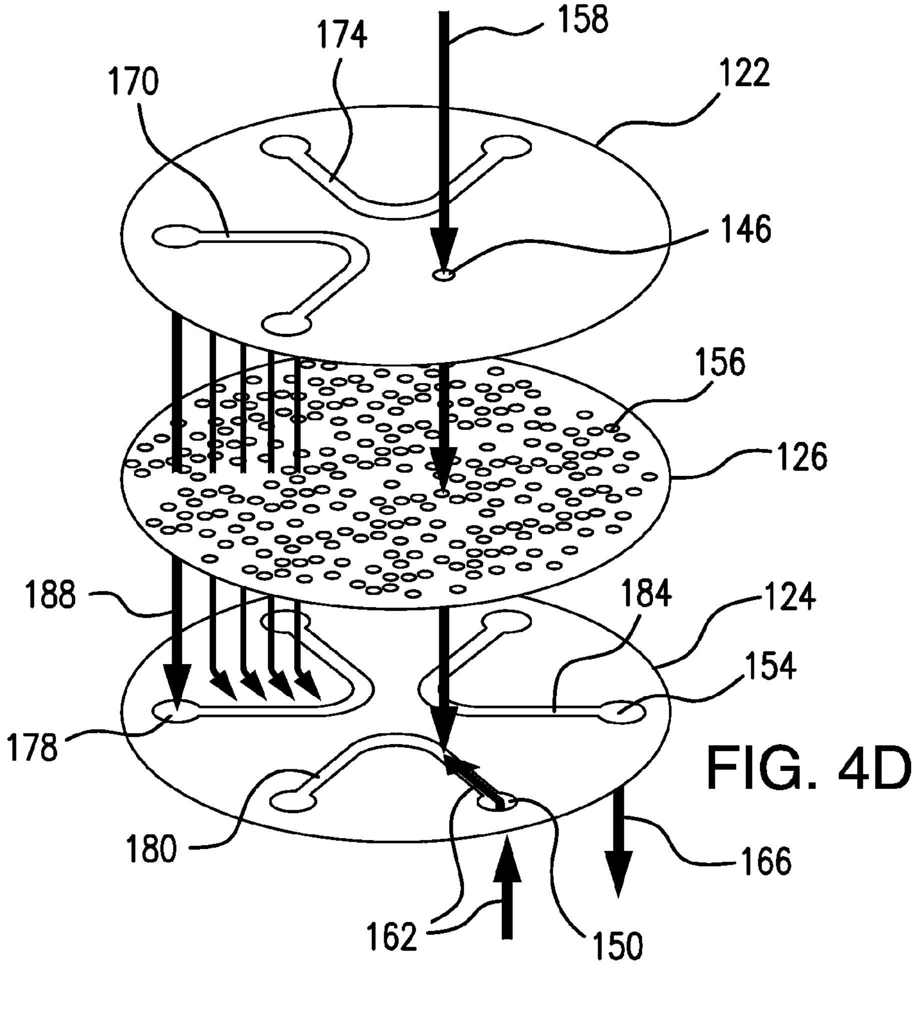
FIG. 4D is an exploded view of the internal components of the device shown in FIG. 4A.

FIG. 4D shows an exploded view of the inner components of emulsion-generating device 94. As depicted in FIG. 4D, top channel gasket 122 can comprise a first flow-path channel 170 and a second flow-path channel 174, defined within the bottom surface of top channel gasket 122. First flow-path channel 170 and a second flow-path channel 174 are shown only because top channel gasket 122 is transparent. Bottom channel gasket 124 can comprise a third flow-path channel 178, a fourth flow-path channel 180, and a fifth flow-path channel 184 defined in the top surface thereof. The flow-path channels of top channel gasket 122 and bottom channel gasket 124 can be configured to have low resistance. In operation, the flows of a microreactor mixture stream 158, a carrier fluid stream 162, and a stream of emulsion droplets 166 can be directed by the flow-path channels. The flow-path channels can also direct and manipulate the flows of partially formed emulsion streams 188, in which emulsion droplets are formed but not necessarily of the proper size. By flowing back and forth through emulsion-generating membrane 126 and along the flow-path channels, the travel of the carrier fluid and microreactor mixture within emulsion-generating device 94 can be maximized as can the opportunity for the emulsion components to be mixed together to form uniformly sized microreactor droplets encapsulated in the carrier fluid. In this manner, the carrier fluid and microreactor can be appropriately mixed to form uniformly sized emulsion droplets before the emulsion is made to exit emulsion-generating device 94. Third flow-path channel 178, fourth flow-path channel 180, and fifth flow-path channel 184 can be situated such that the emulsion droplets can pass through emulsion-generating membrane 126 two or more times before the resulting emulsion droplets are output in the form of a uniform emulsion. In some embodiments, the emulsion droplets can flow back and forth through emulsion-generating membrane for three, four, five, six, seven, eight, nine, or ten times, before exiting emulsion-generating device 94, with many of the passage flow-throughs creating smaller and smaller microreactor droplets.

Figure 5:
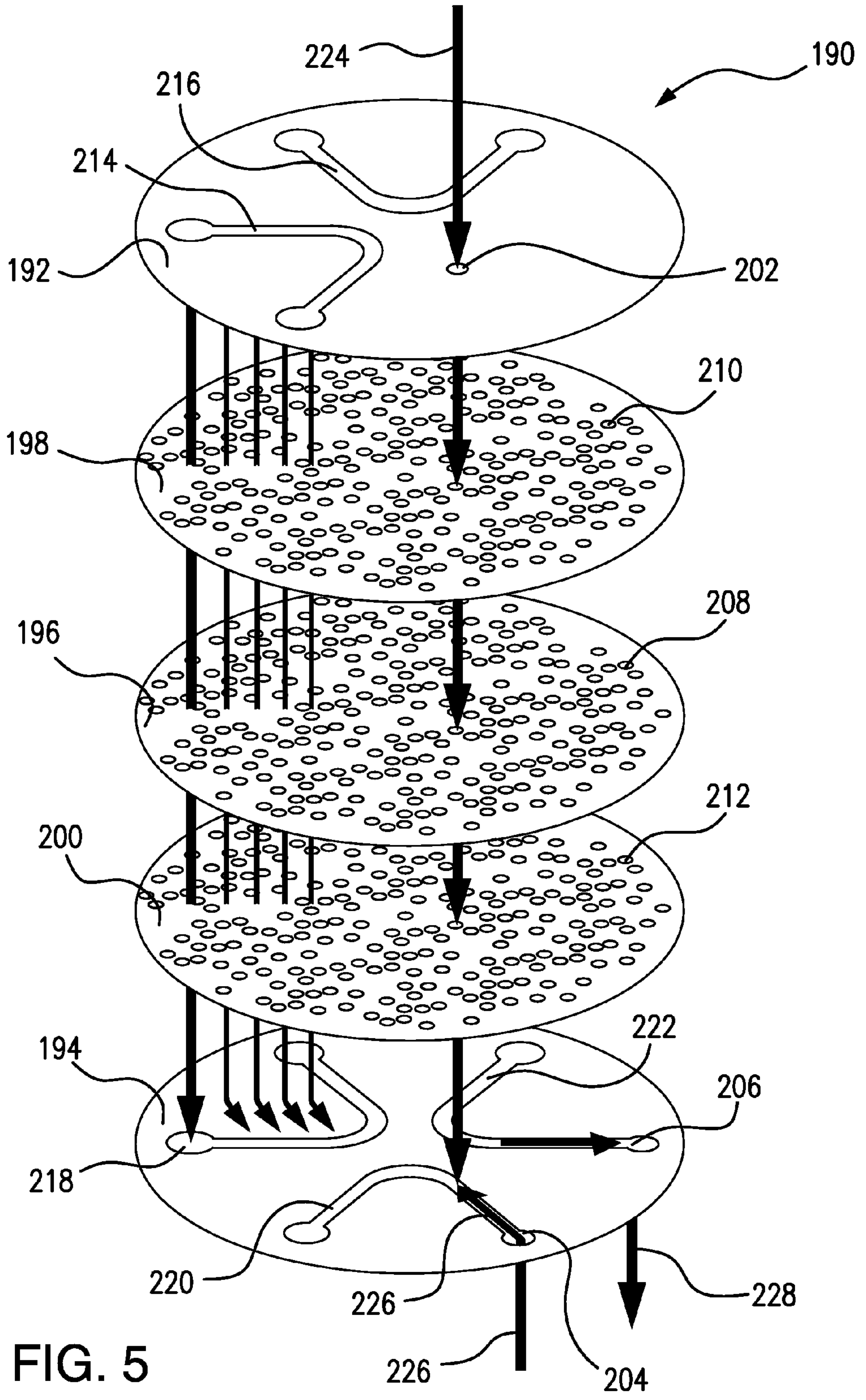
FIG. 5 is an exploded view of the internal components of a membrane-based emulsion-generating device according to yet other embodiments of the present teachings.

FIG. 5 depicts another embodiment of an emulsion-generating device, generally designated as 190 in the drawings. Emulsion-generating device 190 can comprise a top channel gasket 192 and a bottom channel gasket 194. Emulsion-generating device 190 can be substantially similar to emulsion-generating device 94 shown in FIGS. 4A-4D with the exception that a plurality of emulsion-generating membranes can be disposed between top channel gasket 192 and bottom channel gasket 194. A first emulsion-generating membrane 196, a second emulsion-generating membrane 198, and a third emulsion-generating membrane 200, can be disposed between top channel gasket 192 and bottom channel gasket 194, in a stacked configuration with respect to one another. Top channel gasket 192 and bottom channel gasket 194 can themselves form endwalls of a container or can be encased in an outer container, housing, or enclosure. Device 190 can comprise an outer container (not shown) inside of which emulsion-generating membrane 196, emulsion-generating membrane 198, emulsion-generating membrane 200, top channel gasket 192, and bottom channel gasket 194, can be disposed. The outer container, not shown in FIG. 5, can be configured as described above with respect to container 142. The outer container can comprise, for example, a microreactor mixture supply input port, a carrier fluid input port, and an emulsion output port, as previously described.

Top channel gasket 192 can comprise a first gasket port 202 that can be aligned with the microreactor mixture supply input port of the outer container. Bottom channel gasket 194 can comprise a second gasket port 204 that can be aligned with a carrier fluid input port of the outer container. A third gasket port 206 that can be aligned with an emulsion output port of the outer container. Emulsion-generating membranes 196, 198, and 200 can comprise a plurality of through holes exemplified as 208, 210, and 212, respectively. The plurality of through holes in the emulsion-generating membranes can each be circular in cross-section and the plurality of them can be substantially uniform in size. Top channel gasket 192 can comprise a first flow-path channel 214 and a second flow-path channel 216 defined within a bottom surface of top channel gasket 192 and visible in FIG. 5 only because top channel gasket 192 is transparent. Bottom channel gasket 194 can comprise a third flow-path channel 218, a fourth flow-path channel 220, and a fifth flow-path channel 222 defined within a top surface of bottom channel gasket 194. A microreactor mixture stream 224, a carrier fluid stream 226, and a stream of emulsion droplets 228 can travel through the through holes of the emulsion-generating membranes and can be directed and manipulated by the flow-path channels toward and through third gasket port 206.

The channel gaskets 122 and 124 provide flow paths through the membrane 126 so that the emulsion traverses the membrane 126 more than once such as at least 2 times, at least 3 times or even more. In the embodiments illustrated in FIGS. 4D and 5, the channels 170, 174, 178, 180, and 184 or 214, 216, 218, 220, and 222 form complementary passageways in which the carrier fluid and emulsion pass through the membrane more than once. In the illustrated embodiment of FIG. 4D, the complementary flow path is countercurrent. For example, when the emulsion passes from the bottom channel gasket 124 through the membrane 126 to the top channel gasket 122, the fluid traveling within the channel of the bottom channel gasket 124 is flowing in an opposite direction as a fluid passing through the channel of the top channel gasket 122. Such flow is referred to as countercurrent flow providing a countercurrent complementary flow path between the gaskets 122 and 124.

Figure 32:
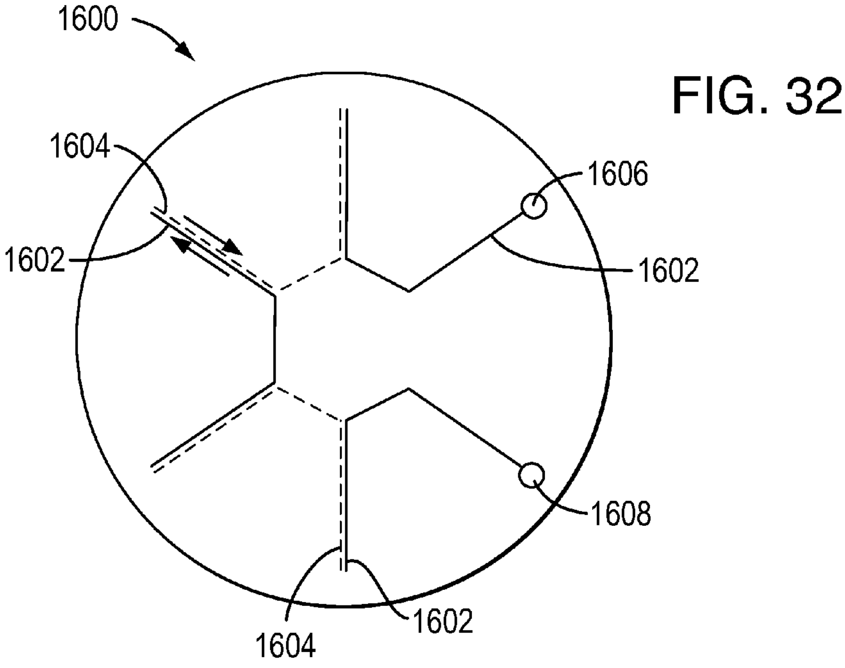
FIG. 32 and FIG. 33 include illustrations of exemplary channel gasket designs.

In an example illustrated in FIG. 32, a channel 1602 of a channel gasket 1600 flow in one direction along portions of the channel 1602 that overlap with the channel 1604 of the top channel gasket. The channel 1604 is illustrated in broken lines indicating its disposition on a different channel gasket. Accordingly, the carrier fluid enters through port 1608 traversing back-and-forth across the membrane through a countercurrent complementary flow path and an emulsion exits through port 1606.

Figure 33:
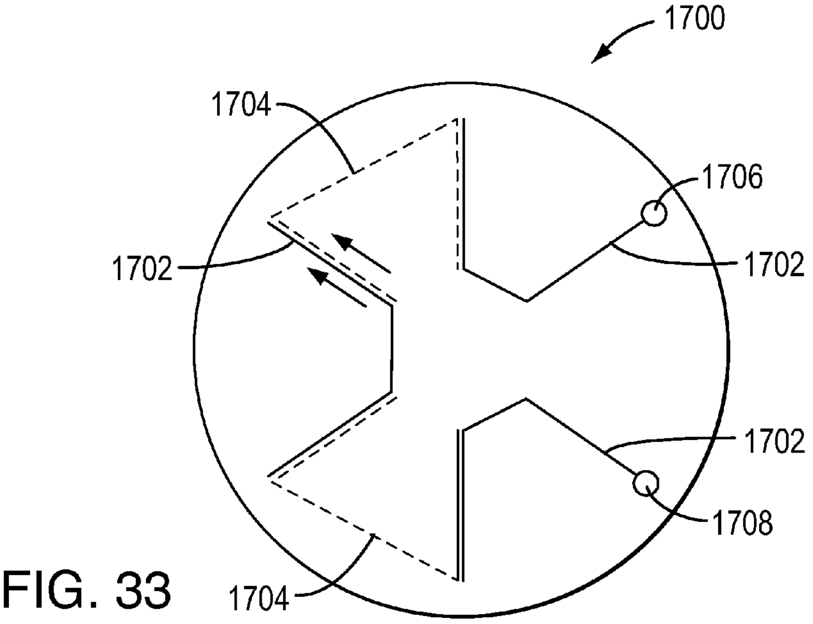

In an alternative example, FIG. 33 illustrates the flow path 1700 that includes concurrent flow. For example, flow of a carrier fluid can enter port 1708 and traverse channels 1702. In regions of overlap, the flow direction in the channel 1702 is the same as the flow direction in channel 1704 of the opposing gasket. As such, the flow is concurrent or parallel in the overlapping regions as emulsion passes from the bottom gasket through the membrane to the top gasket. Similarly, the flow is concurrent when the emulsion passes from the top gasket through to the bottom gasket. As such, FIG. 33 illustrates an exemplary concurrent complementary flow path 1700. According to various embodiments, a method of making a membrane-based emulsion can comprise pumping or dispensing a volume of a microreactor mixture in the microreactor input port of an emulsion-generating membrane device to form a microreactor mixture stream. Simultaneously or sequentially, a volume of carrier fluid can be pumped or dispensed through a carrier fluid input port of the emulsion-generating membrane device to form a carrier fluid stream. External pressure can be applied to move the microreactor stream and the carrier fluid stream, for example, alternatively, through the through holes of the emulsion-generating membrane to cause the carrier fluid stream and the microreactor stream to mix together and form an emulsion stream comprising microreactor droplets.

According to some embodiments, the emulsion stream of microreactor droplets can be directed by the flow-path channels of the top channel gasket and of the bottom channel gasket to the through holes of the emulsion-generating membrane or to the third gasket port. The stream of emulsion droplets can travel through the through holes of the emulsion-generating membrane one or more times before exiting the device through the output port. The emulsion droplets can be sheared into smaller droplets as the emulsion droplets are pushed back and forth through the through holes. The emulsion droplets can be pushed back and forth through the through holes, two or more times, for example, six, seven, eight, nine, or ten times, such that microreactor droplets of uniform size and volume are generated.

In an embodiment, the present teachings provide a plate-based emulsion-generating device. The emulsion-generating device may comprise a first plate and a second plate configured to form a flow chamber; a fluid input port and a fluid output port in fluid communication with the flow chamber; at least the first or second plate comprising a plurality of through holes passing through the first or second plate in a plate thickness direction; the plurality of through holes being disposed in one or more lines oriented at a substantially perpendicular direction with respect to a direction from the fluid input port toward the fluid outlet port. In an embodiment, the plurality of through holes is disposed in one or more straight lines. However, none straight lines, e.g., curves and zigzag lines are also contemplated. A person skilled in the art would readily select a suitable arrangement of the through holes as long as, inter alia, the droplets generated from different through holes would not interfere with each other. In an embodiment, the device can further comprise a respective elevated rim around each of the through hole.

In another embodiment, the first plate is a top plate and the second plate is a bottom plate, and the bottom plate may comprise the plurality of through holes.

In another embodiment, the present teachings provide a system for making emulsion droplets, comprising a plate-based emulsion-generating device, a reaction mixture supply in fluid communication with the flow chamber by way of the plurality of through holes, a carrier fluid supply in fluid communication with the flow chamber by way of the fluid inlet port, and an emulsion collection device in fluid communication with the flow chamber by way of the outlet fluid port. In an embodiment, the reaction mixture supply or the carrier fluid supply are pressurized.

The present teachings also provide a method of making an inverse emulsion from a reaction mixture and an immiscible carrier fluid using the plate-based emulsion-generating device. The method may comprise flowing the reaction mixture into the flow chamber through the through holes, flowing the carrier fluid into the flow chamber through the fluid inlet, and forming a plurality of droplets of the reaction mixture in the carrier fluid, thus forming an inverse emulsion. The method can further comprise recovering the inverse emulsion from the fluid outlet port. In an embodiment, the method may comprise adjusting a fluid pressure of the reaction mixture or adjusting a fluid pressure of the carrier fluid such that the droplets of the reaction mixture in the carrier fluid have a predetermined size. In a preferred embodiment, the reaction mixture may comprise an aqueous phase solution, a plurality of template beads, a library of templates from a sample, DNA polymerase, and a pair of primers.

In an alternative embodiment, an aqueous mixture is placed in a sample vial, which is coupled to the top port of an emulsion generating device. A displacement fluid rises into the sample vial pushing the more dense aqueous solution into the emulsion generating device. For example, FIG. 25, FIG. 26, FIG. 27, FIG. 28, FIG. 29, FIG. 30, and FIG. 31 illustrate alternative embodiments of the emulsion generating device. For example, an emulsion generating device 1500 has upper portion 1502 and a lower portion 1504. The emulsion generating device 1500 also includes a top channel gasket 1506, and bottom channel gasket 1510, and an emulsion generating membrane 1508 disposed between the top channel gasket 1506 and the bottom channel gasket 1510. In an example, the membrane 1508 can be separated from the top channel gasket 1506 or the bottom channel gasket 1510 by a distance of at least 500 μm. In an alternative example, the membrane 1508 is in direct contact with the top channel gasket 1506 or the bottom channel gasket 1510, restricting fluid flow to the channel regions within the gaskets 1506 or 1510. At the top portion 1502 of the emulsion generating device 1500, the port 1514 is to receive a sample vial 1512, providing fluid access between the sample vial 1512 and emulsion generating device 1500.

The bottom portion 1504 of the emulsion generating device 1500 can include carrier fluid input port 1516 for inserting carrier fluid, such as oil. On the bottom portion 1504, the emulsion generating device can also include an emulsion outlet port 1518 to receive the generated emulsion. Such carrier fluid input port 1516 and the emulsion outlet port 1518 can function as described above.

In an additional example, the bottom portion 1504 of the emulsion generating device 1500 can include a displacement fluid input port 1520. In an example, a passageway 1530 can be formed within the top channel gasket 1506, the membrane 1508, and the bottom channel gasket 1510 to permit the flow of the displacement fluid from the displacement fluid port 1520 to the sample vial 1512 through the sample port 1514. In an example, the displacement fluid applied through the displacement port 1520 can be a fluid having similar properties to the carrier fluid. Alternatively, displacement fluid can be different than the carrier fluid. Optionally, the displacement fluid is miscible in the carrier fluid. Alternatively, the displacement fluid is immiscible in a carrier fluid. In a particular example, the displacement fluid is immiscible with the aqueous solution and has a density less than the aqueous solution. While the displacement fluid input port 1520 is illustrated as being part of the bottom portion 1504 of the emulsion generating device 1500, alternatively, the displacement fluid input port 1520 can be formed in the upper portion 1502 of the emulsion generating device 1500. Alternatively, the system can be free of a displacement fluid input port 1520 and the fluid path of the carrier fluid to be fed through the carrier fluid input port 1516 can be directed to displace the aqueous solution within the sample vial 1512.

Yet another embodiment of an emulsion-generating device and subsystem is shown in FIGS. 21A-23. According to some embodiments, other devices and subsystems can be used to generate emulsions. In some embodiments, a flow cell or plate-based emulsion-generating device can be provided to form emulsion droplets comprising microreactors. In the embodiment shown in FIG. 21A, an emulsion-generating device 1400 is shown comprising a substrate 1404 at least partially defined by an emulsion-generating plate 1408 and a cover 1412 disposed over and in contact with the periphery of emulsion-generating plate 1408. Emulsion-generating plate 1408 can comprise at least one row 1416 of one or more nozzles or through holes 1420 formed through the plate. According to various embodiments, emulsion-generating plate 1408 can comprise at least two through holes 1420 defined through the plate. A flow cell 1424 is provided within substrate 1404 and defined as the volume between emulsion-generating plate 1408 and cover 1412. The at least one row 1416 of one or more through holes 1420 can be oriented in a straight line within flow cell 1424. Row 1416 can be arranged perpendicularly or angled within about 10 degrees or less with respect to perpendicular, relative to a direction of flow of a crier fluid and resulting emulsion through the flow cell. The direction can be a direction from a flow cell input toward a flow cell output. A flow cell ledge or wall 1428 can be disposed around the perimeter of flow cell 1424.

According to various embodiments, cover 1412 can comprise a carrier fluid inlet port 1432 through which a carrier fluid 1434 can enter flow cell 1424. The arrows representing flow 1434 are schematic in nature and shown in the interior of flow cell 1424 by virtue of cover 1412 being transparent. Alternatively, cover 1412 can be opaque, non-transparent, translucent, black, non-light-transmissive, or the like. According to various embodiments, each through hole 1420 can comprise a microreactor mixture inlet port. Carrier fluid inlet port 1432 can be circular in cross-section and can be the same size, smaller than, or larger than an emulsion outlet port 1436 also formed in cover 1412. A flow of carrier fluid can be made through flow cell 1424 by supplying a carrier fluid under pressure through carrier fluid inlet port 1432 to fill flow cell 1424 and exit emulsion outlet port 1436. A volume of microreactor mixture can then be dispensed through a through hole 1420 and into the interior of flow cell 1424. The microreactor mixture can be forced through emulsion-generating plate 1408 through each of the through holes 1420 in row 1416 and into the flow of carrier fluid through flow cell 1424. Emulsion droplets 1440 can be formed once the microreactor mixture is forced out of emulsion-generating plate 1408 through a through hole 1420 and sheared off of the microreactor supply remaining in the through hole. The flow of the carrier fluid, the microreactor mixture, or both can be adjusted to control the shearing effect and the size of the microreactor droplets sheared from the through holes. Emulsion outlet port 1436, through which the resultant inverse emulsion 1440 leaves the emulsion-generating device, can be in fluid communication with a collection device, for example, a collection tube. In some embodiments, emulsion outlet port 1436 can be in direct or indirect fluid communication with a thermocycling plate, for example, a thermocycling plate as described herein. The walls of flow cell 1424 can retain carrier fluid 1434 and inverse emulsion 1440 within flow cell 1424.

Emulsion-generating plate 1408 and cover 1412 can be glued, molded, ultrasonically bonded, screwed, or otherwise connected together to form substrate 1404. According to various embodiments, emulsion-generating device 1400 can be part of a machine wherein, with loading and one touch, a user can program the machine to run without user further user interaction for a processing period, for example, one hour, two hours, three hours, or longer, to produce amplified templated beads useful for sequencing.

Figure 21A:
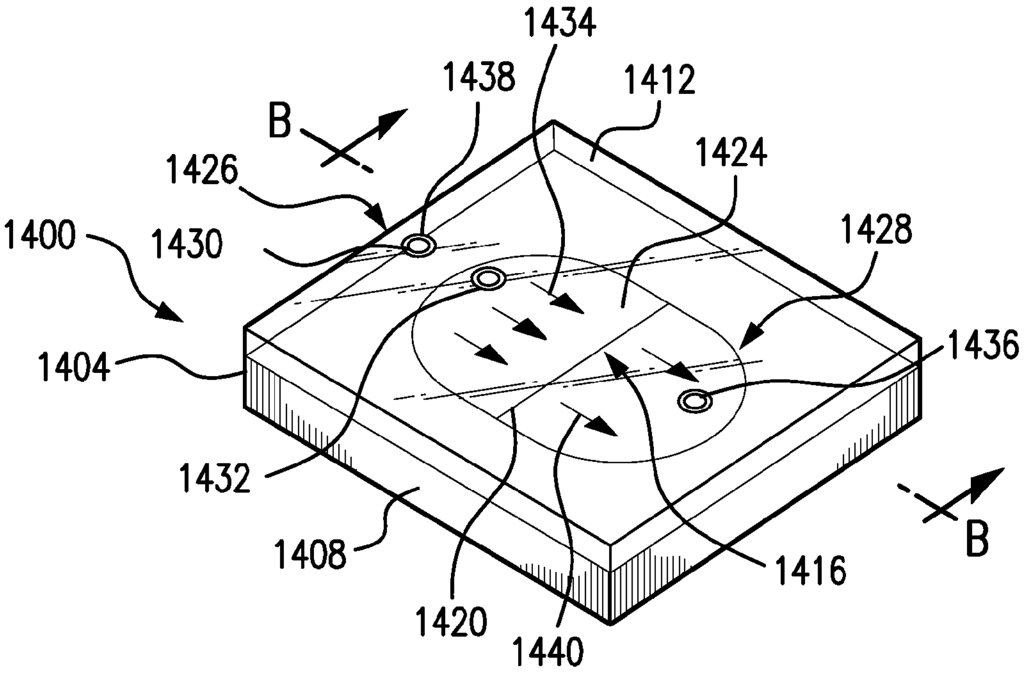
FIG. 21A is a perspective view of a plate-based emulsion-generating device according to various embodiments of the present teachings.
Figure 21B:
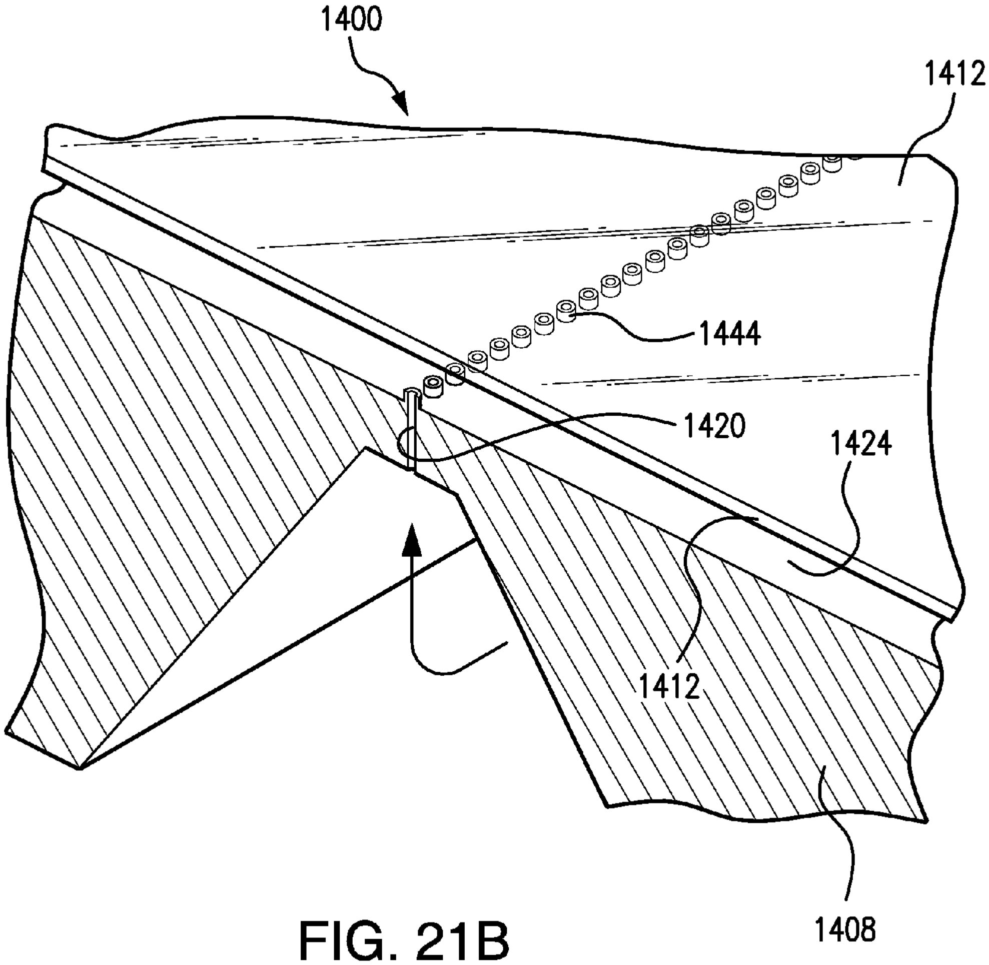
FIG. 21B is a cross-sectional view taken along line B-B of FIG. 21A.

FIG. 21B is a cross-sectional view taken along line B-B of FIG. 21A. As shown in FIG. 21B, each of through holes 1420 can be a straight through pore through which a straight line can be drawn that does not touch or intersect the wall of the pore. Each of the through holes 1420 can be circular in cross-section and can be substantially uniform in size. According to some embodiments, each of the through holes 1420 can have a diameter of, for example, from about 1 to about 30 microns, from about 3 to about 15 microns, from about 8 to about 14 microns, or from about 10 to about 12 microns. According to some embodiments, flow cell 1424 can comprise a row of about 50 to about 100 through holes. Through holes 1420 can be arranged substantially perpendicular to the flow of carrier fluid through flow cell 1424. According to some embodiments, flow cell 1424 can comprise from about 60 to about 90 through holes. According to some embodiments, flow cell 1424 can comprise from about 70 to about 80 through holes. According to some embodiments, flow cell 1424 can comprise about 60, about 70, about 80, about 90, or about 100 through holes.

According to various embodiments, a respective rim or nozzle 1444 can be formed or provided on emulsion-generating plate 1408 around each of the one or more through holes 1420. Nozzle 1444 can help to make droplets of uniform size or to eject the droplets at a location in flow cell 1424 that is spaced from the flow cell floor. Nozzle 1444 can reduce or eliminate the possibility of droplets merging with each other. In some embodiments, nozzle 1444 is not surface treated, or does not comprise a surface coating. According to some embodiments, nozzle 1444 can be treated or can be provided with a surface coating. In some embodiments, nozzle 1444 can comprise a semiconductor-type material, for example, silicon.

Figure 22:
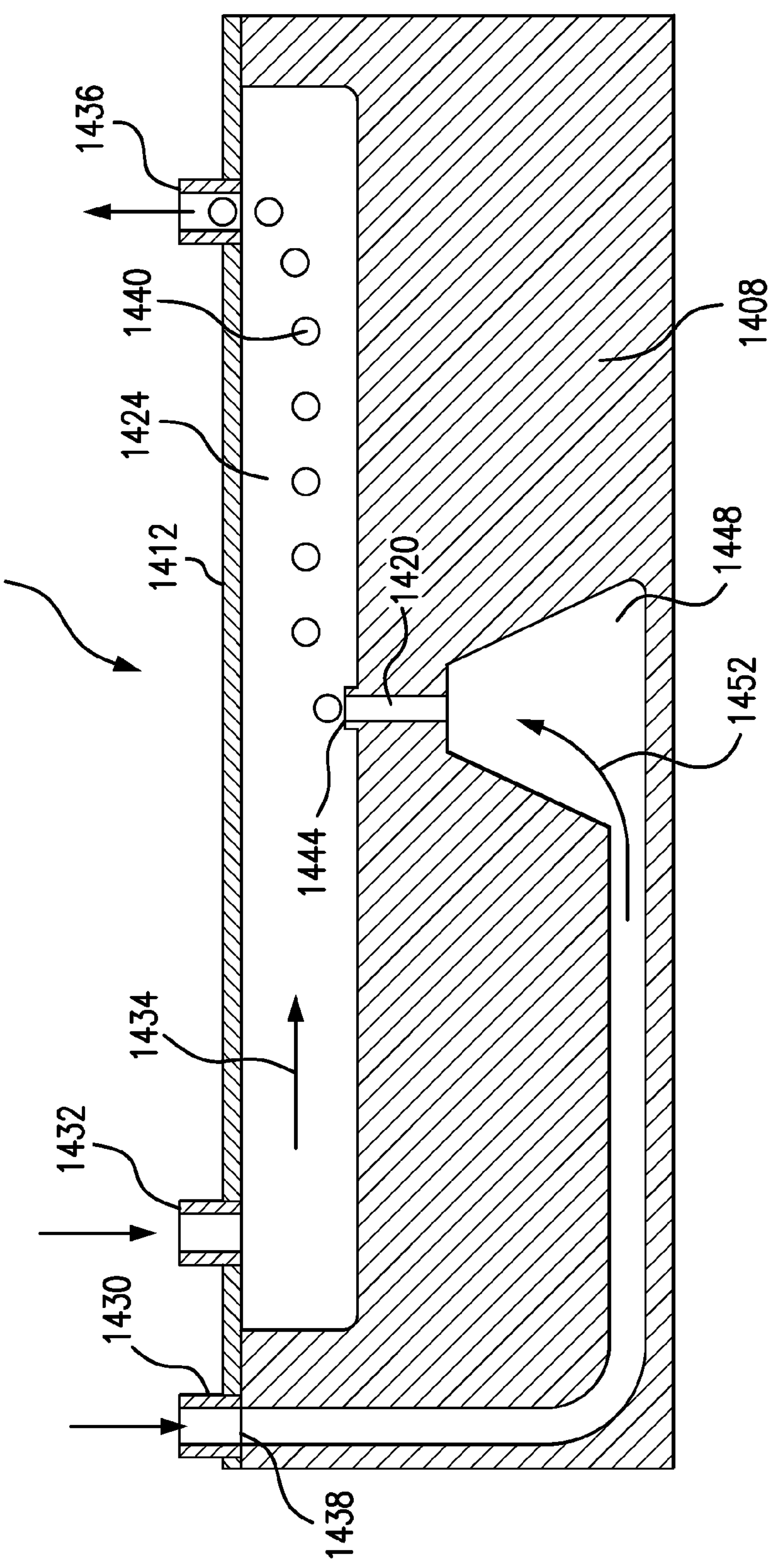
FIG. 22 is a cross-sectional side view of a plate-based emulsion-generating device according to various embodiments of the present teachings.

As shown in FIG. 22, emulsion-generating plate 1408 can also contain, define, or at least partially define, a cavity 1448 that, in operation, is filled with the microreactor mixture and in fluid communication with through holes 1420. As shown, the top surface of emulsion-generating plate 1408 can face cover 1412. Flow cell 1424 can be in the form of a well or chamber at least partially defined by the top surface of emulsion-generating plate 1408. Cavity 1448 can be in the form of an interior cavity inside emulsion-generating plate 1408 or it can defined by both emulsion-generating plate 1408 and a bottom plate or cover (not shown). In some embodiments, cavity 1448 can be drilled from a side of emulsion-generating plate 1408 and sealed on the end by a side wall (not shown). Through holes 1420 can provide fluid communications between flow cell 1424 and cavity 1448. In some embodiments, cavity 1448 and emulsion-generating plate 1408 can be configured to sit directly on, or connect to, a supply source, port, or connection for a microreactor mixture supply.

According to various embodiments, a pressurized supply of a microreactor mixture and a pressurized supply of carrier fluid can be connected to emulsion-generating device 1400. The pressurized supply of microreactor mixture can be connected to a microreactor inlet port 1430. The pressurized supply of carrier fluid can be connected to a carrier fluid inlet port 1432. In the embodiment shown, the microreactor mixture from the pressurized supply of microreactor mixture can be dispensed into emulsion-generating plate 1408 through inlet port 1430 and through a microreactor mixture conduit 1438 in fluid communication with inlet port 1430. The microreactor mixture can travel downwardly into emulsion-generating plate 1408, in a direction away from the top surface of emulsion-generating plate 1408, then horizontally through conduit 1438 in a direction parallel to the top surface of emulsion-generating plate 1408. The flow of microreactor mixture, denoted as reference numeral 1452, can then travel upwardly through cavity 1448 and through through holes 1420. At about the same time that microreactor mixture is dispensed into emulsion-generating plate 1408, the carrier fluid from the pressurized supply of carrier fluid can be dispensed into flow cell 1424 through carrier fluid inlet port 1432. The carrier fluid can flow in flow cell 1424 in a direction that is parallel to the top surface of emulsion-generating plate 1408 and toward emulsion outlet port 1436. The microreactor mixture can be forced out of emulsion-generating plate 1408 through the through holes 1420 and into the carrier fluid flowing through flow cell 1424. As the carrier fluid flow shears portions of the microreactor mixture from nozzles 1444, microreactor droplets 1440 are formed.

Figure 23:
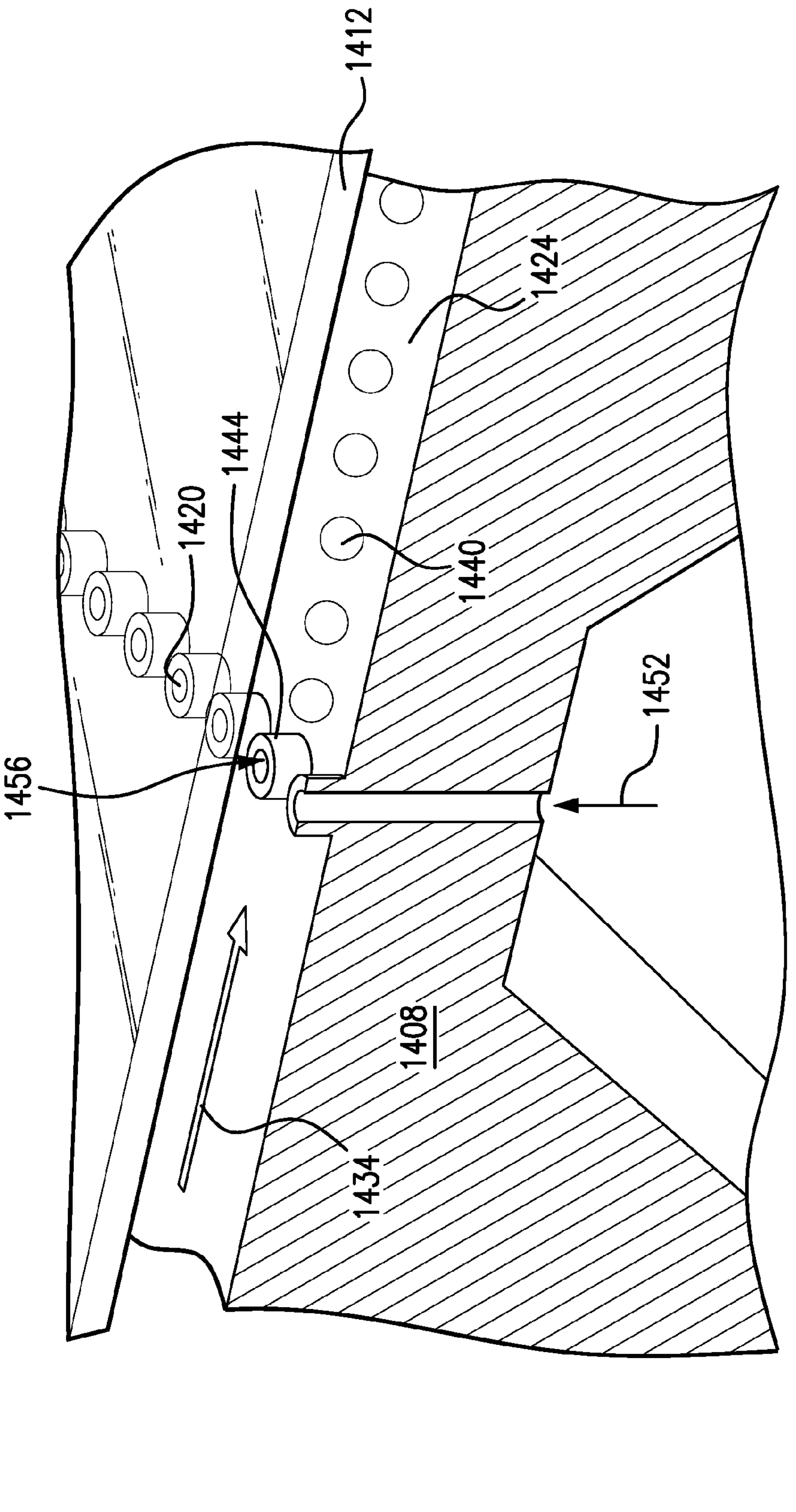
FIG. 23 is perspective, partial cutaway view of a plate-based emulsion-generating device according to various embodiments of the present teachings.

According to some embodiments, as shown in FIG. 23, each nozzle 1444 can have a small, elevated, top surface 1456 to help minimize surface-wetting-induced size variability. According to some embodiments, top surface 1456 can be substantially flat. According to some embodiments, top surface 1456 can have a uniform width of about 2 microns to about 11 microns in a radial direction. In some embodiments, nozzle 1444 can have an inside diameter of from about 1 micron to about 40 microns, or from about 10 microns to about 20 microns. According to some embodiments, the one or more through holes 1420 can each have an inside diameter of from about 1 to about 40 microns or from about 11 to about 18 microns. Each nozzle 1444 can extend from about 10 microns to about 20 microns above the flow cell bottom. According to some embodiments, nozzle 1444 can extend about 15 microns above the flow cell bottom. In some embodiments, nozzle 1444 can have an inside diameter of about 11, 12, 13, 14, or 15 microns. In some embodiments, nozzle 1444 can have an outside diameter of from about 20 microns to about 30 microns. According to some embodiments, nozzle 1444 can have an outside diameter of about 22, 23, 24, 25, 26, or 27 microns.

Each nozzle 1444 can have any appropriate shape. Each nozzle 1444 can be cylindrically-shaped, tear-drop shaped, square-shaped, or the like. The plurality of nozzles can be spaced from one another at a pitch of from about 10 to about 50 microns, for example, from about 30 to about 40 microns. In some embodiments, the plurality of through holes 1420 can be spaced apart at a pitch of about 33, 34, 35, 36, or 37 microns.

Emulsion-generating plate 1408 can be molded, machined, drilled, or track-etched to form the one or more through holes. Track-etched through holes can be fabricated using photo-lithography, chemical etching, and reactive ion etching (RIE). Emulsion-generating plate 1408 can be rigid or flexible and can comprise plastic, a polymer, glass, metal, silicon, a combination thereof, or the like. In some embodiments, emulsion-generating plate 1408 can comprise a glass or a polymer. Exemplary polymers that can be used include, but are not limited to, poly(ether sulfone), polyester, polyisoprene, polycarbonate, polyvinylpyrrolidone, polyimide, polytetrafluoroethylene (PTFE), fluorinated polymers, perfluorinated polymers, poly cyclo-olefins, combinations and blends thereof, and the like.

Emulsion PCR and Thermocycling Subsystem

An emulsion generated can be thermally cycled, or thermocycled, to effect a polymerase chain reaction in each aqueous droplet. For such purpose, a thermocycling subsystem is provided according to the present teachings and can comprise a first thermocycling plate, as described herein, and a heating subassembly, as described herein. The heating subassembly of the thermocycling system can also comprise a complementary heating block as described herein. The heating subassembly of the thermocycling system can also comprise a second thermocycling plate.

A heating subassembly is provided by the present teachings that can be used in combination with one or more thermocycling plates described herein. The heating subassembly can comprise a first heating block, a first heat control unit, a second heat control unit, and, optionally, a negative load device. The first heating block can comprise a first static heating zone, a heating zone partition, and a second static heating zone separated from the first static heating zone by the heating zone partition. The first heat control unit is operably associable with the first static heating zone. The second heat control unit is operably associable with the second static heating zone. The negative load device can be operably associated with the second heat control unit and the second static heating zone. Any type of negative load device can be used that can exert a negative temperature effect. For example, the negative load device can comprise a fan, a heat sink, or both. A power source can be electrically associated with the first and second heat control units.

The shape of the one or more heating blocks employed can adapted for compatibility with the one or more thermocycling plates used. For example, one or more heating blocks of the heating subassembly can comprise one or more recess configured to allow passage of a thermocycling plate inlet, a thermocycling plate outlet, or tubing associated with at least one of the inlet and the outlet, or any combination thereof. Any type of heater or combination of heaters can employed for the static heating zones. Examples of heaters include narrow strip (ribbon) heaters, fluid-filled channel heaters, Peltier heaters, static zone heaters, electrical resistance heaters, and the like.

Figure 6A:
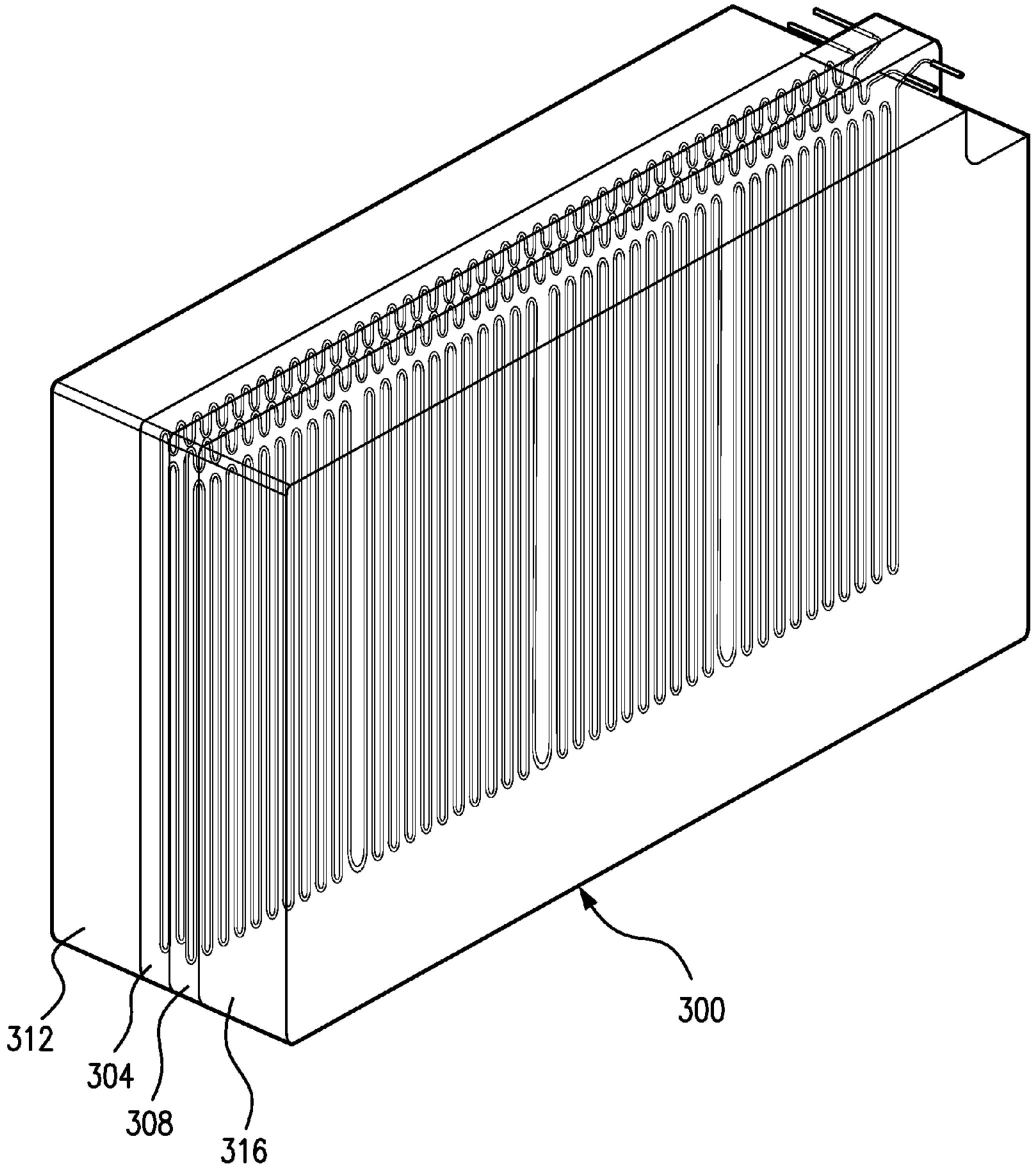
FIG. 6A is a side perspective view of a thermocycling subsystem in accordance with various embodiments of the present teachings.
Figure 6B:
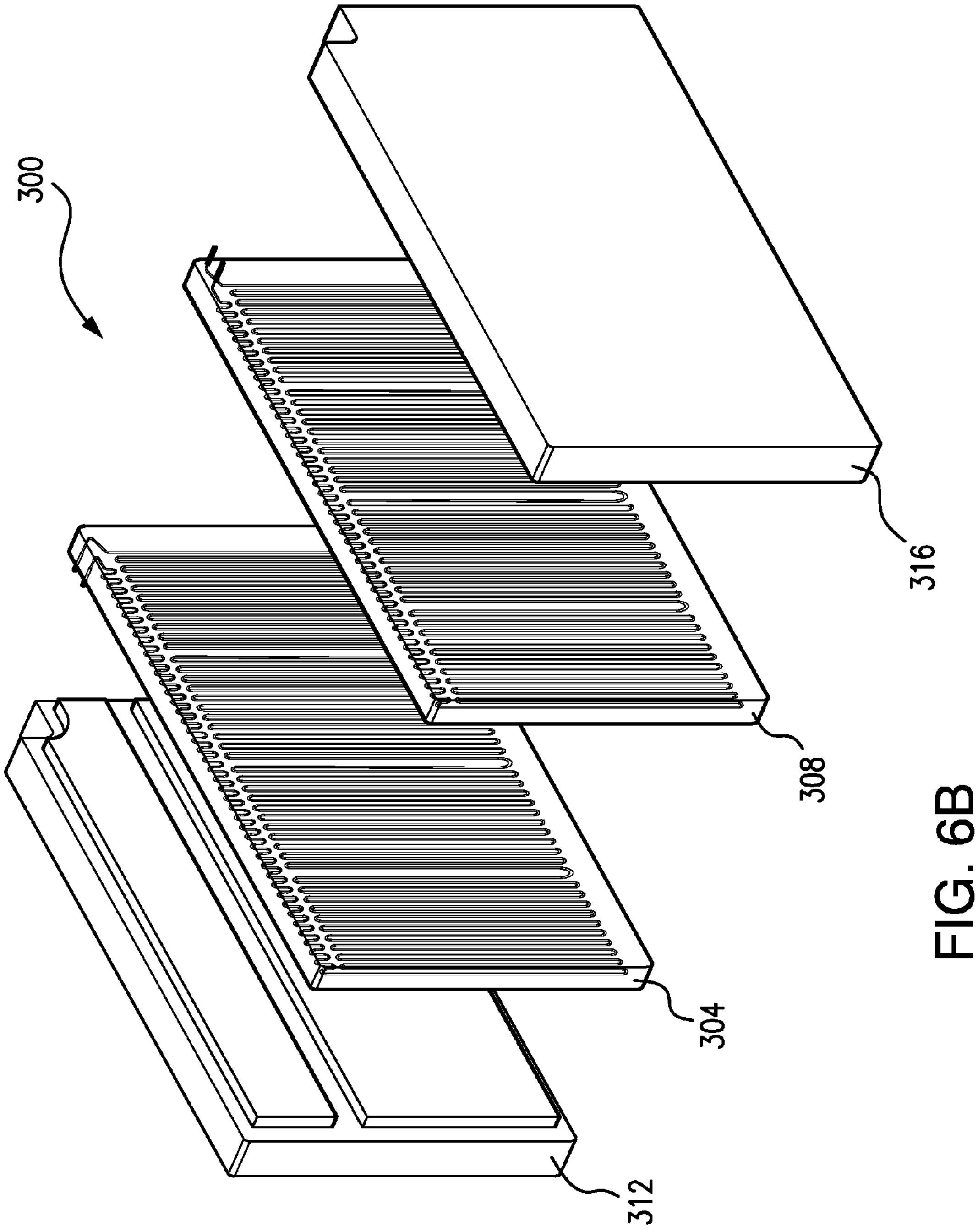
FIG. 6B is an exploded view of the thermocycling subsystem shown in FIG. 6A.
Figure 6C:
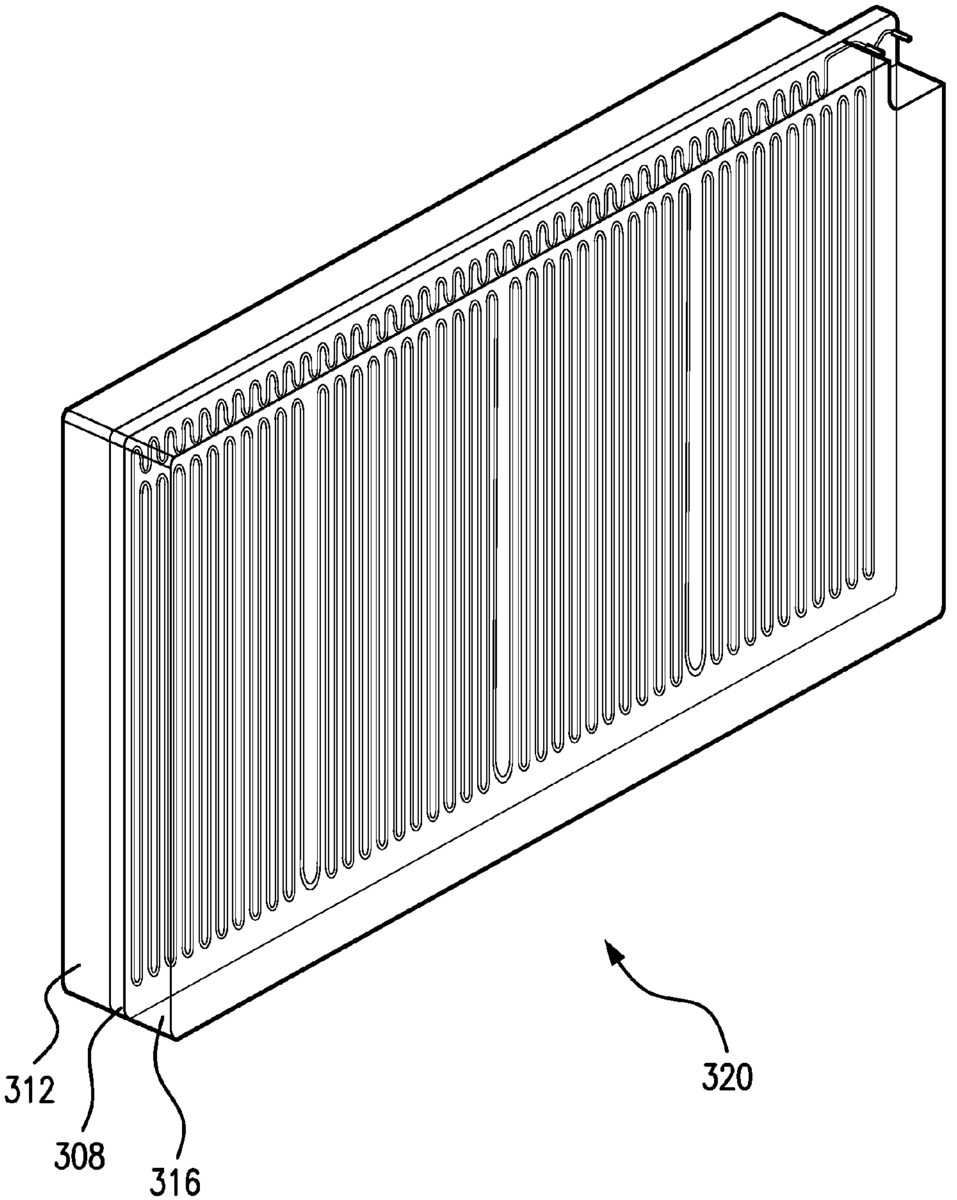
FIG. 6C is a side perspective view another thermocycling subsystem in accordance with various embodiments of the present teachings.
Figure 6D:
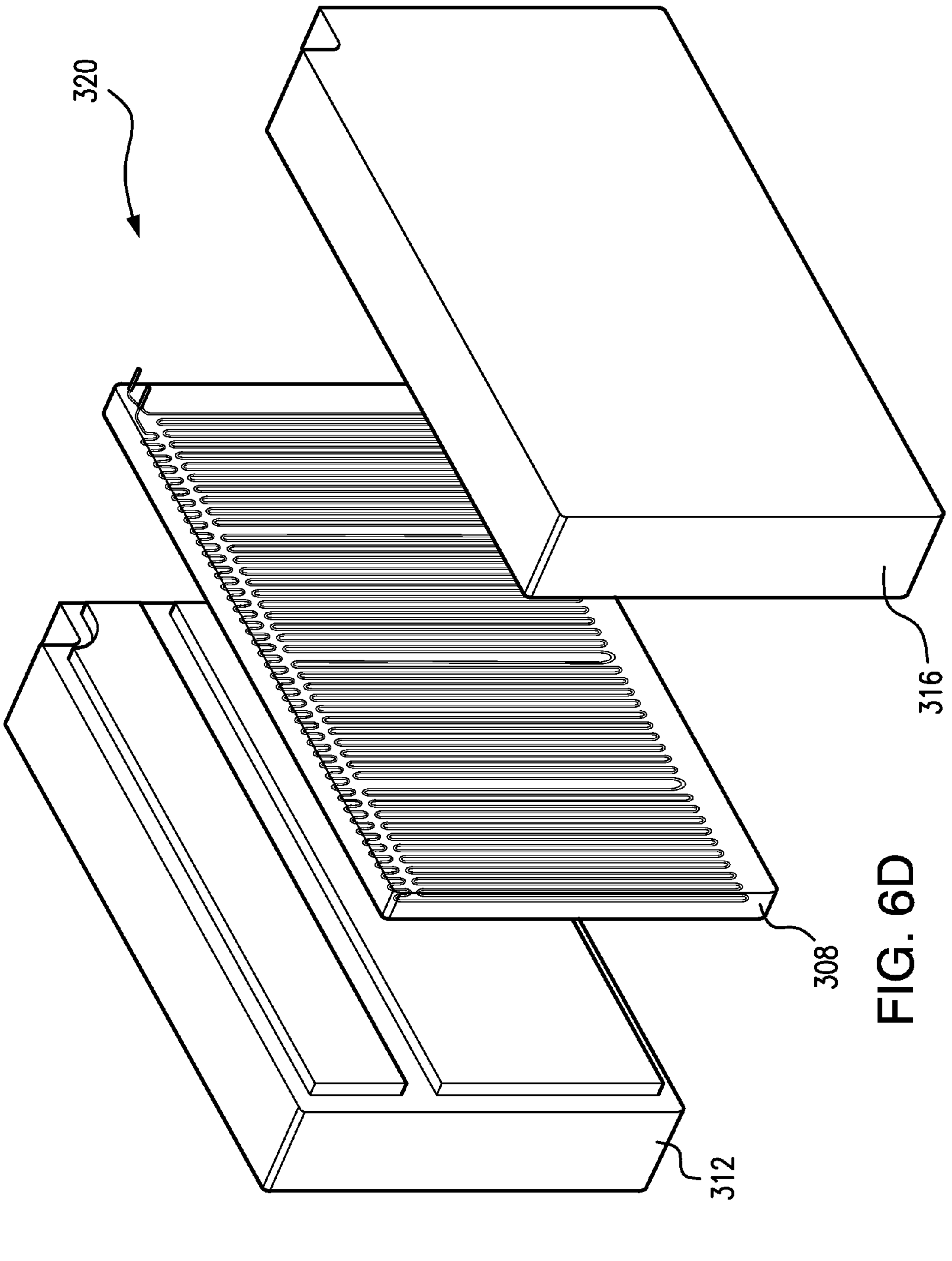
FIG. 6D is an exploded view of the thermocycling subsystem shown in FIG. 6C.

FIG. 6A is a thermocycling subsystem of an embodiment of the present teachings. thermocycling subsystem 300 is shown with four components in a sandwiched configuration. A first thermocycling plate 304 and a second thermocycling plate 308 are shown sandwiched between a first heating block 312 and a second heating block 316. FIG. 6B shows an exploded view of the thermocycling subsystem 300 as shown in FIG. 6A. FIG. 6B highlights and shows the portions of the respective heating blocks that correspond to the respective thermocycling plates. More details of these various components are described below in conjunction with the other figures. FIG. 6C shows another thermocycling subsystem 320, which is a variation on the thermocycling subsystem 300. Thermocycling subsystem 320 again shows heating blocks 312 and 316, but with only a single thermocycling plate, here second thermocycling plate 308. Other embodiments consistent with the present teachings consisting of variations on the thermocycling subsystems 300 and 320 will be readily understandable to one of ordinary skill in the art. For example, a variation on thermocycling subsystem 320 could instead involve first thermocycling plate 304 instead of second thermocycling plate 308. A single heating block can be employed in those embodiments where a single thermocycling plate is present. FIG. 6D shows an exploded view of thermocycling subsystem 320 as shown in FIG. 6C analogous to the exploded view of FIG. 6A shown in FIG. 6B.

Figure 7B:
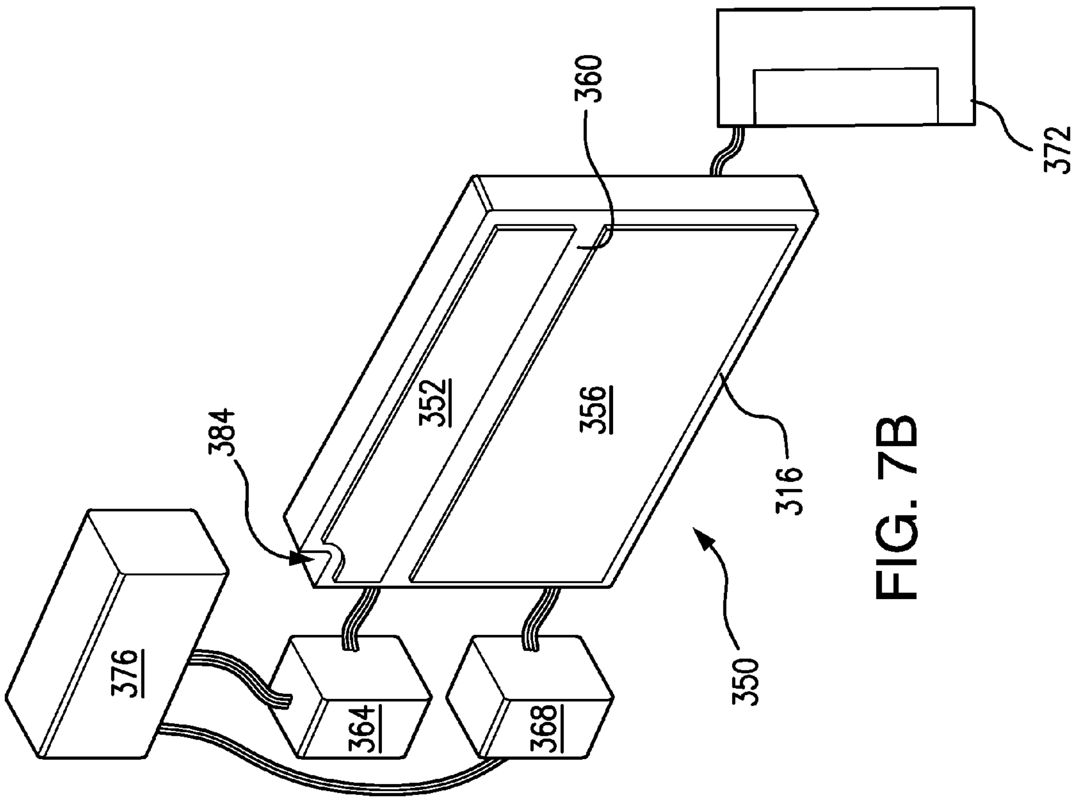
FIG. 7B is a perspective view and mirror image of the heating subassembly shown in FIG. 7A.
Figure 7A:
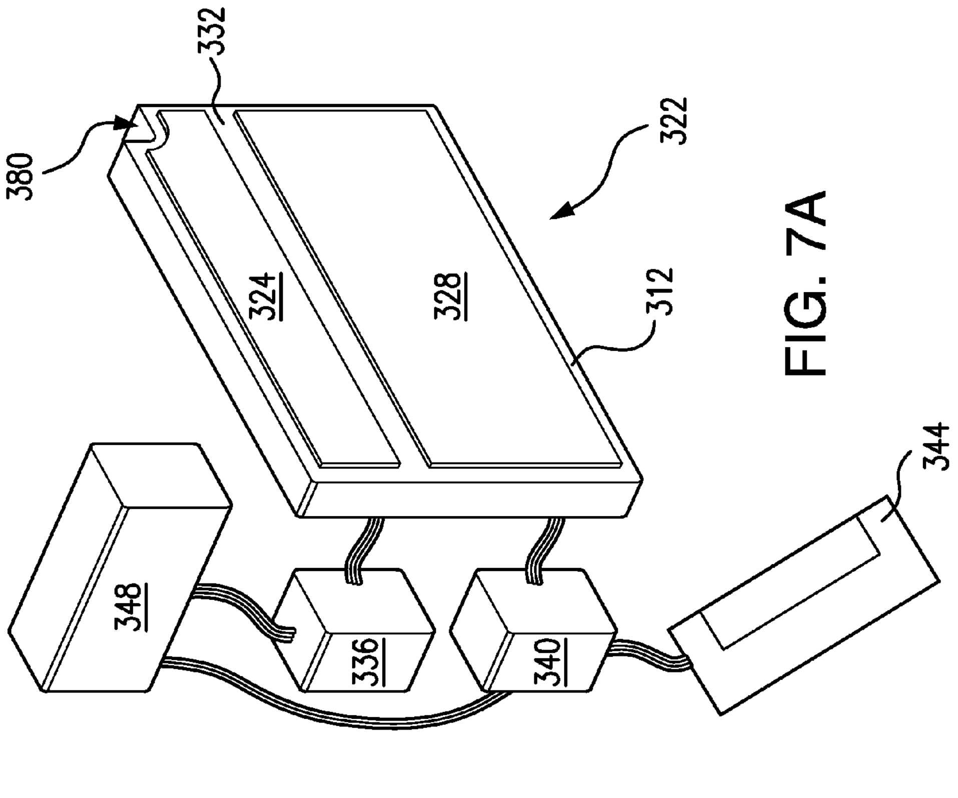
FIG. 7A is a perspective view of a heating subassembly for use in a thermocycling subsystem in accordance with various embodiments of the present teachings.

FIG. 7A shows a heating subassembly 322 and FIG. 7B shows a second heating subassembly 350, which is a mirror image of subassembly 322. Subassembly 322 can comprise first heating block 312. First heating block 312 comprises a first static heating zone 324, a second static heating zone 328, and an insulation/buffer zone 332 between first static heating zone 324 and second static heating zone 328. First static heating zone 324 can be operably connected to and controlled by a first heat control unit 336, and second static heating zone 328 can be operably connected to second heat control unit 340 and controlled by the same. Heating subassembly 322 can also include a negative load device 344, which can be operably connected to and controlled by second heat control unit 340.

Both the first heat control unit 336 and the second heat control unit 340 can be operably connected to a first power source 348. Any type of power source, whether alternating current, direct current, or other type, can be used as the power source 348. Negative load 344 can be any device or means known to one of ordinary skill in the art for applying a negative temperature load. For example, negative load 344 can be in the form of a fan. The first static heating zone 324 and second static heating zone 328 can extend through any degree of the thickness of the heating block 312. First heating block 312 can have an access recess 380 in a corner to allow access of tubing connected to the first thermocycling plate 304.

While a single heating block can be employed in the heating subassembly, use of a second heating block can provide additional temperature control and is particularly advantageous when two thermocycling plates are used. Accordingly, the heating subassembly of the present teachings can comprise a complementary heating block. The complementary heating block can include a first complementary static heating zone, a complementary heating zone partition, and a second complementary static heating zone separated from the first complementary static heating zone by the complementary heating zone partition. The complementary heating block can share one or more heat control units, or other components, with the first heating block or can be provided with dedicated complementary heat control units or other components. For example, the complementary heating block can comprise a first complementary heat control unit operably associated with the first complementary static heating zone; a second complementary heat control unit operably associated with the second complementary static heating zone; and a complementary negative load device operably associated with the second complementary heat control unit and the second complementary static heating zone. The second heating block can be electrically associated with the first complementary and second complementary heat control units.

Second (complementary) heating subassembly 350 shown in FIG. 7B can be configured to have same or similar attributes as described for first heating subassembly 322. Second heating subassembly 350 includes second heating block 316. Second heating block 316 comprises first static heating zone 352, second static heating zone 356, and insulation/buffer zone 360. First heat control unit 364 and second heat control unit 368 are respectively operably associable with and can control first static heating zone 352 and second static heating zone 356. Negative load device 372 is operably connected to and can be controlled by second heat control unit 368. While first heat control unit 364 and second heat control unit 368 are shown operably connected to second power source 376, first heat control unit 364 and second heat control unit 368 can share a common power source 348 with first heating subassembly 322. Second heating block 316 is also shown with an access/recess 384 analogous to access/recess 380 in the first heating block 312.

The heat control units can be programmed or configured to maintain or vary the temperature or temperature range of the static heating zones. For example, the first heat control unit is configured to maintain the first static heating zone at a first temperature or within in a first temperature range. The second heat control unit can be configured to maintain the first static heating zone at a second temperature or within in a second temperature range. The first temperature can be higher than the second temperature, or vice versa. The first temperature range can be higher than second temperature range, or vice versa. The first temperature range can be configured so as not to overlap with the second temperature range. The first temperature or temperature range, or the second temperature or temperature range, can be less than 1° C., from about 1° C. to about 1,000° C., from about 5° C. to about 500° C., from about 10° C. to about 150° C., from about 25° C. to about 125° C., from about 40° C. to about 115° C., from about 45° C. to about 75° C. from about 50° C. to about 105° C., from about 55° C. to about 100° C., from about 60° C. to about 98° C., from about 65° C. to about 95° C., from about 70° C. to about 94° C., from about 75° C. to about 80° C. to about 92° C., from about 85° C. to about 100° C., from about 88 to about 94° C., or greater than 1,000° C. The first temperature or temperature range can differ from the second temperature or temperature range by less than about 5° C., from about 5° C. to about 50° C., from about 10° C. to about 30° C., from about 15° C. to about 25° C., or more than about 50° C. The first temperature or temperature range, or the second temperature or temperature range, can be a temperature or temperature range sufficient to allow for denaturing of double-stranded nucleic acid, annealing of nucleic acids, or extension of nucleic acids, or any combination thereof.

Accordingly, first heat control units 336 and 364, along with their respective first static heating zones 324 and 352, are generally adaptable and configured to supply a temperature or temperature range or ranges capable of denaturing double-stranded nucleic acid such as DNA. The denaturing temperature range can be from about 80° C. to about 120° C., from about 85° C. to about 115° C., from about 90° C.

to about 105° C., from about 92° C. to about 100° C., or about 94° C. Second heat control units 340 and 368 are adapted and configured to control their respective second static heating zones 328 and 356 to a temperature or temperature range or temperature ranges serving to anneal and allow for extension of single-stranded nucleic acid. The temperature setting for the second static heating zones 328 and 356 can be from about 40° C. to about 80° C., from about 50° C. to about 75° C., from about 55° C. to about 70° C., from about 58° C. to about 64° C. or about 62° C. Negative loads 344 and 372 are configurable to supply a negative temperature force to their respective static heating zones 328 and 356 to force a temperature or temperature range below that set for the respective static heating zones. Second heat control units 340 and 368 then orchestrate a temperature heat application through the respective second static heating zones to achieve a set temperature or temperature range for the respective second static heating zones.

A thermocycling plate is provided in accordance with the present teachings, which can be used in conjunction with the heating subassembly in a thermocycling subsystem. The thermocycling plate is particularly advantageous for performing polymerase chain reactions (PCR). The thermocycling plate can generally comprise a slab housing and a main fluid passage passageway that passes through the slab housing. The slab housing can be configured to have any suitable geometry. For example, the slab housing can have a width, a length, and a thickness less than both the width and the length. The slab housing can have a plurality of corners comprising a first corner, a second corner, a third corner, and a fourth corner, as well as a plurality of edges comprising a first edge extending from the first corner to the second corner, a second edge extending from the second corner to the third corner, a third edge extending from the third corner to the fourth corner, and a fourth edge extending from the fourth corner to the first corner. A plurality of partitions can be provided in slab housing. For example, the partitions can extend across the width and comprise a first partition proximal the first edge, a second partition between the first partition and a third partition, and the third partition proximal the third edge. The thermocycling plate can further comprise a first face bounded by the plurality of edges and plurality of corners; and a second face parallel to the first face; bounded by the plurality of edges and plurality of corners. The inlet, the outlet, or both can be located on the first face or the second face. The inlet, the outlet, or both can be located at the first corner, the second corner, the third corner, or fourth corner. The inlet, the outlet, or both can be located along the first edge, the second edge, the third edge, or the fourth edge.

The main fluid passageway is disposed in the slab housing and can include an inlet, an outlet, and various fluid passage segments in fluid communication with adjoining fluid passages. For example, the main fluid passageway can be constructed to provide an inlet proximal a first corner. An initial fluid passage in fluid communication with the inlet can extend to proximal the second corner along the width of the slab housing, between the first partition and the second partition. A transition fluid passage in fluid communication with the initial fluid passage can extend from proximal the second corner to proximal the third corner along the length of the slab housing. A main fluid passage in fluid communication with the transition fluid passage can extend from proximal the third corner to proximal the fourth corner along the width of the slab housing, and between the second partition and the third partition. The main fluid passage, the initial fluid passage, or both can have a tortuous shape. The shape can be winding, twisting, curvy, circuitous, serpentine, zigzag, meandering, crooked, labyrinthine, undulating, twisted, tangled, interweaved, or convoluted. The main fluid passage, the initial fluid passage, or both can have a plurality of cycles between their respective partitions. An outlet is provided in fluid communication with the main fluid passage. The inlet or outlet can be configured to have any suitable form. For example, the inlet or outlet can comprise an extension adapted to accept plastic tubing. The plastic tubing can be wholly external to the thermocycling device, pass through the fluid passageway partially, or completely pass though the fluid passageway. The fluid passageway can comprise an exit fluid passage in fluid communication with the main fluid passage and extending from proximal the fourth corner to proximal the first corner along the length of the slab housing, with the outlet is proximal the first corner in fluid communication with the exit fluid passage. In an embodiment, the main fluid passage, the initial fluid passage, or both are disposed at the first face of the sample reaction plate.

The spacing and arrangement of the transition and main fluid passage in the thermocycling plate can be defined, in part, by partitions or areas generally devoid of fluid passageways. The second partition can be parallel to, or displaced at an oblique angle relative to, at least one of the first partition and the third partition. Between various embodiments, the distance between the first and second, second and third, or first and third partitions can be varied. For example, the distance between the second and third partitions can be greater than the distance between the first and second partitions. Such a configuration allows for the main fluid passage to encompass a greater area, and volume, of the thermocycling plate, relative to the initial fluid passage. The distance between the second and third partitions can be less than two times greater, from about two times greater to about 200 times greater, from about five times greater to about 150 times greater, from about 10 times greater to about 100 times greater, from about 25 times greater to about 75 times, or more than 200 times greater than the distance between the first and second partitions. The volume or length of the main fluid passage relative to the initial fluid passage can be similarly varied.

When the initial fluid passage has a tortuous shape, it can comprise a plurality of cycles between the first partition and the second partition. A plurality of initial straight members, and a plurality of initial turn members joining the initial straight members at the first and second partitions can be provided. The main fluid passage can comprise a plurality of main straight members, and a plurality of main turn members joining the main straight members at the second and third partitions. Individual main straight members can have any length relative to the individual initial straight members, but are generally longer than the latter. Individual main straight members can have a length less than two times greater, from about two times greater to about 200 times greater, from about five times greater to about 150 times greater, from about 10 times greater to about 100 times greater, from about 25 times greater to about 75 times, or more than 200 times greater than the individual initial straight members. “Straight” members are so named to distinguished them from turn members, however, the straight members need not be completely straight nor do the turn members need to be curved. Straight members, turn members, or both can be curvilinear, rectilinear, or both. The back and forth path of the fluid passageway can act as a counter-flow heat exchanger to improve thermal stability.

The main fluid passage, the initial fluid passage, or both can comprise any number of cycles between their respective partitions or otherwise suitably orientated. For example, the main fluid passage can comprise fewer than 2 cycles, from about 2 cycles to about 2,000 cycles, from about 5 cycles to about 500 cycles, from about 10 cycles to about 100 cycles, from about 15 cycles to about 75 cycles, from about 25 cycles to about 50 cycles, about 88 cycles, or greater than 2,000 cycles between the second partition and the third partition. The initial fluid passage can comprise fewer than 2 cycles, from about 2 cycles to about 200 cycles, from about 5 cycles to about 150 cycles, from about 10 cycles to about 100 cycles, from about 15 cycles to about 75 cycles, from about 25 cycles to about 50 cycles, about 40 cycles, or greater than 200 cycles between the first partition and the second partition. The number of cycles can correspond to the number of paths of the fluid passageway, in particular, the main fluid passage, through the temperature zones.

Figure 8C:
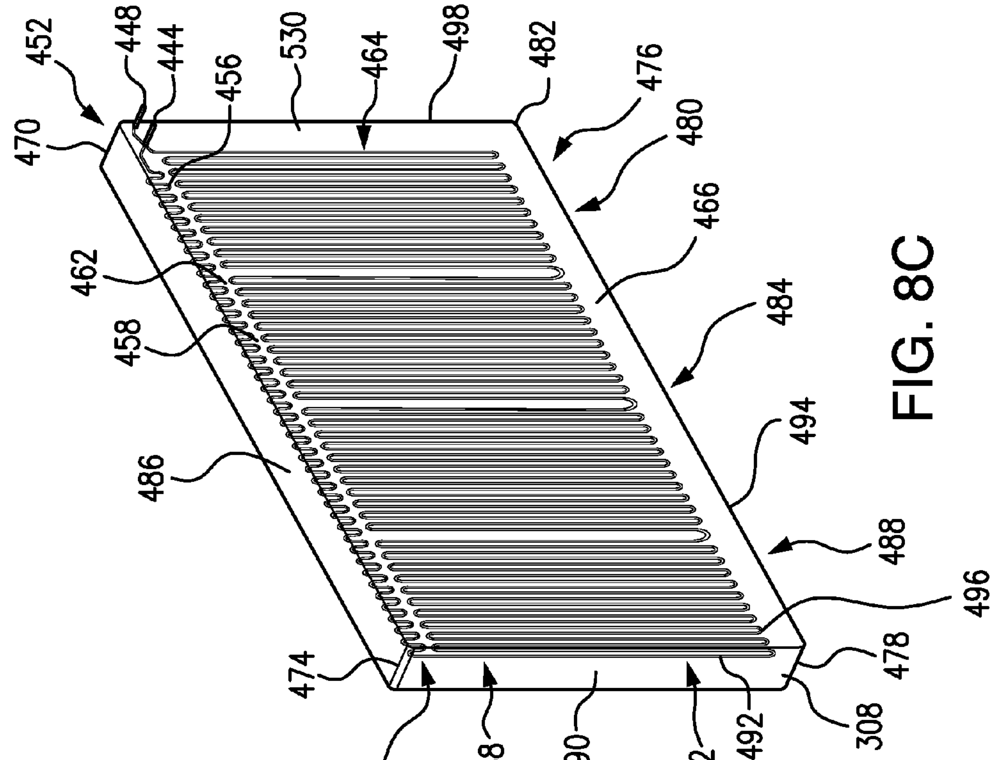
FIG. 8C is a perspective view and mirror image of the thermocycling plate shown in FIG. 8A.
Figure 8A:
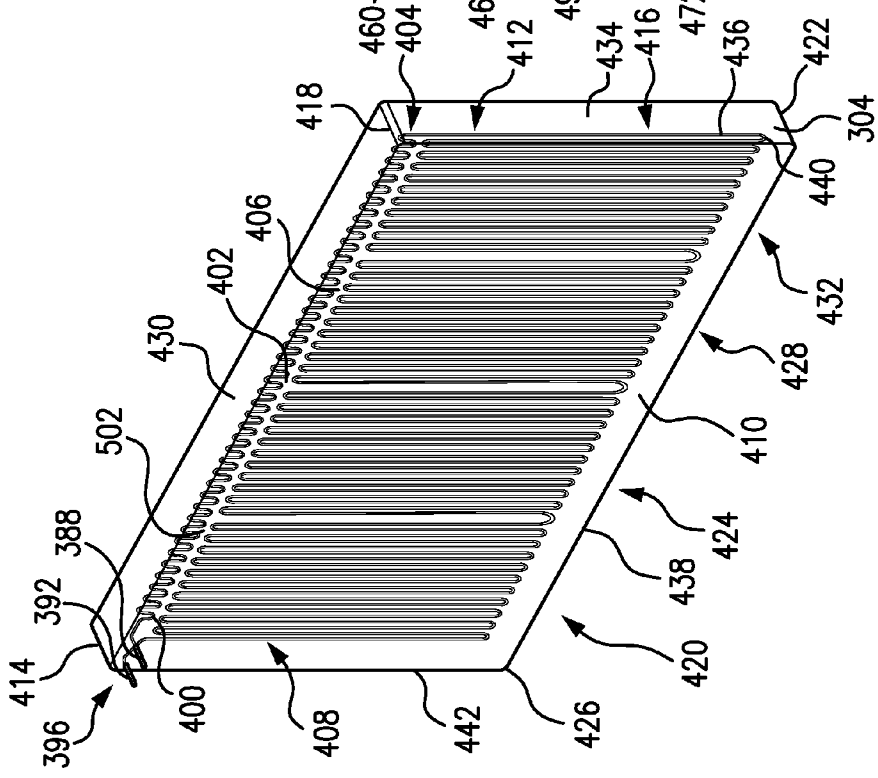
FIG. 8A is a perspective view of a thermocycling plate for use in a thermocycling subsystem in accordance with various embodiments of the present teachings.
Figure 8D:
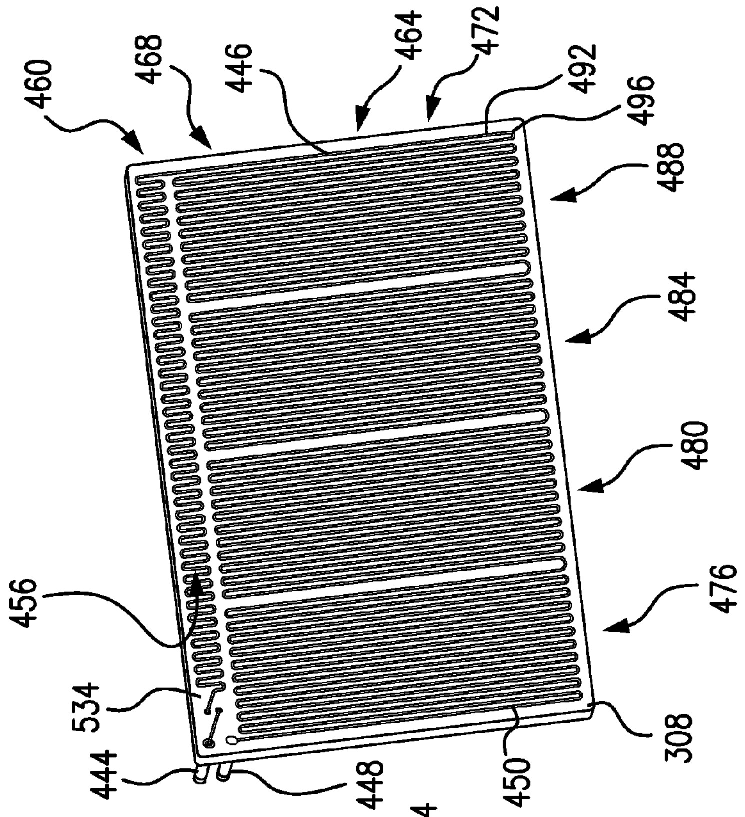
FIG. 8D is a rear perspective view of the thermocycling plate shown in FIG. 8C in accordance with various embodiments of the present teachings.
Figure 8B:
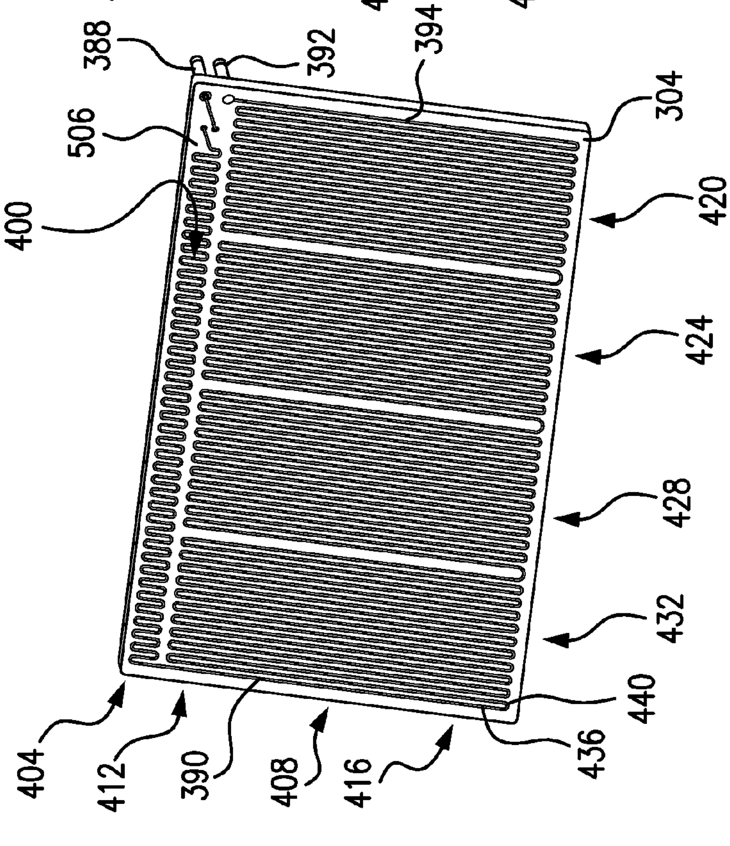
FIG. 8B is a rear perspective view of the thermocycling plate shown in FIG. 8A.

In accordance with the present teachings, FIG. 8A shows a front perspective view of a first thermocycling plate 304, and FIG. 8B is a rear perspective view of the same plate. In FIG. 8C is shown a second thermocycling plate 308, which is a mirror image of thermocycling plate 304, with the rear perspective view shown in FIG. 8D. The first thermocycling plate can have a plurality of corners, for example, four corners, 414, 418, 422, 426, bounding a plurality of edges, for example, four edges, 430, 434, 438, and 442. These corners and edges can define a first face 502 and a second face 506. First, second, and third partitions, 402, 406, and 410 are also provided.

In FIG. 8A, an inlet 388 and an outlet 392 are shown in fluid connection within a first thermocycling plate 304. A fluid passageway 396 is constructed through first thermocycling plate 304 in a generally serpentine fashion in the form of a fluid passageway 396. Fluid passageway 396 begins at inlet 388 and proceeds into an initial loop sector 400. The initial loop sector 400 falls within a hot start region 404 that corresponds to the upper portion of the first static heating zone 324 of first heating block 312. Fluid passageway 396 then enters into a main cycling loop area 408, which corresponds to most of the fluid passageway 396 in first thermocycling plate 304. The upper part of the main cycling loop region 408 falls within a denaturing region 412. Denaturing region 412, along with hot start region 404, both line up and correspond to first static heating zone 324 of first heating block 312. The lower part of main cycling loops 408 corresponds to and is alignable with second static heating zone 328 of first heating block 312. Main cycling loop region 408 can be segmented into a plurality of main sectors. For example, in FIG. 8A, main cycling loop region 408 is divided into a first main sector 420, a second main sector 424, a third main sector 428, and a fourth main sector 432. An examination of the main cycling loop region 408 shows that the fluid passageway 396 comprises both straight members 436 and turn members 440. An analogous configuration also can apply to initial loop sector 400.

Second (complementary) thermocycling plate 308, shown in FIG. 8C, has analogous components to first thermocycling plate 304. The second thermocycling plate can have a plurality of corners, for example, four corners, 470, 474, 478, 482, bounding a plurality of edges, for example, four edges, 486, 490, 494, and 498. These corners and edges can define a first face 530 and a second face 534. First, second, and third partitions, 458, 462, and 466 are also provided. There are inlet 444, outlet 448, and fluid passageway 452. An initial loop sector 456 is provided that is situated in a hot start region 460. Fluid passageway 452 is next situated in the form of main cycling loop region 464 which corresponds to both a denaturing region 468 and its upper part and a annealing/extension region 472 in its lower part. As an example, main cycling loop region 464 is shown divided into first, second, third, and fourth main sectors 476, 480, 484, and 488. As was the case with fluid passageway 396, fluid passage 452 comprises both straight members 492 and turn members, or curved members, 496. FIGS. 8B and 8D show reverse perspective views of the thermocycling plates 304 and 308 shown in FIGS. 8A and 8C, respectively. When two or more thermocycling plates are employed, their respective fluid pathways can be joined to increase the total length of fluid pathway as well the number of cycles achievable when performing a thermocycling method such as PCR.

Figure 24A:
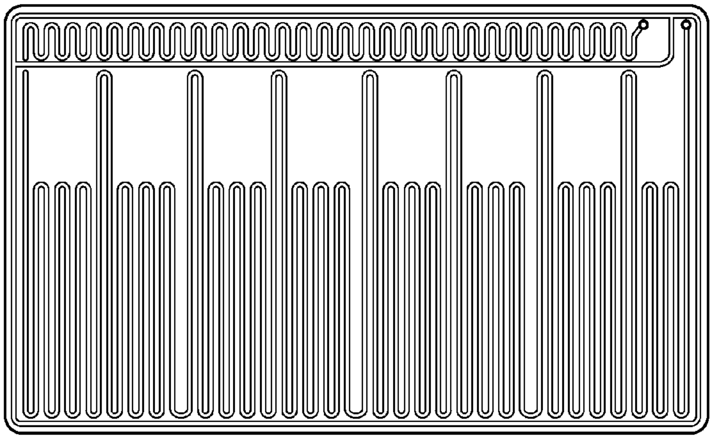
Figure 24B:
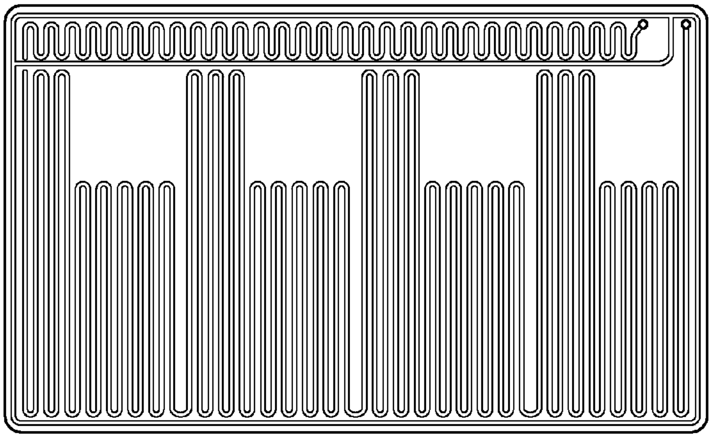
Figure 24C:
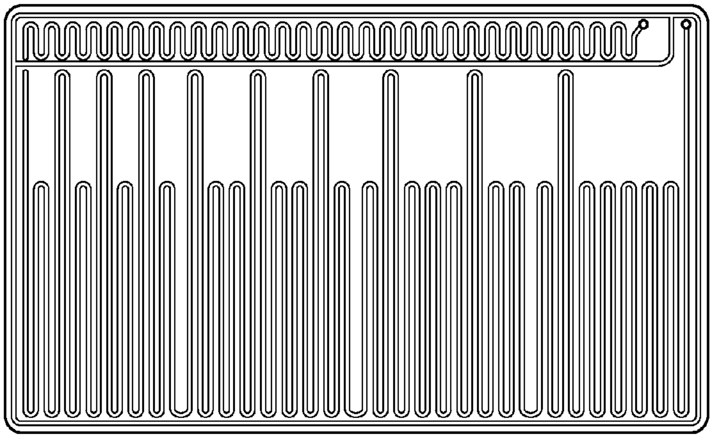
Figure 25:
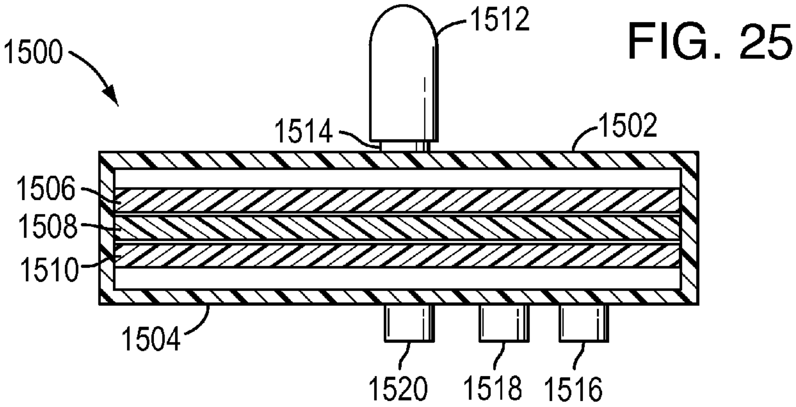
FIG. 25, FIG. 26, FIG. 27, FIG. 28, FIG. 29, FIG. 30, and FIG. 31 include illustrations of exemplary emulsion-generating devices.
Figure 26:
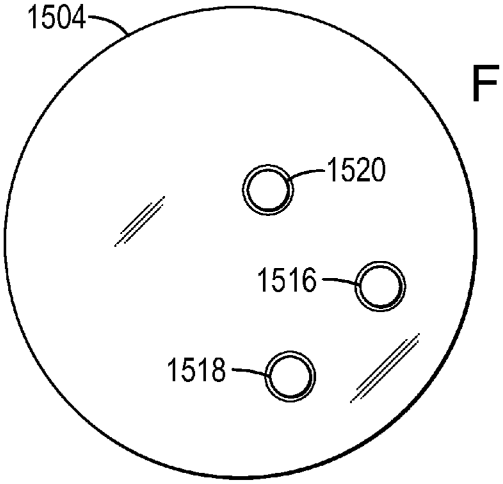
Figure 27:
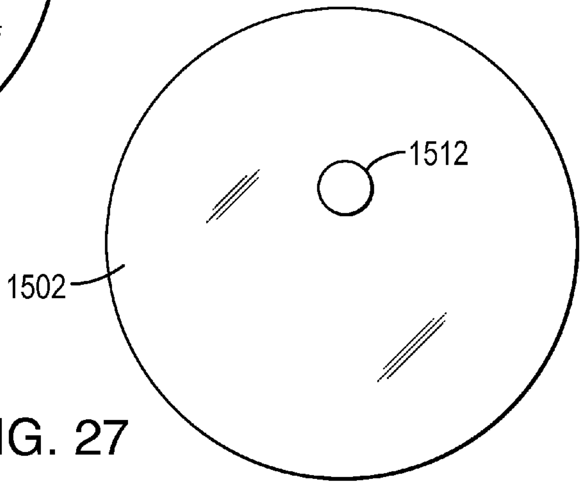
Figure 28:
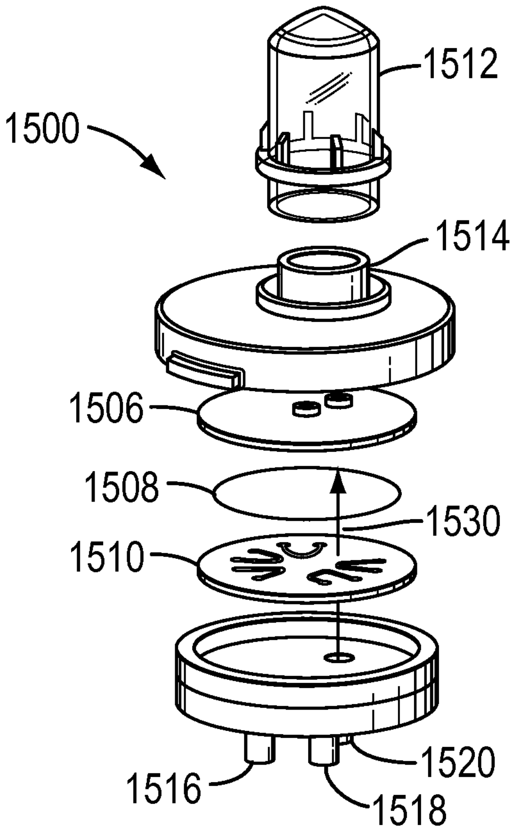
Figure 29:
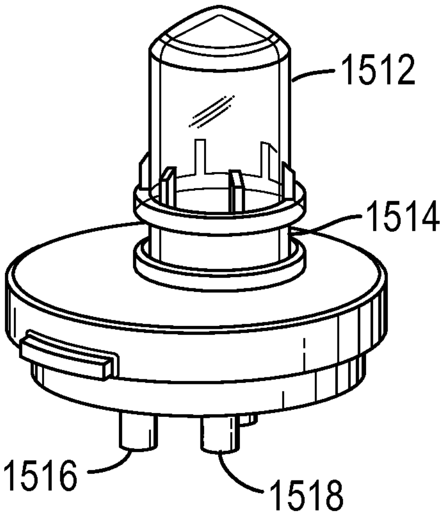
Figure 30:
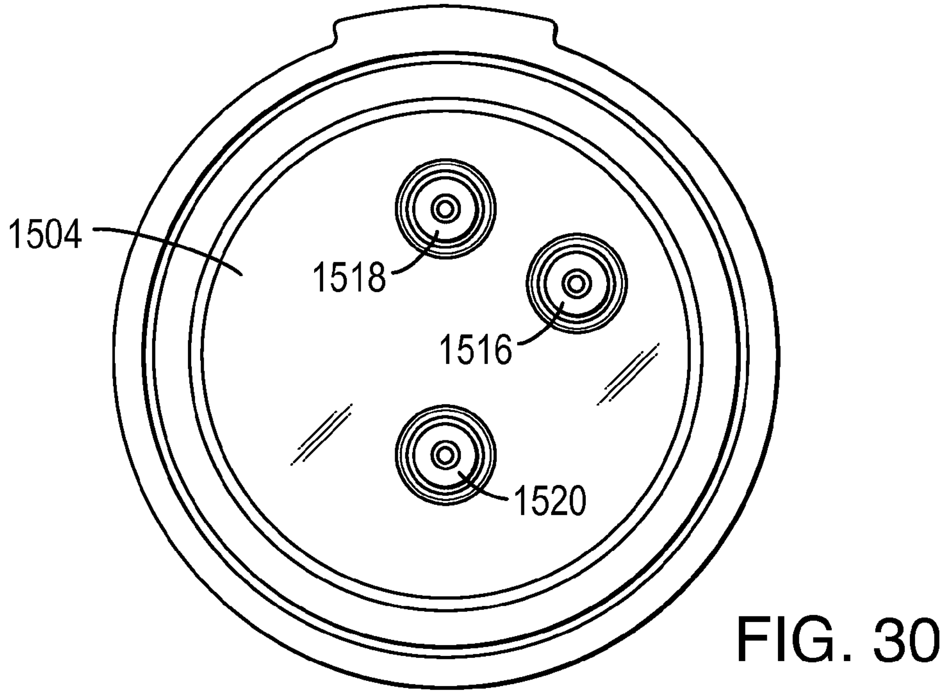
Figure 31:
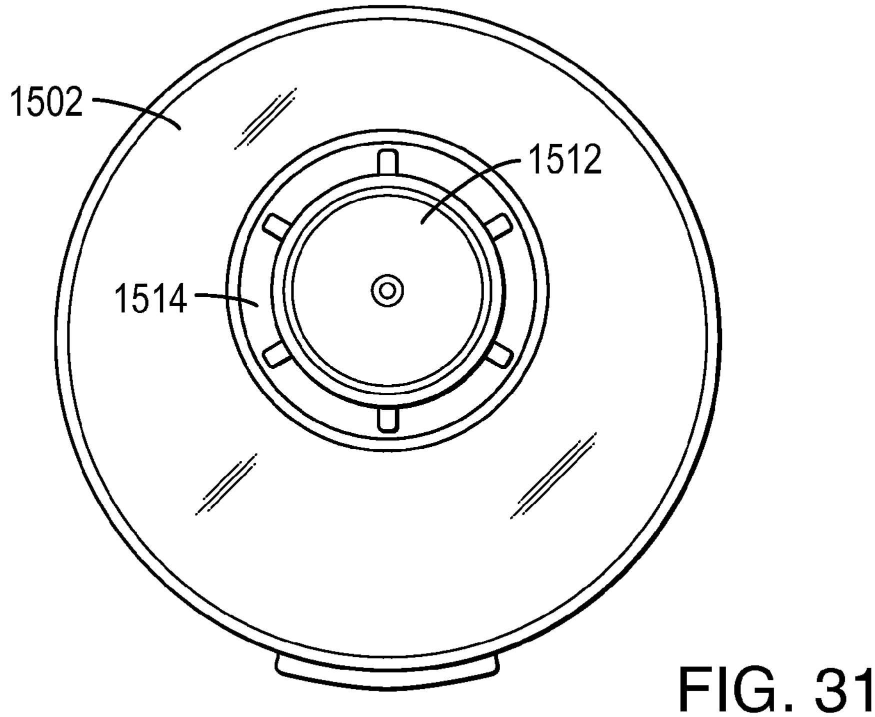

Thermocycling plates having different number and configuration of sectors can be selected. For example, a thermocycling plate having a different number of main sectors can be selected. In another example, the number or length of straight members within sectors can be varied to achieve desired enhancement or sequencing performance. As illustrated in FIGS. 24A-24F, the length of straight members can be varied within sectors or between sectors. For example, some straight sections within a sector can be shorter, while other straight members can extend to the full extent of the sector. As illustrated in FIG. 24D, some sectors can have long straight members, while other sectors within the thermocycling plate can have short straight members. As illustrated in FIG. 24B, the long straight members within a sector can be adjacent one another, while the short straight members within the sector can be adjacent one another. Alternatively, the longer straight members can be separated by short straight members, as illustrated in FIG. 24A or FIG. 24C.

Each of the illustrated plates can be used as either a first or second thermocycling plate. In a particular example, the thermocycling plate illustrated in FIG. 24E can be used as a first thermocycling plate, while the plate illustrated in FIG. 24F can be used as a second thermocycling plate.

Figure 34:
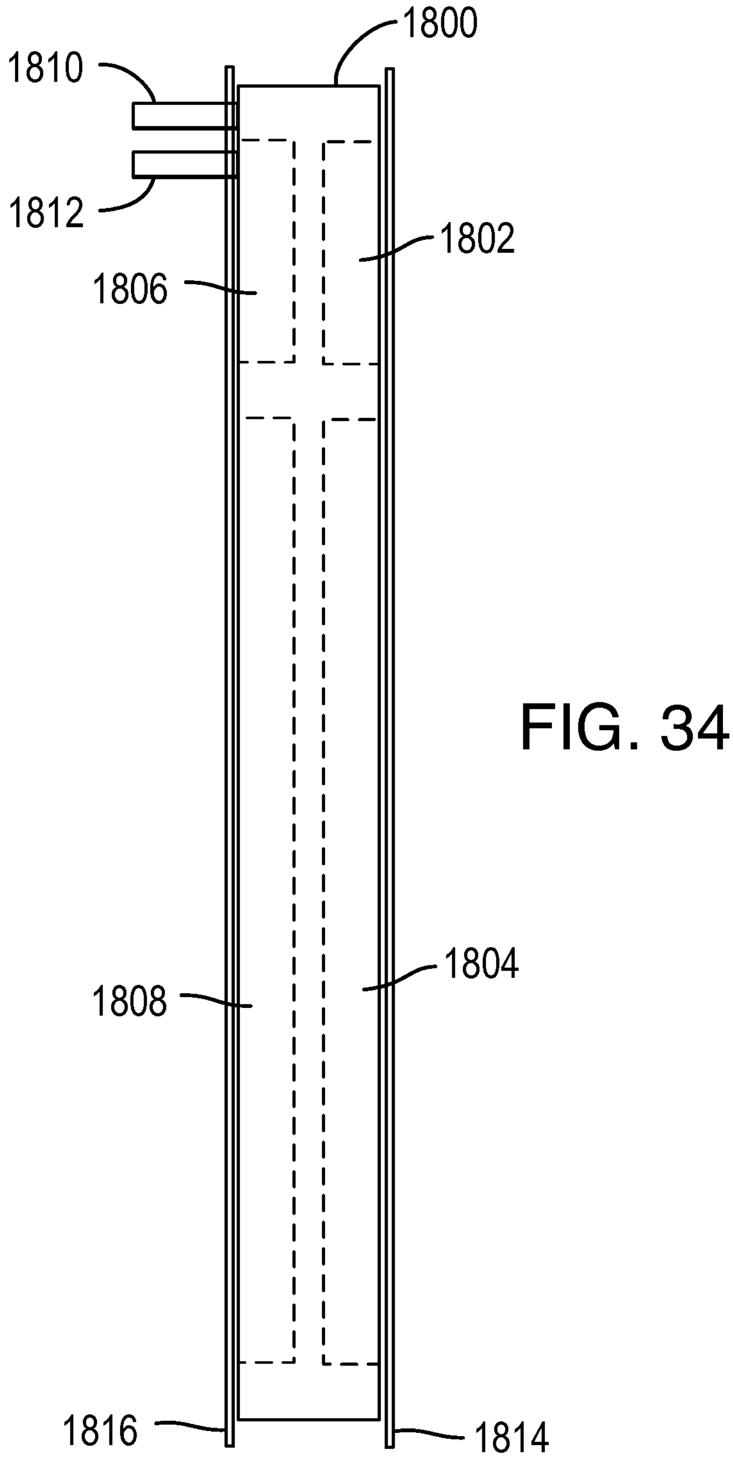
FIG. 34 and FIG. 35 include illustrations of exemplary thermocycling plates.
Figure 35:
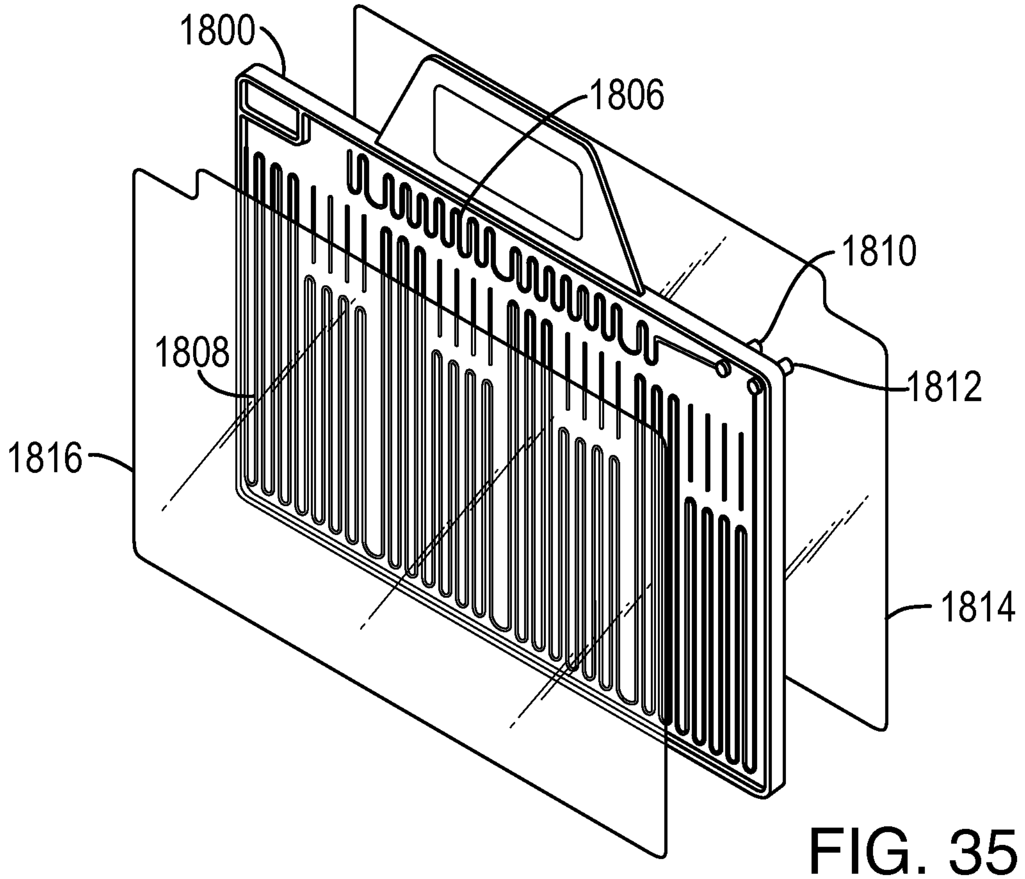

In an alternative example, a single thermocycling plate can include fluid passageways molded into both sides of the plate. Flat faceplates can be applied on either side of the double-sided thermocycling plate to define the fluid passageways on both sides of the thermocycling plate. Alternatively, films can be applied to both sides of the thermocycling plate to complete the formation of the fluid passageways. For example, as illustrated in FIG. 34 and FIG. 35, a single thermocycling plate 1800, illustrated in cross-section, includes molded channels 1802, 1804, 1806, and 1808 disposed on either side of the thermocycling plate 1800. When films 1814 and 1816 are attached to opposite sides of the thermocycling plate 1800, fluid passageways are defined.

In a particular example, and input port 1810 receives fluid, and directs the fluid on one side of the thermocycling plate 1800. After traversing both sides of the thermocycling plate 1800, the emulsion can exits port 1812. In a particular example, the design the fluid passageways molded within each side of the thermocycling plate 1800 can comply with one or more features of the above-described thermocycling fluid passageways.

The thin films 1814 or 1816 disposed on opposite sides of the thermocycling plate 1800 can be formed of thin films having one or more layers. In an example, the thin-film can include polymeric materials, such as polyolefins, polyesters, fluoropolymers, silicone, polyimide, polyamide, polycarbonate, or any combination thereof. In another example, the thin-film can be formed of metallic material such as aluminum. In a further embodiment, the film can include more than one layer such as layers of polyolefin, polyester, and aluminum. The films 1814 and 1816 can be flexible. Further, such films 1814 and 1816 can have a thickness in a range of 5 μm to 1000 μm, such as a range of 5 μm to 100 μm, a range of 5 μm to 50 μm, or even a range of 10 μm to 25 μm. Alternatively, the films 1814 or 1816 can be replaced with metallic or plastic sheets having a thickness greater than 1000 μm. The films 1814 or 1816 can be secured to the thermocycling plate 1800 by a heat bond. Alternatively, an adhesive can be utilized to secure the films 1814 and 1816 to the thermocycling plate 1800.

The cross-sectional area of the fluid passageway of the thermocycling plate can be constant, variable, or both, throughout its length or in within particular segments or regions. Cross-sectional area can be varied for any suitable objective such as heat transfer or fluid velocity. The present teachings have found that decreasing the cross-sectional area in turn members relative to adjacent straight members can increase the local velocity of the fluid passing through the fluid passageway and prevent or alleviate accumulation or queuing of particles or other bodies, for example, aqueous reactor droplets in an a water-in-oil emulsion. The turn members so configured can be those members located along that partition that lies closer to the bottom of the thermocycling plate, depending how the plate is orientated, for example, if the third partition is at the bottom (generally the case) or if the first partition is at the bottom. If the second edge or fourth edge of the thermocycling plate is at the bottom, the straight members can be configured to have a cross-sectional area less than that of the turn members.

At least one initial turn member or main turn member can have an average cross-section area less than an average cross-section area of an adjacent initial straight member or adjacent main straight member. A plurality of the initial turn members along the second partition can each have an average cross-sectional area less than the average cross-sectional area of an adjacent initial straight member. A plurality of the main turn members along the third partition can each have an average cross-sectional area less than the average cross-sectional area of an adjacent initial straight member. A plurality of the initial turn members along the first partition can each have an average cross-sectional area less than the average cross-sectional area of an adjacent initial straight member. A plurality of the main turn members along the second partition each have an average cross-sectional area less than the average cross-sectional area of an adjacent initial straight member. Changes in cross-sectional area can be achieved abruptly or gradually, for example, by way of tapering the fluid passageway. The cross-section can comprise one or more shapes. Examples of shapes include circles, ellipses, squares, rectangles, and the like. The number and length of straight elements in the fluid passageway can be determined by a person skilled in the art based on parameters such as the desired number of reaction cycles and the fluid velocities.

Figure 9B:
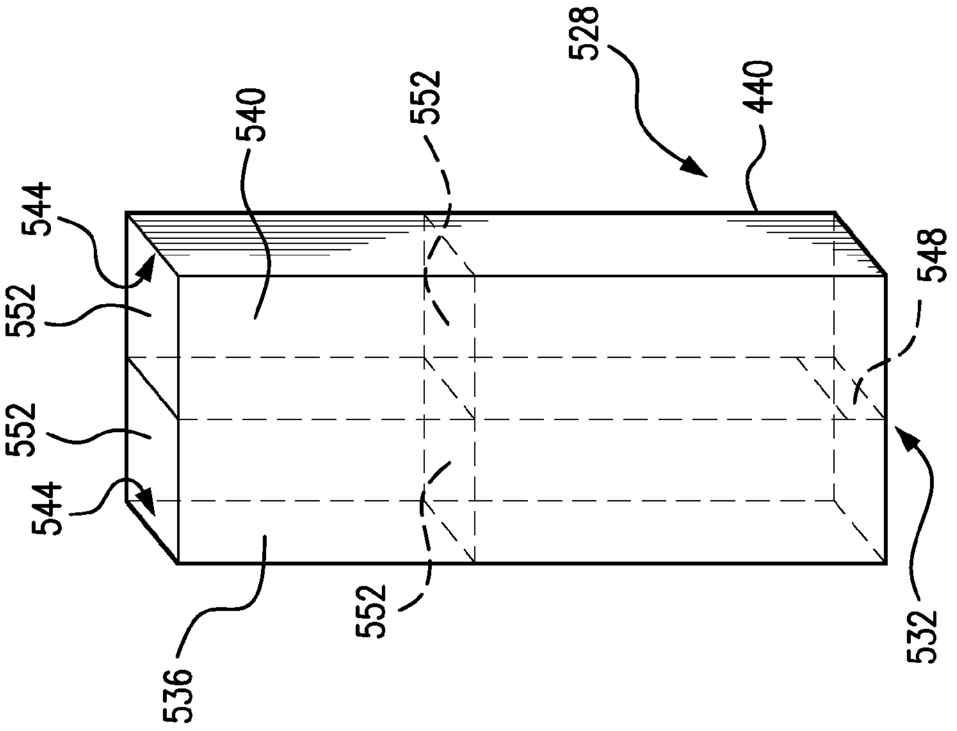
FIG. 9B is a perspective view of another bottom portion of a fluid passage that can be found in a thermocycling plate in accordance with various embodiments of the present teachings.
Figure 9A:
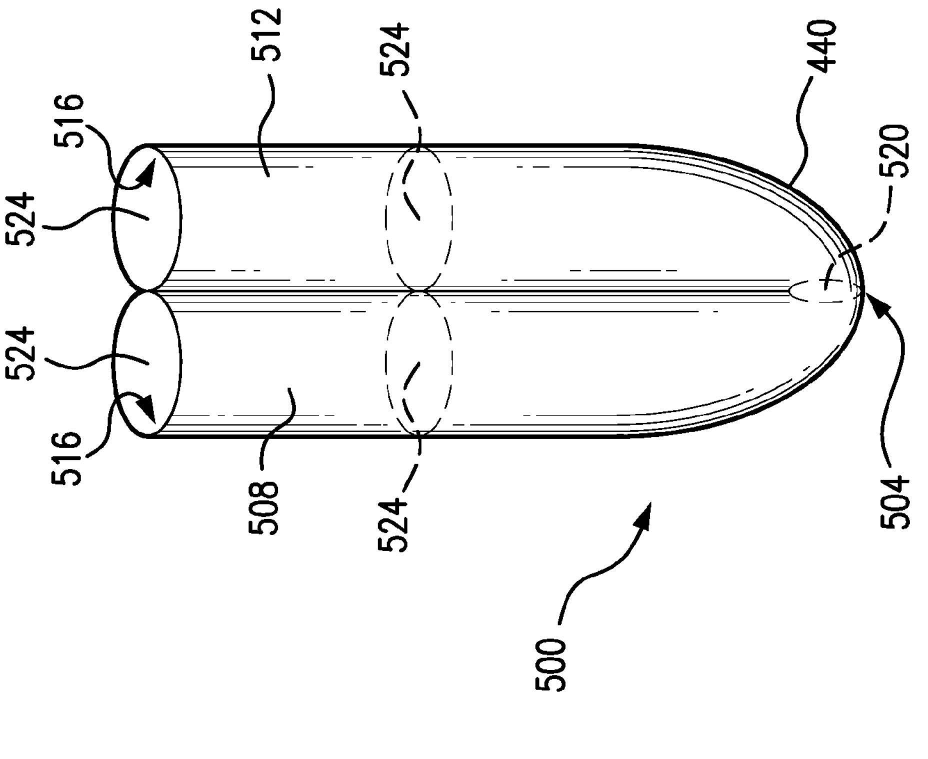
FIG. 9A is a perspective view of a bottom region of a fluid passage found in a thermocycling plate in accordance with various embodiments of the present teachings.

FIGS. 9A and 9B show two embodiments focusing on the straight members 436 and 492 as well as turn members 440 and 496. In FIG. 9A, a bottom region 500 is shown that could correspond to a bottom region found in either the main cycling loop region 408 or the initial loop sector 400. Bottom region 500 has a midpoint 504. Adjacent first straight member 508 and second straight member 512 define in part the main passage 516 of the fluid passageway 396. Midpoint cross-section 520 at midpoint 504 of bottom region 500 can be figured to have a cross-sectional area which is less than that of main passage cross-sectional area 524. By having the midpoint cross-sectional area less than the main passage cross-sectional area, the flow at midpoint 504 and adjacent regions is increased relative to the flow in main passage 516. An increase in flow at bottom region 500 is desirable as a counter to gravity and the tendency of microreactor liquid aqueous droplets in the water-in-oil emulsion that passes through fluid passageway 396 to accumulate at bottom regions. FIG. 9B shows an alternative embodiment bottom region 528 that employs a rectilinear cross-sectional design as opposed to the curvilinear cross-sectional design of bottom region 500. Again, the cross-sectional area of the main passage, here 552, is greater than the midpoint cross-sectional area, here 548, at midpoint 532 in order to achieve a desirable increase in flow. First straight member 536 and second straight member 540 correspond to the analogous members 508 and 512 shown in FIG. 9A, as does main passage 544 to main passage 516.

The thermocycling plates of the present teachings can be constructed from any material or combination of materials. Examples of suitable materials include plastics, glass, ceramics, metals, and the like. Examples of suitable plastics can include one or more of polypropylene, polycarbonate, polyimide, silicone, fluoropolymer, polyamide, polyvinylchloride, or any combination thereof. The thermocycling plate can be of any shape. The plate can be transparent, translucent, or opaque, or any combination thereof. The thermocycling plates can be manufactured using any method. For example, the slab housing can be made us of two complementary panels, each supplying one of the two respective faces of the slab housing, which are joined together with the faces facing outwards. The thermocycling plates can also be constructed as described in U.S. Patent Application Publication No. US 2008/0280331 A1. The present teachings also include pairs or sets of the thermocycling plates. In a given pair or set, the individual thermocycling plates can include identical plates, non-identical plates, or both. For example, a pair or set of plates can include thermocycling plates of the invention that are mirror images of one another. Plates can be configured for fluid connection with one another.

The thermocycling plates can be provided with any suitable dimensions. For example, the thermocycling plate can be slightly larger than a standard 96-well plate. The average diameter of the fluid passageway can be less than about two times, from about two times to about 2,000 times, from about 5 times to about 1,500 times, from about 10 times to about 1,000 times, from about 50 times to about 500 times, from about 100 times to about 250 times, or greater than 2,000 times the diameter of aqueous reactor droplets in a water-in-oil emulsion.

The thermocycling subsystem can be insulated using any means or mechanism. For example, a gasket can be used for insulating purposes. The gasket can be adjacent to at least three sides of each of the first thermocycling plate and the first heating block. The gasket can be adjacent to at least three sides of each of the first thermocycling plate, the second thermocycling plate, the first heating block, and the complementary heating block. The gasket can be constructed using any suitable material or materials, for example, a rubber. The gasket can comprise a compliant membrane.

Figure 10A:
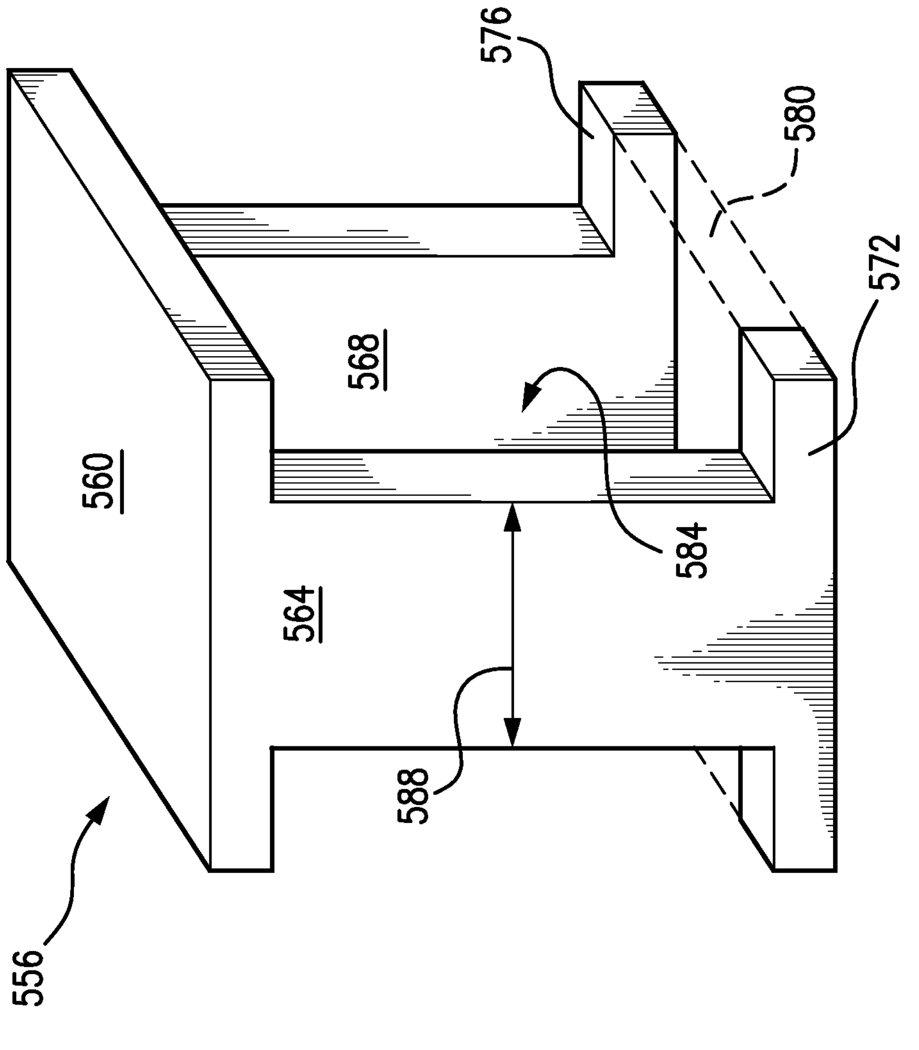
FIG. 10A is a perspective view of a gasket that can be used in combination with a thermocycling subsystem in accordance with various embodiments of the present teachings.

FIG. 10A shows a gasket in accordance with the present teachings. Gasket 556 can comprise a top section 560, a first lateral section 564, and a second lateral section 568. First and second lateral sections 564 and 568 can comprise, respectively, first lateral base 572 and second lateral base 576. In a variation on the gasket 556 shown in FIG. 10A, first lateral base 572 and second lateral base 576 can be extended into an optional bottom section 580 analogous to top section 560. Top section 560, lateral first and second lateral sections 564 and 568, and optionally bottom section 580 surround and define an aperture 584. The aperture may be configured to allow insertion of thermocycling subsystem 300 or 320. Depending on whether a first thermocycling subsystem 300 or second subsystem 320 is employed, lateral width 588 of gasket 556 can be varied. Lateral width can also be varied independent of the particular thermocycling subsystem employed.

Figure 10B:
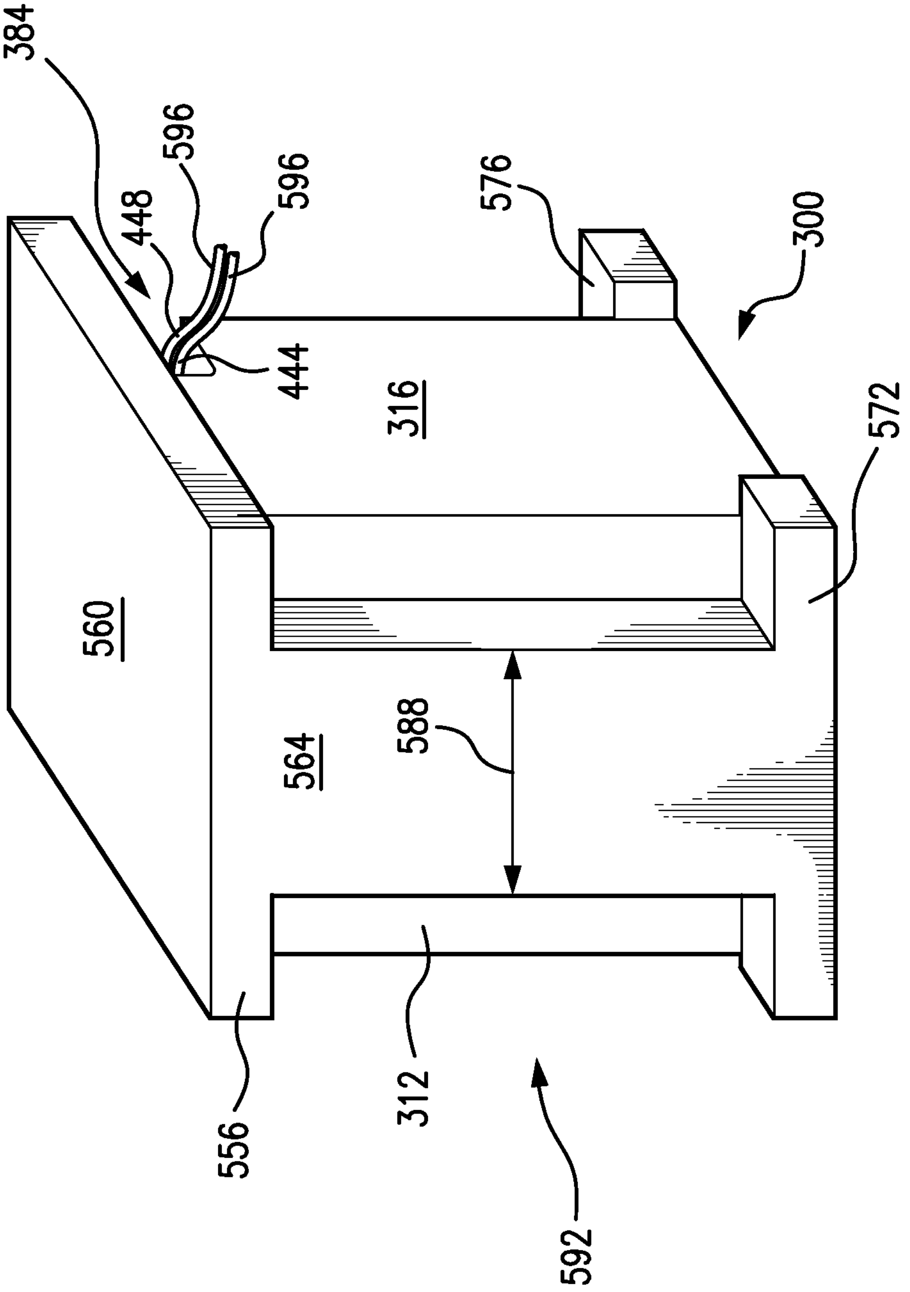
FIG. 10B is a perspective view of the gasket shown in FIG. 10A in combination with a thermocycling subsystem in accordance with various embodiments of the present teachings.

FIG. 10B shows gasket 556 with thermocycling subsystem 300 (or 320) inserted into aperture 584 of gasket 556. Resulting assembly 592 includes both gasket 556 and thermocycling subsystem 300 (or 320). Visible are both the first and second heating blocks 312 and 316, along with tubing 596 extending from inlet 444 and outlet 448 through access recess 384 of heating block 316.

Figure 11A:
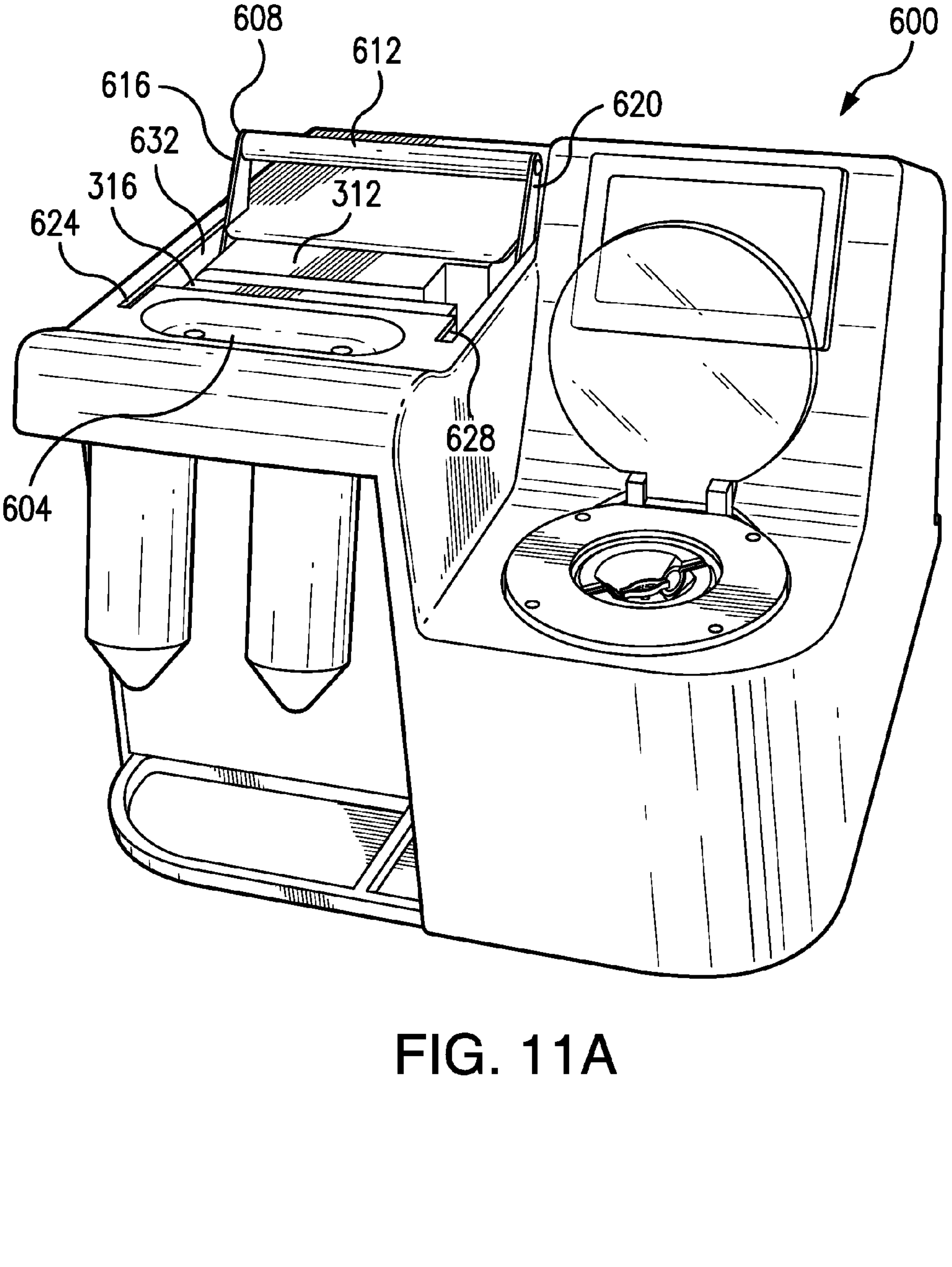
FIG. 11A is a perspective view of an emulsion PCR system showing a thermocycling subsystem in an open configuration in accordance with various embodiments of the present teachings.
Figure 11B:
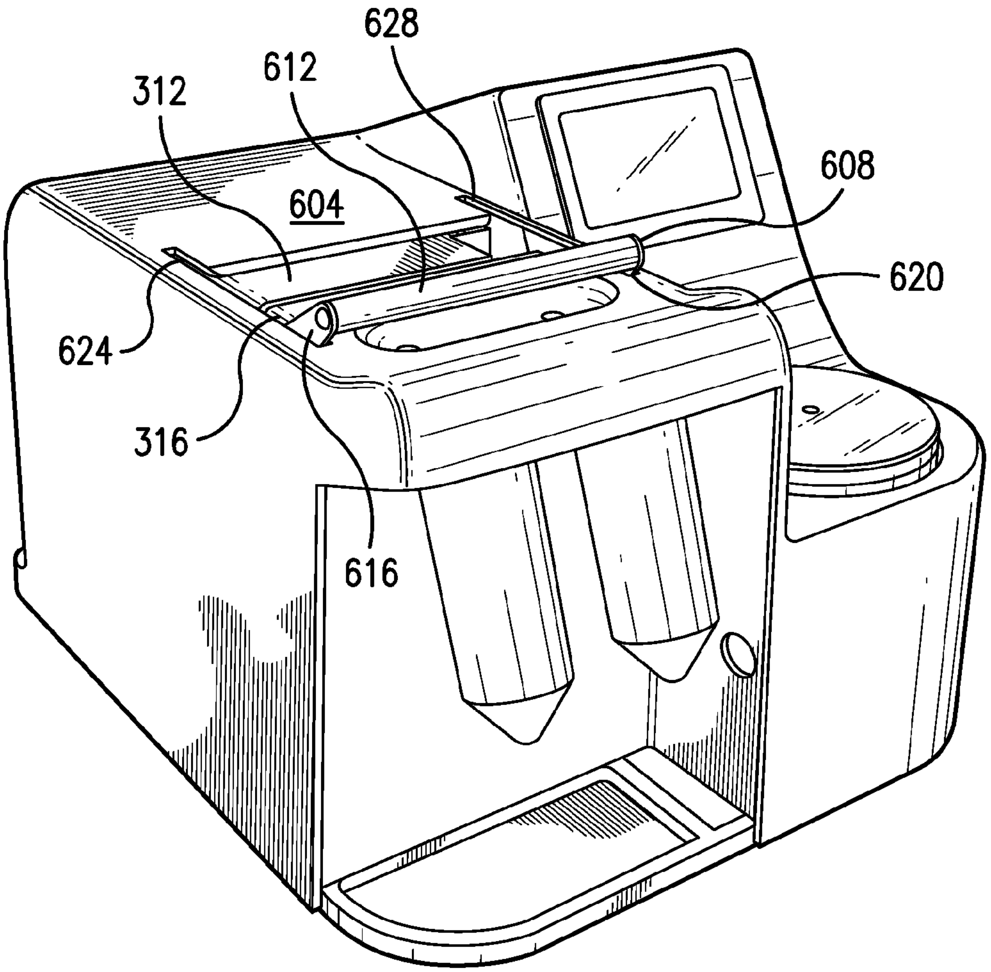
FIG. 11B is a perspective view of an emulsion PCR system showing a thermocycling subsystem in a closed configuration in accordance with various embodiments of the present teachings.

FIGS. 11A and 11B show an emulsion thermocycling system 600, including thermocycling subsystem 300 in an open and closed configuration, respectively. Such a system can be used to generate and recover a PCR product. FIG. 11A shows thermocycling subsystem 300 in an open configuration in the right perspective view of emulsion thermocycling system 600. A thermocycling system 600 has a top surface 604 residing on a housing. The opening of thermocycling subsystem 300 can be achieved by using a lever 608. Lever 608 includes a lateral handle portion 612 mounted between a first arm 616 and a second arm 620. Lever 608 is configured so that first arm 616 and second arm 620 can engage in respective first track 624 and second track 628. When lever 608 is pulled back relative to a front of the emulsion thermocycling subsystem, an opening 632 is provided between first and second heating blocks 312 and 316. FIG. 11B, showing a left perspective view of the emulsion thermocycling subsystem shown in FIG. 11A, depicts thermocycling subsystem 300 in a closed configuration. The closed configuration is achievable by pulling or pushing forward lever 608 so that first heating block 312 and second heating block 316 are brought together and immediately adjacent to each other so as to close the opening 632 that has been shown in FIG. 11A. Lever 608 can be configured and arranged in any appropriate configuration. For example, a lever mechanism as described in U.S. Pat. No. 6,896,849 B2. A latch or locking mechanism for the lever can also be incorporated into thermocycling subsystem 300 and emulsion thermocycling system 600.

In accordance with the present teachings, a method of thermocycling is provided. The method can comprise one or more of the following steps, the order of which can be varied, or one or more steps can be repeated. A source solution can be passed through a thermocycling plate comprising a plurality of regions. A hot start region corresponding to an initial fluid passage of the thermocycling plate can be heated and a denaturation region corresponding to a portion of a main fluid passage proximal a second partition of the thermocycling plate can be heated to a first temperature or temperature range. An annealing/extension region corresponding to a portion of the main fluid passage proximal a third partition of the thermocycling plate can be heated to a second temperature or temperature range. The first temperature can be higher than the second temperature, and the first temperature range can be higher than second temperature range.

The sample fluid passed through the fluid passageway can comprise a water-in-oil emulsion comprising a plurality of aqueous polymerase chain reaction (PCR) reaction droplets. Such droplets and water-in-oil emulsion can be formed using the emulsion generation techniques described herein. When using the thermocycling plate for PCR amplification, the method can comprise annealing a sample nucleic acid in the reactor droplet to a template in the reactor droplet, extending the sample nucleic acid to form a double-stranded nucleic acid, denaturing the double-stranded nucleic acid, and repeating such steps until a desired amplification can be achieved. Sample (source) fluid can be sent from the thermocycling subsystem to a centrifuge subsystem. For example, PCR product in the sample solution can be sent from the thermocycling plate outlet to a centrifuge for recovery of the PCR product. The method can also include stabilizing the thermocycling plate with an oil phase prior to passing an emulsion through the fluid passageway. The fluid can be passed through the fluid passageway at any desirable rate or acceleration. For example, the fluid can be passed through the fluid passageway at a rate of less than 0.001 mL/min, from about 0.001 mL/min to about 1 L/min, from about 0.01 mL/min to about 500 mL/min, from about 0.1 mL/min to about 250 mL/min, from about 0.25 mL/min to about 100 mL/min, from about 0.5 mL/min to about 50 mL/min, from about 1.0 mL/min to about 10 mL/min, or greater than 1 L/min. Fluid can be passed through continuously or bath-wise. Aqueous reactor droplets in the oil-phase can pass through the fluid passageway in any manner. While, such passage can comprise a single file passage, single file passage is not necessary, and simultaneous passage of more than one droplet through a given cross-section is permitted.

Centrifugation Subsystem and Emulsion Breaking

In accordance with the present teachings, a centrifuge subsystem is provided that is suitable for integration into an emulsion PCR system or equivalent device. The centrifuge can comprise a centrifuge housing, a motor comprising a rotor axle mounted in the housing motor aperture; and a rotor mounted on the rotor axle or otherwise operably connected to a spinning means. The centrifuge housing can comprise sidewalls extending from a base portion to a top portion comprising a top housing rim surrounding a top housing aperture. A lid operably associable with the top housing rim can be provided. The housing can further include a housing bottom recess extending from the base to an interior of the centrifuge housing and comprising bottom recess sidewalls and a bottom recess ceiling. A housing basin can be defined by the top housing rim, top housing aperture, and housing basin sidewalls surrounding a receiving platform. The housing can also provide a housing motor aperture configured to accept a motor through the bottom recess ceiling and receiving platform. The housing can be constructed of any suitable material or combination of materials, for example, those materials described herein for the collection tubes, slinger, and rotor. Any or all components of the centrifuge subsystem can be transparent, translucent, or opaque, or any combination thereof.

The centrifuge can be used with or without a lid. The lid can be connected to the centrifuge housing using any suitable manner. The housing or lid can be secured with threading to allow the lid to be screwed on and off the centrifuge housing. A clamp can be provided on the lid housing or centrifuge housing to allow the lid to be attached and detached from the centrifuge housing. The lid housing or centrifuge housing can be provided with a gasket or other sealing mechanism to allow for a tight fit between the lid and centrifuge sidewalls. The lid can be attached to the centrifuge housing using one or more hinges. For example, a housing hinge assembly can be employed that comprises a housing hinge plate operatively connectable to the centrifuge housing. The housing hinge plate can include a top plate portion, first and second hinge receiving arms extending from the top plate portion and comprising respective first and second hinge axle apertures. A hinge axle can extend from the first and second hinge axle apertures and passing through a lid hinge portion extending from the lid.

Figure 12A:
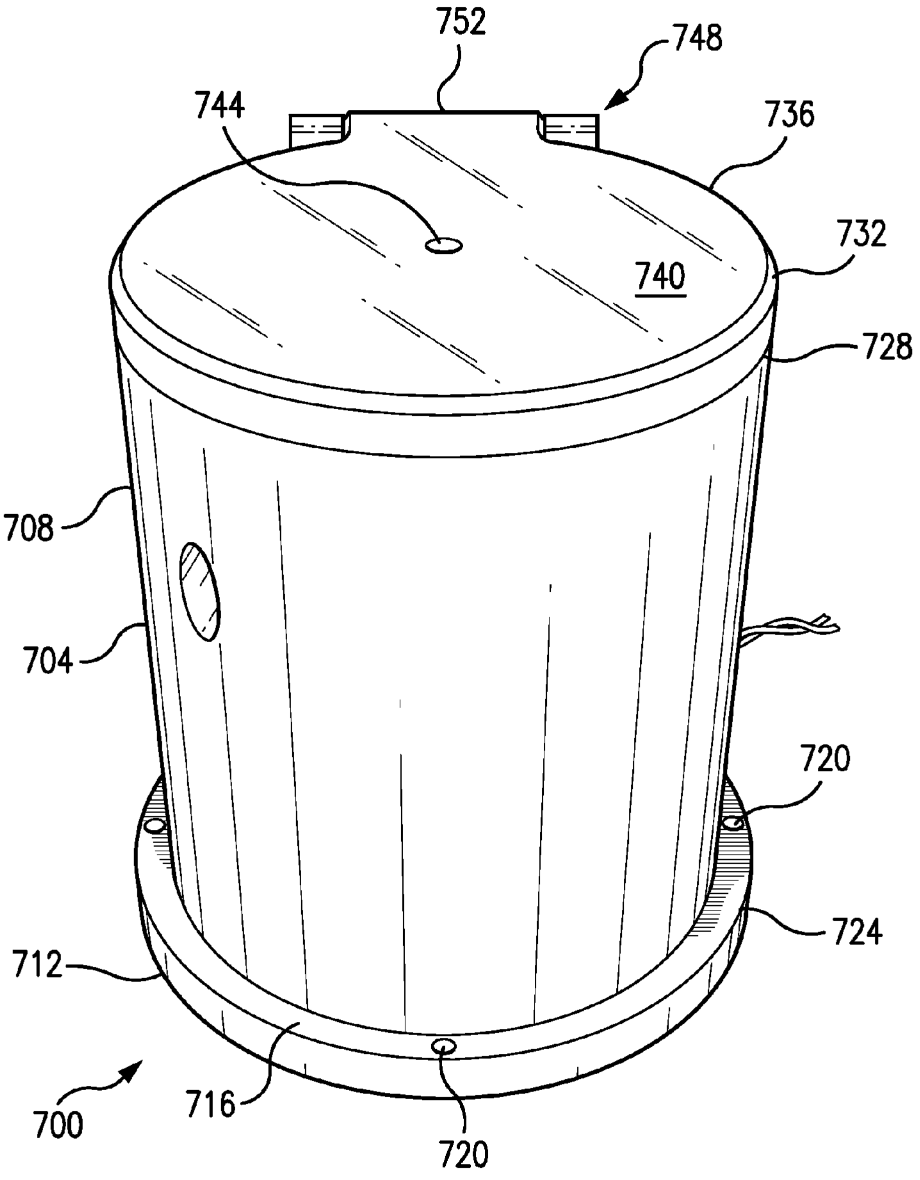
FIG. 12A is a front perspective view of a centrifuge subsystem in accordance with various embodiments with the present teachings.

FIG. 12A is a front perspective view of an embodiment in accordance with the present teachings. A centrifuge subsystem 700 comprises a centrifuge housing 704. The centrifuge housing 704 includes centrifuge housing sidewalls 708 that extend to a base portion 712. Base portion 712 can contain a flange 716 that can provide mounting apertures 720 along a flange perimeter 724. Mounting apertures 720 allow the centrifuge subsystem 700 to be mounted in an emulsion thermocycling system or the like. Top portion 728 of centrifuge housing 704 provides a foundation for a lid 732 when in a closed configuration as shown in FIG. 12A. Lid 732 is constructed with a lid housing 736 that provides a top lid surface 740 and a bottom lid surface 742 through which a central lid aperture 744 is located. Lid 732 is attached to centrifuge housing 704 through a hinge 748.

Figure 12B:
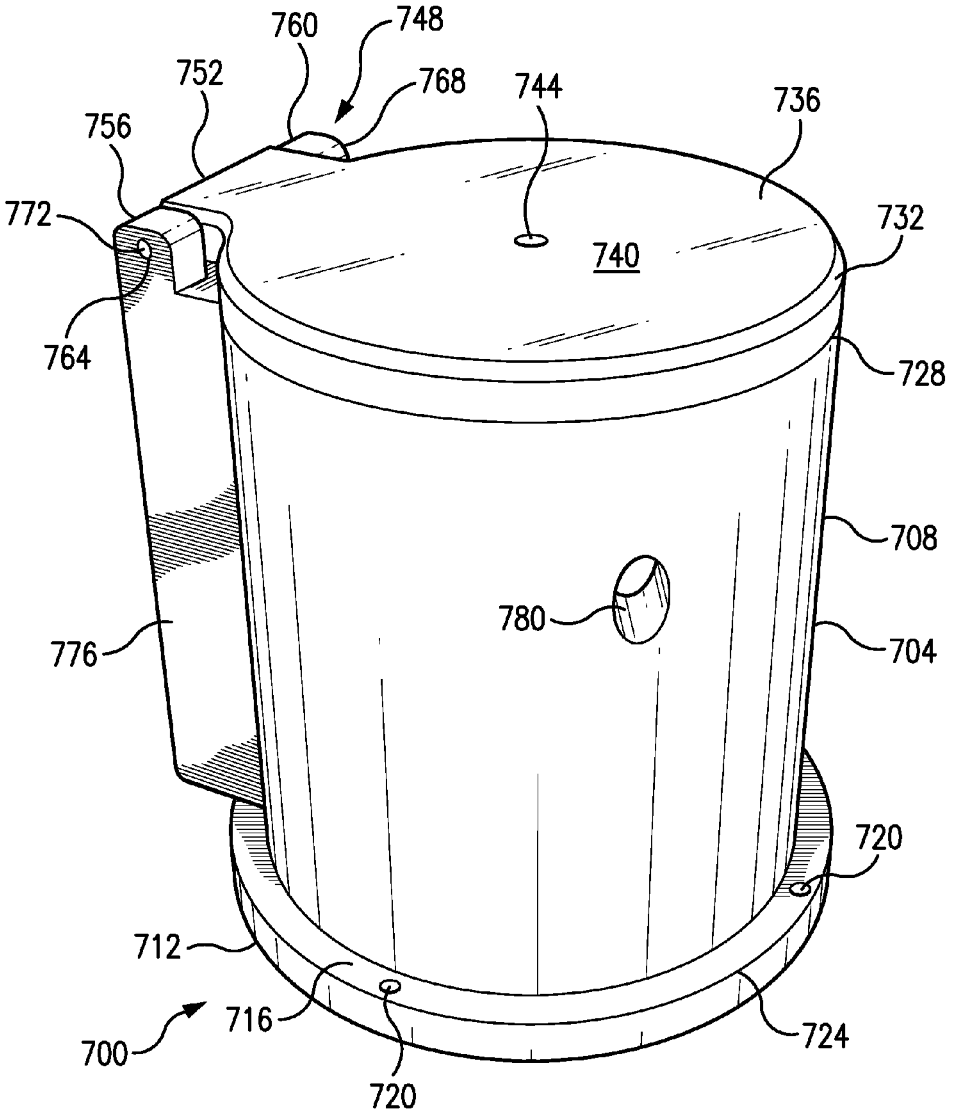
FIG. 12B is a side perspective view of the centrifuge subsystem shown in FIG. 12A.

A side perspective view of centrifuge subsystem of 700 is shown in FIG. 12B. This view of centrifuge subsystem 700 affords a more detailed perspective of hinge 748. Hinge 748 comprises a lid hinge portion 752 that is received by a first hinge receiving arm 756 and second hinge receiving arm 760, which are a part of centrifuge housing 704.

First and second hinge receiving arms 756 and 760 comprise respectively first axle receiving aperture 764 and second receiving aperture 768. A hinge axle 772 can be placed through the first and second receiving apertures to secure lid hinge portion 752. First and second hinge receiving arms 756, 760 are part of a housing hinge assembly 776, which is described in greater detail in respect to FIG. 12C. In FIG. 12B, visible in centrifuge housing sidewall 708 is a housing drain aperture 780. Housing drain aperture 780 allows passage of a tubing for drainage of fluids from within centrifuge subsystem 700.

Figure 12C:
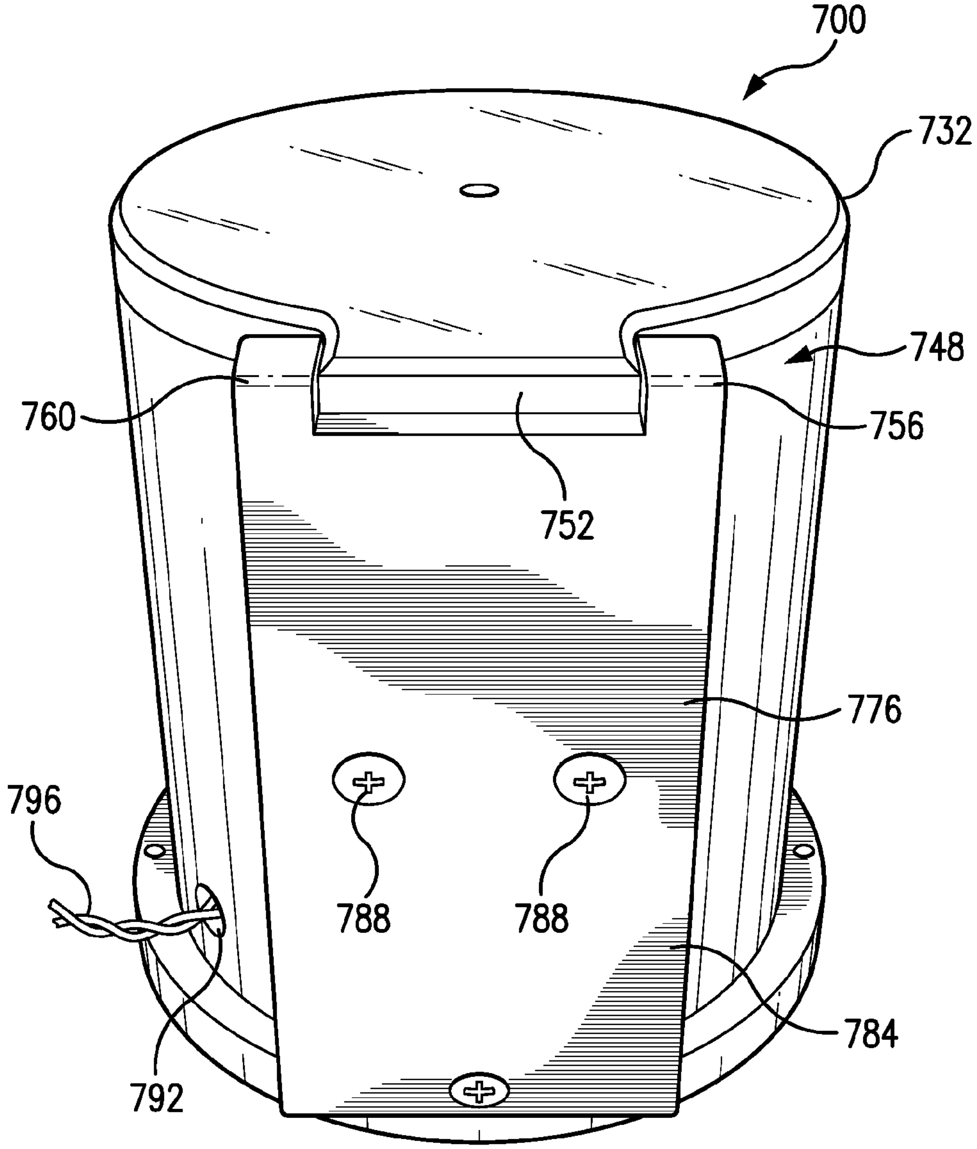
FIG. 12C is a rear perspective view of the centrifuge subsystem shown in FIG. 12A.

FIG. 12C displays a rear perspective view of centrifuge subsystem 700. The rear view of centrifuge subsystem 700 affords visibility of housing hinge assembly 776. Housing hinge assembly 776 comprises a housing hinge plate 784. Housing hinge plate 784 comprises hinge plate mounting apertures 788. Hinge plate mounting apertures 788 allow the housing hinge plate to be connected to the centrifuge housing 704. While FIG. 12C shows the housing hinge plate as discrete element and connected to the centrifuge housing, other embodiments allow the lid to be directly formed with the centrifuge housing 704. A power supply line aperture 792 allows entry of a power supply line 796 through housing sidewall 708 to supply power to a motor configured to drive a rotor of the centrifuge subsystem 700. Use of a power supply line aperture is optional as power can be supplied to the motor by other means. For example power could be supplied from below the motor through a power supply line emanating from an emulsion thermocycling system or apparatus.

Figure 12D:
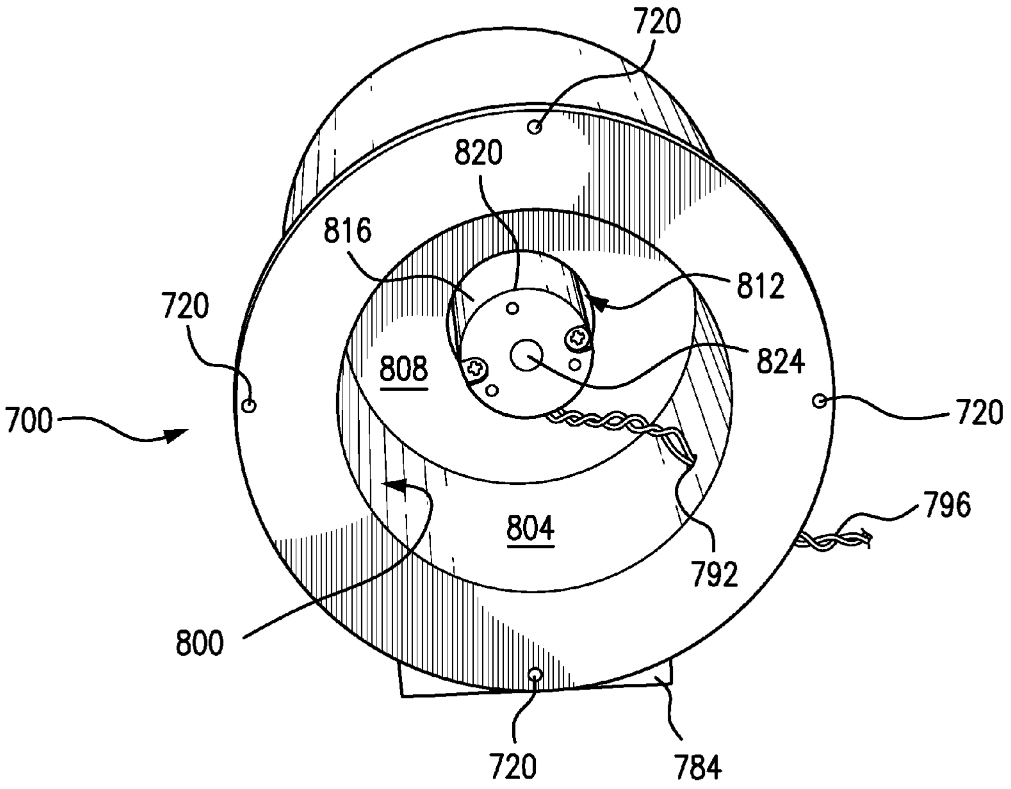
FIG. 12D is a bottom perspective view of the centrifuge subsystem shown in FIG. 12A.

A bottom perspective view of centrifuge subsystem 700 is shown in FIG. 12D. Centrifuge housing 704 is inset to provide a housing bottom recess 800. Housing bottom recess 800 comprises bottom recess sidewalls 804 and a bottom recess ceiling 808. The bottom recess ceiling provides a housing motor aperture 812 through which a motor 816 can be inserted. Motor 816 comprises a motor housing 820 as well a motor rotor axle 824.

Any suitable motor can be utilized as part of the centrifuge such that it can provide the desired angular velocity and acceleration to the centrifuge rotor. Motor control can be one directional or can involve a feedback mechanism. Means and mechanisms can be provided to measure or control at least one of the number of revolutions, velocity, acceleration, and braking. Control can be voltage, current, or resistance based. Any suitable centrifuge construction, power, and control can be employed, for example, as described in U.S. Pat. Nos. 3,990,633, 4,070,290, 4,822,331, 5,342,280, and U.S. Pat. No. 6,879,262 B1, which are incorporated herein in their entireties. A pattern of contrast alternation, for example, black and white, can be provided on the underside of the rotor in operable combination with an optical detector. The motor can be provided with a housing that contains the components of the motor. The motor housing can include any device or mechanism to allow for mounting or other connection to the centrifuge housing. The motor can comprise a rotor axle on which the rotor can be mounted or otherwise connected. Multiple motor can be employed. The motor can be configured for use with direct current (DC), alternating current (AC), or both. The angular direction of the motor can be adjust to move either clockwise or counterclockwise, or both. Any suitable rotor can be employed such as the rotor described herein in accordance with the present teachings.

Figure 13A:
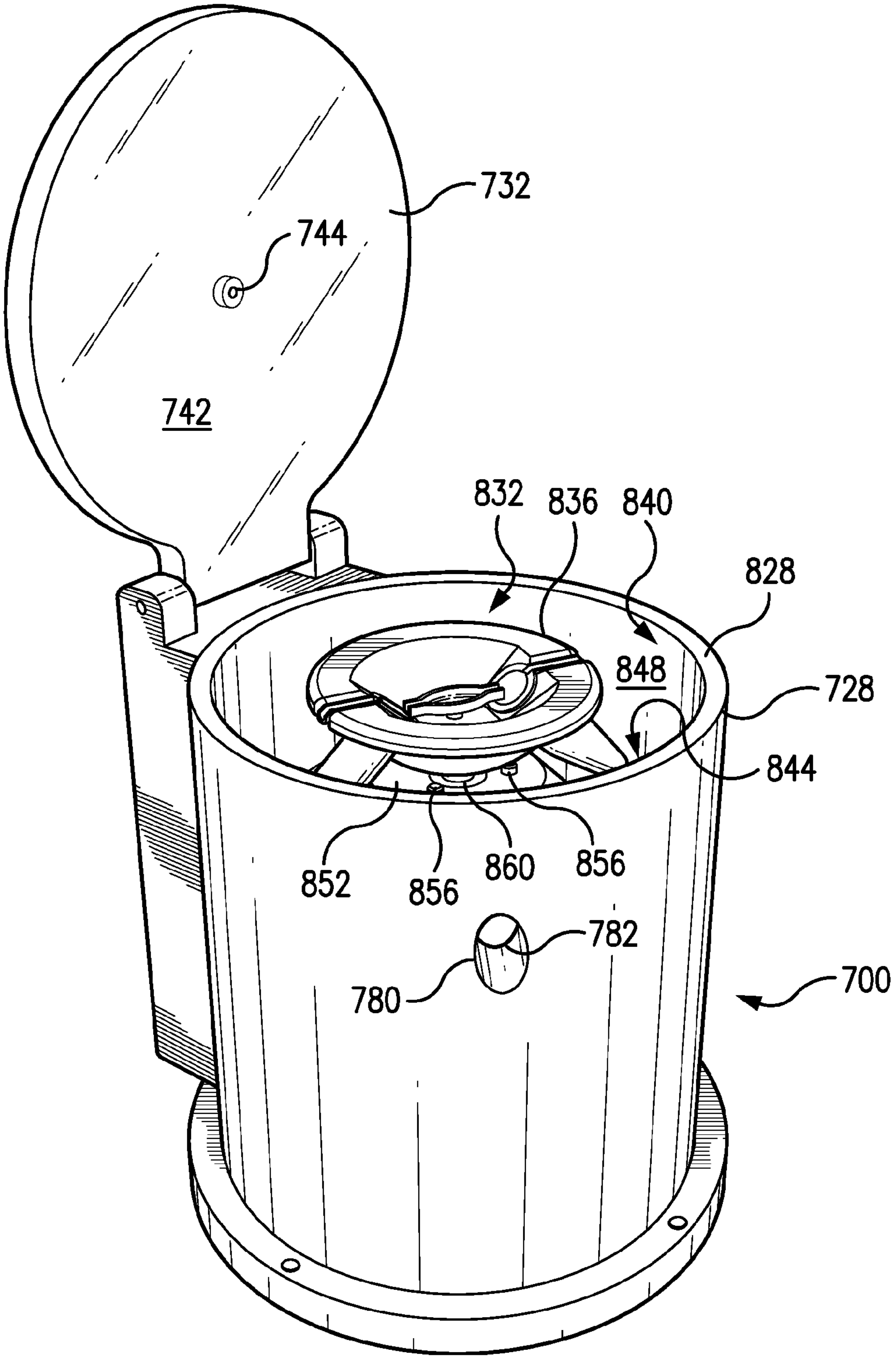
FIG. 13A is a side perspective view of the centrifuge subsystem shown in FIG. 12A, in an open configuration.

FIG. 13A shows a side perspective view of centrifuge subsystem 700 in an open configuration. Lid 732 is in the open configuration such that the interior of the centrifuge 700 can be seen as well as the top housing rim 828 on which lid 732 rests while in a closed configuration. A rotor 832 having a rotor housing 836 is visible through top housing aperture 840 defined by top housing room 828. Centrifuge 700 provides a housing basin 844 as visible and defined by the top housing room 828. Housing basin 844 provides basin sidewalls 848 as well as a receiving platform 852. Receiving platform 852 comprises motor mounting apertures 856 as well as a central rotor axle aperture 860.

Figure 13B:
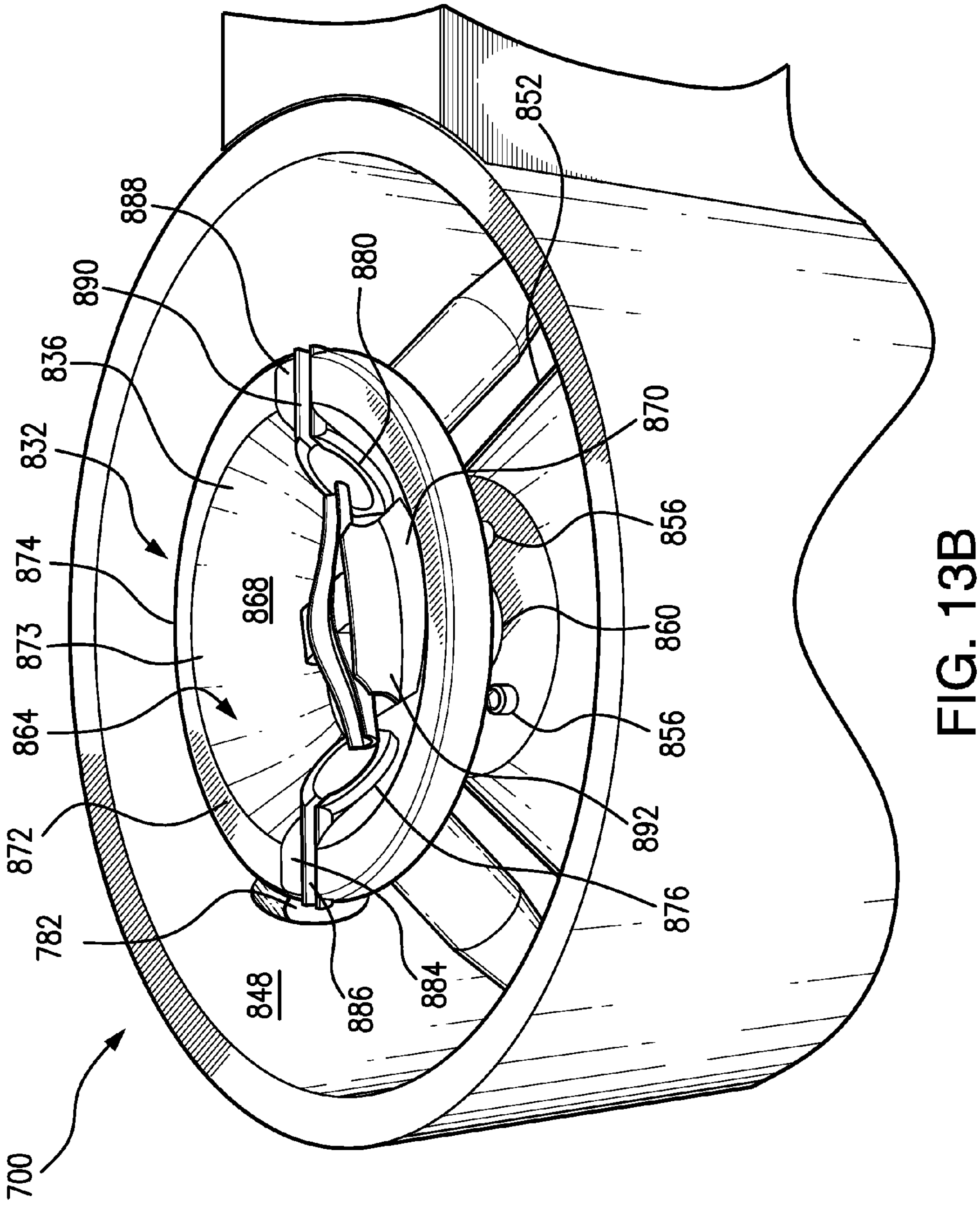
FIG. 13B is another side perspective view of the centrifuge subsystem shown in FIG. 12A, in an open configuration.

FIG. 13B shows the housing basin 844 and rotor 832 in greater detail. Rotor 832 and its rotor basin 864 comprise rotor basin sidewalls 868 and rotor basin floor 870. And a rotor top rim around the periphery and upper end of rotor basin sidewalls 868. Rotor basin sidewalls 866 provide at least one collection tube receptacle. As shown in FIG. 13B, rotor basin sidewalls 868 provide first tube receptacle 876 and second tube receptacle 880. Any number of tube receptacles can be provided in rotor basin sidewall depending in part on the size of the tubes to be inserted and the overall size and surface area of the rotor basin sidewall 868. Rotor top rim 872 has an inner perimeter 873 and outer perimeter 874. Alongside the respective tube receptacles and provided in rotor top rim 872 are collection tube exit channels receptacles. As seen in FIG. 13B, first tube exit channel receptacle 884 and second tube exit channel receptacle 888 are provided respectively with first and second receptacle grooves 886, 890. At the center of the rotor basin 864 is a fluid distribution device or slinger receptacle 892 comprising slinger receptacle sidewalls 894.

A fluid collection tube is provided comprising a main tube body and a tube extension. The main tube body can comprise a main body sidewall surrounding a tube interior comprising a tube opening at a first end, and a second end distal to the first end providing a sealed base. The tube extension can comprise a tube extension sidewall defining a fluid exit channel in fluid communication with the tube interior through a tube channel inlet proximal to the tube opening and extending to a tube channel outlet distal to the tube opening. The fluid collection tube can further comprise a tube lip disposed about the perimeter of the tube opening and allowing fluid communication of the tube exit channel with the tube interior. An optional tube buttress disposed between the tube extension sidewall and the main tube sidewall provides further support and rigidity. The tube extension sidewall and the main tube sidewall can be positioned at any angle relative to one another, from about 15° to about 90°, from about 1.0° to about 80°, from about 5.0° to about 75°, from about 10° to about 65°, from about 20° to about 60°, from about 25° to about 50°, from about 30° to about 45°, from about 30° to about 60°, from about 40° to about 50°, or greater than about 90° relative to each other.

The fluid collection tube can be provided in any suitable shape including the main tube body and the tube extension. For example, the main tube body can comprise a generally cylindrical portion proximal the first end, a conically tapered portion proximal the second end, and a rounded second end. For example, the tube exit channel and tube extension sidewall can have a U-shaped cross-section along a longitudinal axis. The average cross-sectional area of the exit tube channel can be less than, equal to, or greater than the average cross-sectional area of the tube interior. The average cross-sectional area of the exit tube channel can be less than about 95%, less than about 90%, less than about 75%, less than about 60%, less than about 50%, less than about 40%, less than about 25%, less than about 20%, less than about 15%, less than about 10%, less than about 5%, or less than about 1% of the average cross-sectional area of the tube interior.

The fluid collection tube of the present teachings can optionally comprise a cap or lid. The lid can be completely separable from the tube housing or can be permanently joined to the housing, for example, through a flexible hinge. The cap can be configured to close off the main tube interior, the fluid exit channel, or both.

The fluid collection tube can be constructed from any suitable material. Suitable materials include metals, plastics, glass, ceramics, or any combination thereof. Examples of suitable plastics include polypropylene, polycarbonate, and polyvinyl chloride. The fluid collection tube can be constructed to contain any desired volume. The fluid collection tube can have a volume of less than about 1 μL, from about 1 μL to about 1 L, from about 10 μL to about 1 dL, from about 100 μL to about 1 cL, from about 500 μL to about 50 mL, from about 1 mL to about 25 mL, from about 2.5 mL to about 15 mL, from about 5 mL to about 10 mL, or greater than about 1 L.

Figure 14A:
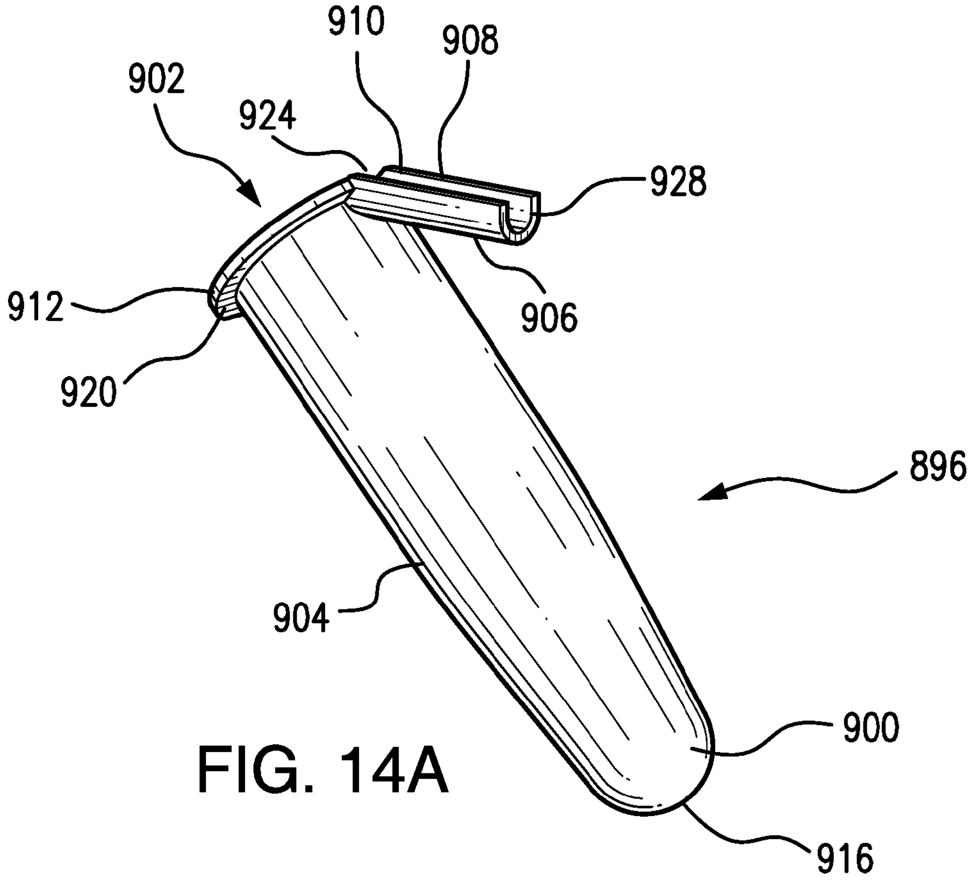
FIG. 14A is a side perspective view of a collection tube in accordance with various embodiments of the present teachings.

FIG. 14A shows a side perspective view of a collection tube 896 in accordance with the present teachings. Collection tube 896 comprises a tube housing 900 including a main tube body 904, comprising a tube interior 902, and a tube extension 906 comprising a fluid exit channel 908. The length of the collection tube is defined by a first tube end 912 and a second tube end 916. At first tube end 912, is a tube lip 920 that can be engaged by rotor sidewall apertures tube receptacles 876, 880. Fluid exit channel 908 has a length defined by a tube channel inlet 924 and a tube channel outlet 928.

Figure 14B:
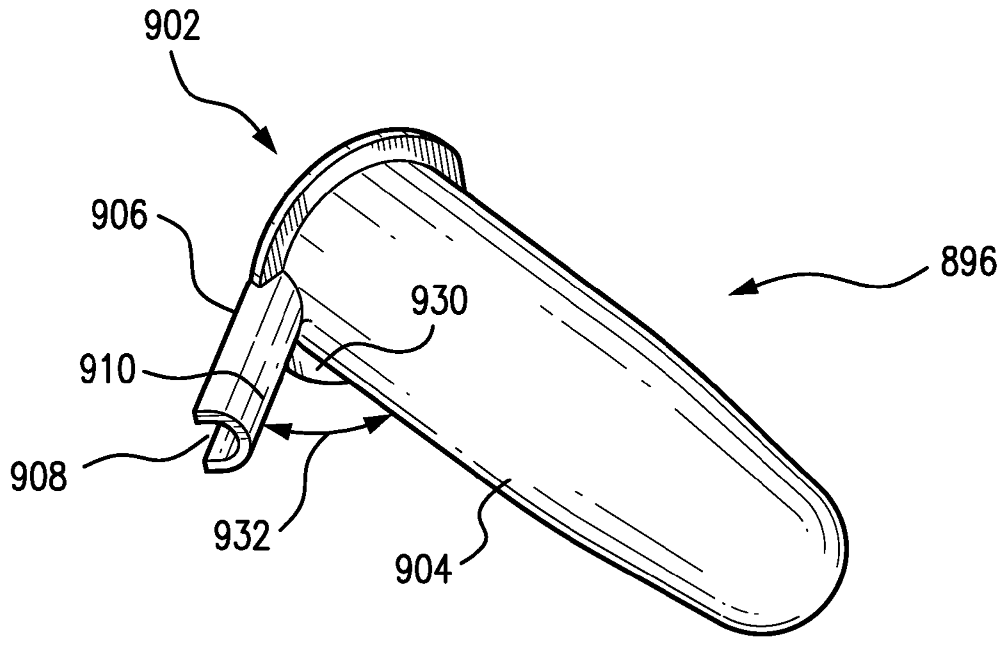
FIG. 14B is another side perspective view of the collection tube shown in FIG. 14A.
Figure 14C:
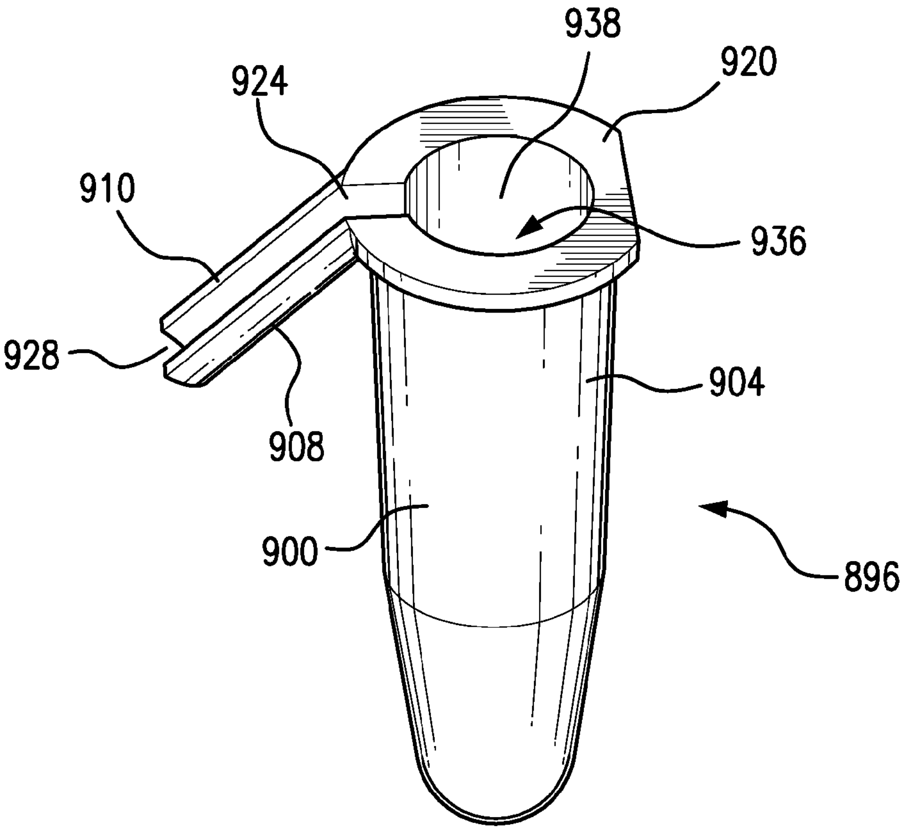
FIG. 14C is a top perspective of the collection tube shown in FIG. 14A.

A top perspective view of collection tube 896 is shown in FIG. 14B. In particular an angle 932 is shown defined by the spacing of the side walls 910 of tube extension 906 from main tube body 904. An optional tube buttress 930 is also shown between the main tube body and the tube extension. Collection tube 896 is again visible in FIG. 14C. Tube inlet 920 defines and surrounds a tube opening (aperture) 936 having a tube opening center 938. At the middle of tube opening 936 is tube opening center 938.

A fluid distribution device, also referred to herein as a "slinger," is provided by the present teachings. The slinger can comprise sidewalls defining a central channel comprising a first end, a central zone, and a second end along a longitudinal axis. Sidewall lateral extensions, also referred to as "wings" herein, can be provided, extending away from the sidewalls on either side of the central channel. The wings are useful in mating with and ensuring a secure connection with a fluid distribution device receptacle of a centrifuge rotor. The slinger can have any number of spouts that can be correlated with the number of fluid collection tubes to be used in conjunction with the slinger. For example, when two fluid collection tubes are employed, the slinger can include a first spout extending from the central zone to the first end and terminating at a first spout outlet, the sidewalls tapering along the central zone toward the first spout; and a second spout extending from the central zone to the second end and terminating at a second spout outlet, the sidewalls tapering along the central zone toward the second spout.

The slinger can be configured to mate with a fluid distribution device receptacle of a centrifuge rotor using any suitable configuration. For example, wings, as described herein, can be employed. Rather than use an insertable/detachable slinger, a slinger can be employed that is permanently or integrally associated with the rotor housing.

The slinger can be fabricated from any suitable material or materials such as those described herein for the collection tube. The slinger can comprise one or more of the materials described herein for the fluid collection tubes. The slinger can have any desired volume. The slinger can have a volume or less than about 1 μL, from about 1 μL to about 1 L, from about 10 μL to about 1 dL, from about 100 μL to about 1 cL, from about 500 μL to about 50 mL, from about 1 mL to about 25 mL, from about 2.5 mL to about 15 mL, from about 5 mL to about 10 mL, or greater than about 1 L.

Figure 15:
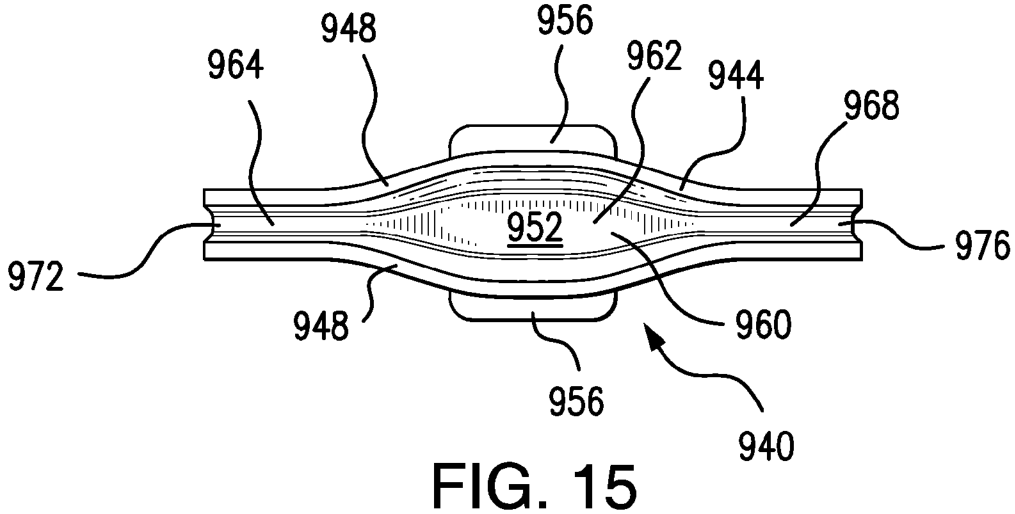
FIG. 15 is a plan view of a fluid distribution device (slinger) in accordance with various embodiments of the present teachings.

FIG. 15 is a plan view of a liquid distribution device or slinger 940. Slinger 940 comprises a slinger housing 944, which is shaped to provide slinger sidewalls 948, a slinger base 952, and slinger wings 956. A slinger central channel 960 is defined by the slinger base 952 and slinger sidewalls 948 running the length of the slinger. At the center of the slinger is a central zone 962. Well slinger 940 is shown having a single central channel 960 additional central channels can be provided in other embodiments. First slinger spout 964 and second slinger spout 968 comprise opposite sides and ends of the slinger central channel. At either end of slinger central channel 960 as well as the ends of respective first slinger spouts 964, 968 are first slinger spout outlet 972 and second slinger spout outlet 976.

A centrifuge rotor is provided by the present teachings, which is particularly suitable for separating water-in-oil emulsions and removing the oil phase of such an emulsion. The centrifuge rotor can comprise a rotor housing having a bisecting rotor axis perpendicular to a central rotor axis, a rotor basin formed by the rotor housing, a rotor basin floor, and a rotor basin sidewall lining the rotor housing basin and extending up toward a rotor top rim having an inner perimeter and an outer perimeter. The rotor can further comprise at least one collection tube receptacle comprising an opening formed in the basin sidewall, and at least one tube extension receptacle having a grove formed in the rotor top rim and extending from the inner perimeter to the outer perimeter. The sidewalls can comprise a substantially flat inset region about the collection tube receptacle and adjacent the tube receptacle opening.

The centrifuge rotor can be provided with any number of collection tube receptacles and corresponding tube extension. Generally, an even number of receptacles are provided on opposite sides of the rotor basin. For example, first and second tube receptacles positioned opposite each other along the bisecting rotor axis; and first and second tube extension grooves opposite each other along the bisecting rotor axis. An odd number of receptacles can be utilized, and in such embodiments the rotor can be balanced to account for the weight of any unpaired receptacles. Balancing can also be provided for embodiments where an even number of receptacles are provided but when not all receptacles are fitted with collection tubes or collection tubes of unequal volume or weight. The rotor can also comprise at least one liquid distribution device (slinger) receptacle extending from the rotor basin floor and having a distribution device receptacle longitudinal axis.

The collection tube receptacle opening and the tube extension groove are generally positioned at an angle relative to each other corresponding to the angle of the tube extension sidewall relative to the main tube body. For example, the collect tube receptacle and the tube extension groove can be from about 15° to about 90°, from about 1.0° to about 80°, from about 5.0° to about 75°, from about 10° to about 65°, from about 20° to about 60°, from about 25° to about 50°, from about 30° to about 45°, from about 30° to about 60°, from about 40° to about 50°, or greater than about 90° relative to each other. The shape of the rotor sidewall can be configured to accommodate a collection tube buttress. The fluid distribution device receptacle can include a means for receiving or reversibly locking in place the slinger. For example, the slinger receptacle can contain opposing sidewalls on either side of the distribution device receptacle longitudinal axis that can cooperate with wings on the slinger.

The slinger receptacle can be provided in any suitable configuration within the centrifuge rotor. The bisecting rotor axis can be parallel or non-parallel to the distribution device receptacle longitudinal axis. The axes can be positioned from about 0.01° to about 25°, from about 0.05° to about 20°, from about 0.15° to about 15.0°, from about 0.25° to about 10.0°, from about 0.5° to about 5.0°, from about 1.0° to about 2.5°, less than about 0.01°, or greater than about 25° relative to each other.

Figure 16:
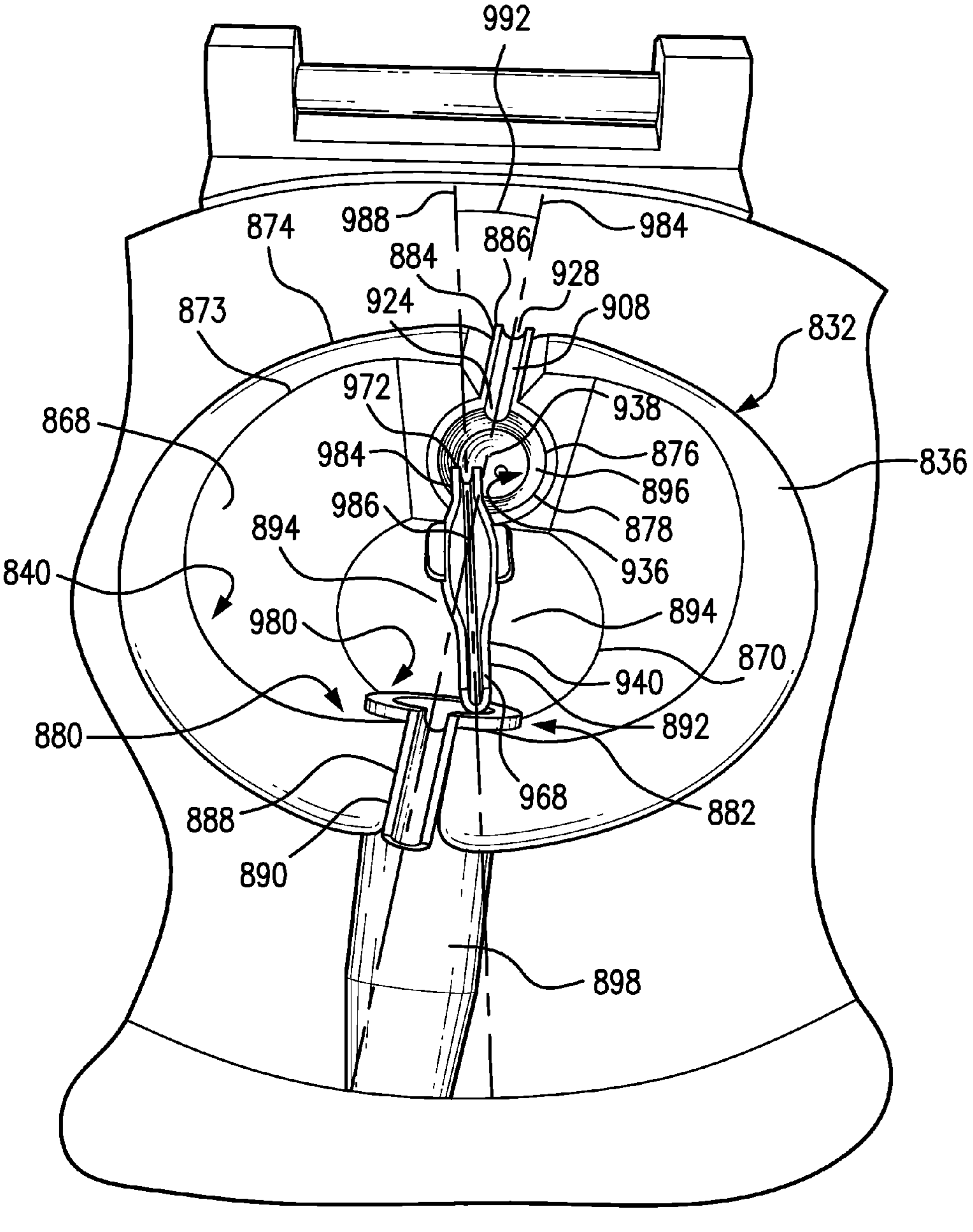
FIG. 16 is a top perspective view of the centrifuge subsystem in an open configuration of the centrifuge subsystem shown in FIG. 12A.

FIG. 16 is a top perspective view of rotor 832 as positioned in housing basin 844. First collection tube 896 and second collection tube 898 are disposed in respective first and second tube receptacles 876 and 880. Slinger 940 is positioned in slinger receptacle 892. Collection tubes 896 and 898 each have respective tube openings 936 and 980, which in turn have respective tube opening centers 938 and 982. Cutting the rotor approximately in half is a bisecting rotor axis 984, which can be perpendicular to central rotor axis 986, extending into and out of the page. Along the slinger central channel 960, along the length of slinger 940 and extending out either end is a slinger longitudinal axis 988. Slinger 940 is mounted in slinger receptacle 892 so that slinger 940 is offset from the centers of the respective collection tubes 896, 898. Rather than the slinger spout outlet 972 being directly in line with the first tube opening center 938, there is an offset of and by an angle 992 defined by the spacing of bisecting rotor axis 984 from slinger longitudinal axis 988. Angle 992 can be varied as appropriate. The offset of slinger 940 from the respective tube opening centers accounts for angular movement of the rotor such that when in motion any fluid exiting respective first slinger spout outlets 972, 976 will land at or near respective tube opening centers 938, 932. The offset angle 992 can be varied to account for changes in the angular speed of or acceleration for the rotor 832.

When the centrifuge is run in accordance with the present teachings, fluid from the fluid collection tubes is expelled from the rotor through the tube exit channels. The expelled fluid can be accumulated, processed, or discarded using any suitable means or mechanism. For example a peripheral gutter can be employed. The peripheral gutter can include a gutter housing providing a top gutter surface, a bottom gutter surface, and gutter sidewalls extending between the top and bottom gutter surfaces along an outer gutter perimeter of the gutter housing. A gutter inlet can be located along an inner perimeter of the gutter housing. The gutter can be connected to the centrifuge housing using any means or mechanism. For example, a gutter flange extending around the gutter outer perimeter and adapted for placement on the top housing rim can be employed. The fluid collected in the peripheral gutter can be discarded using any means or mechanism. For example, a gutter outlet can be provided in the gutter housing along with a housing drainage aperture in the housing sidewall and a basin drainage aperture in the housing basin sidewall. In such a configuration, a drainage tubing can be operatively associated with the gutter outlet and pass through the drainage apertures.

Figure 17:
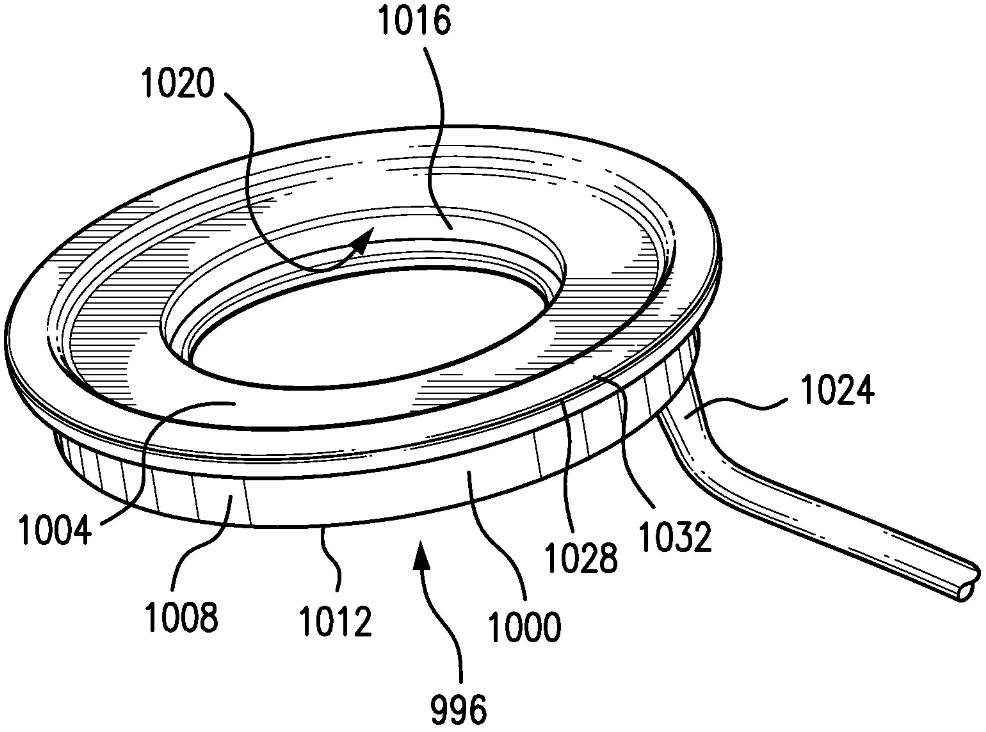
FIG. 17 is a perspective view of a peripheral gutter for use in a centrifuge subsystem as shown in FIG. 12 A.

A peripheral gutter 996 is shown in perspective view in FIG. 17 in accordance with various embodiments of the present teachings. Peripheral gutter 996 serves the function of collecting waste fluid from the centrifuge when the rotor is in operation. Peripheral gutter 996 comprises a gutter housing 1000 providing a top surface 1004, gutter sidewalls 1008, and gutter base 1012. Gutter housing 1000 defines a gutter interior 1016. Providing access to gutter interior 1016 is a gutter inlet 1020. A gutter outlet 1024, in turn, is provided at one or more points along the gutter sidewalls 1008 or gutter base 1012. Along a top outer gutter perimeter 1028 is provided a gutter flange 1032. Gutter flange 1032 is configured to allow placement and engagement on top housing rim 828 of centrifuge housing 704.

Figure 18A:
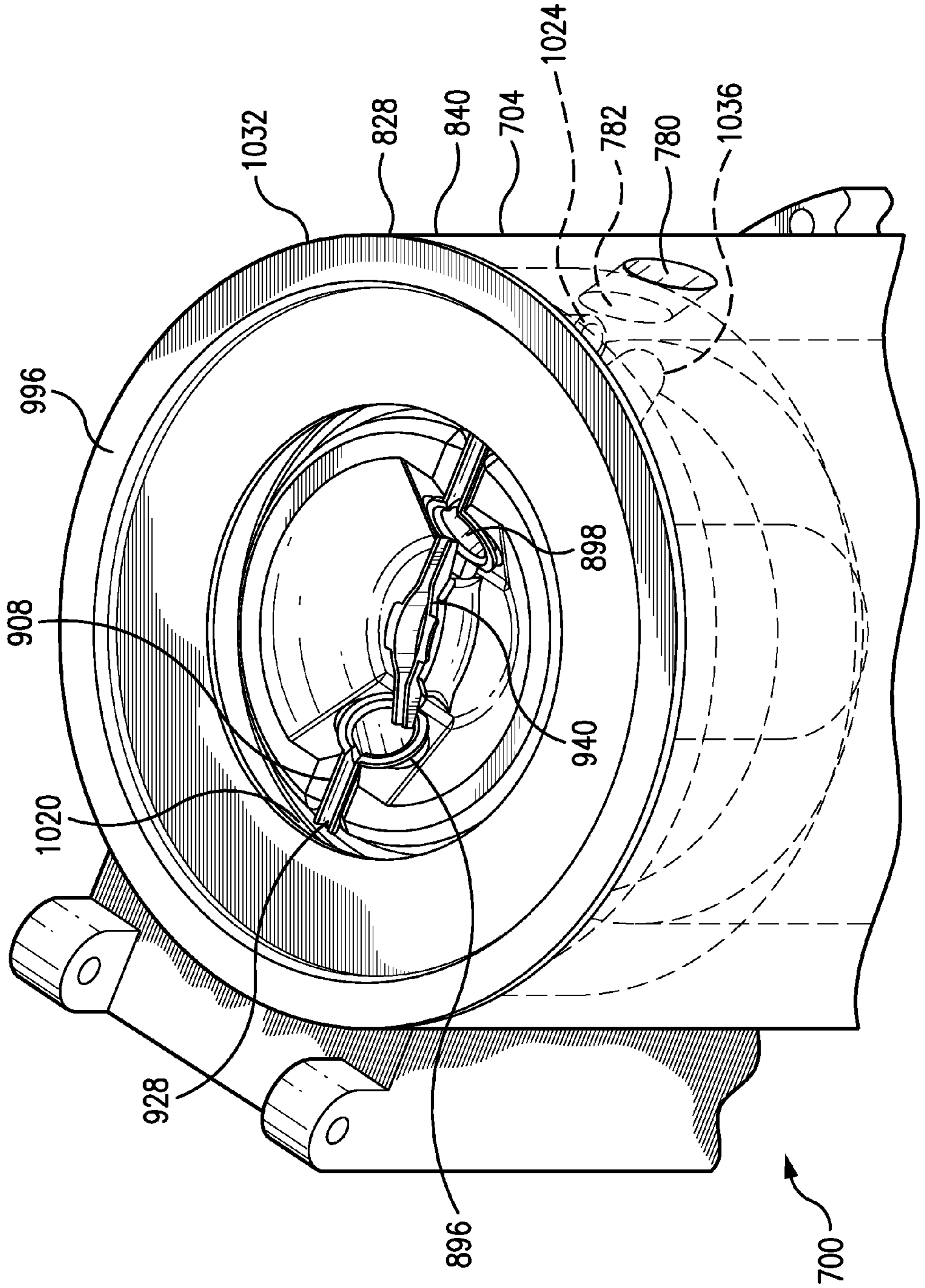
FIG. 18A is a top perspective of the centrifuge subsystem as shown in FIG. 12A with showing the collection tube, slinger, and peripheral gutter components.
Figure 18B:
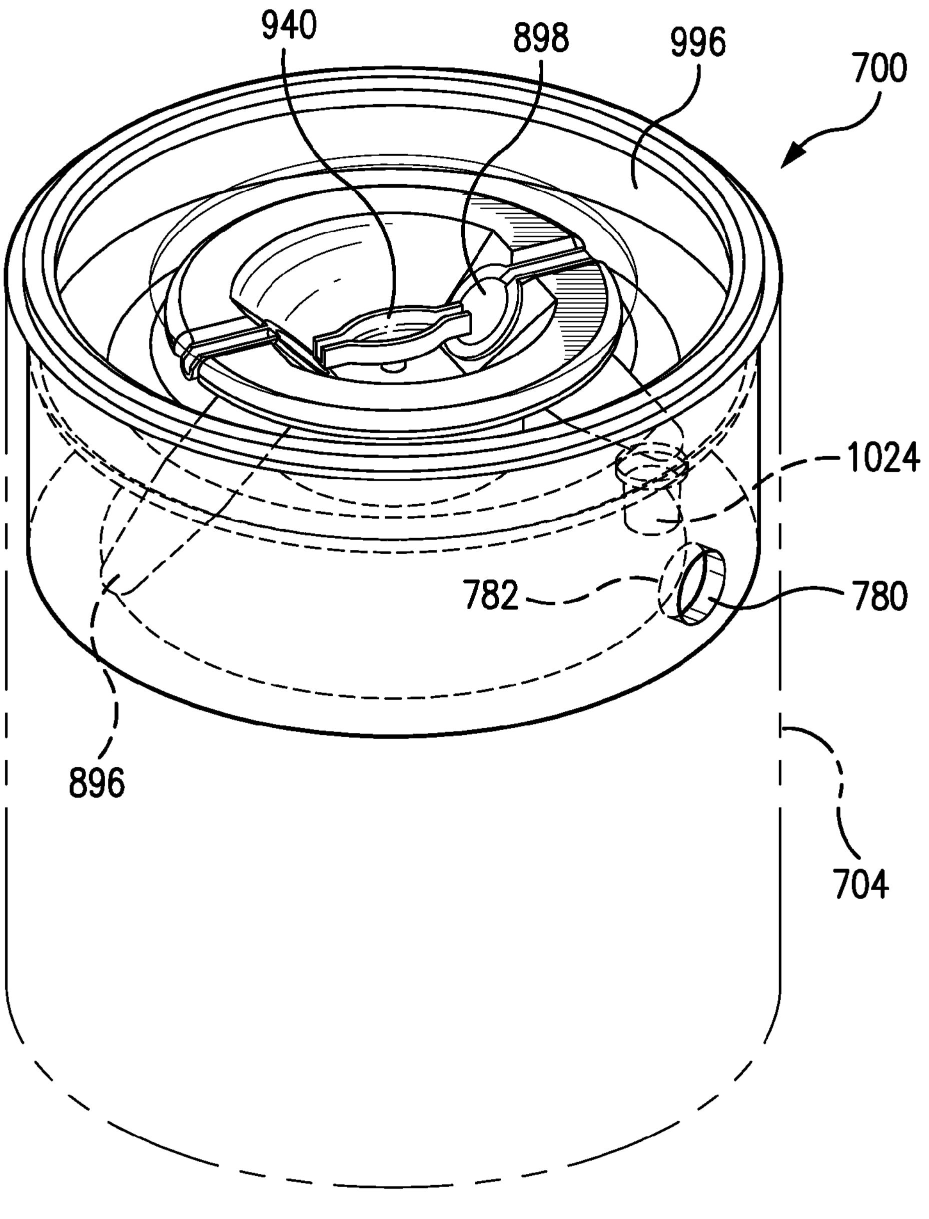
FIG. 18B is a side perspective view of the centrifuge subsystem assembly shown in FIG. 18A.

FIG. 18A shows a top perspective view of centrifuge subsystem 700 as assembled with various components including peripheral gutter 996, first and second collection tubes 896, 898, and slinger 940. A drainage tubing 1036 is shown engaged with gutter outlet 1024 and can be passed through basin drainage aperture 782 and housing drain aperture 780. A side perspective view of centrifuge subsystem 700 as assembled is also shown in FIG. 18B.

Figure 18C:
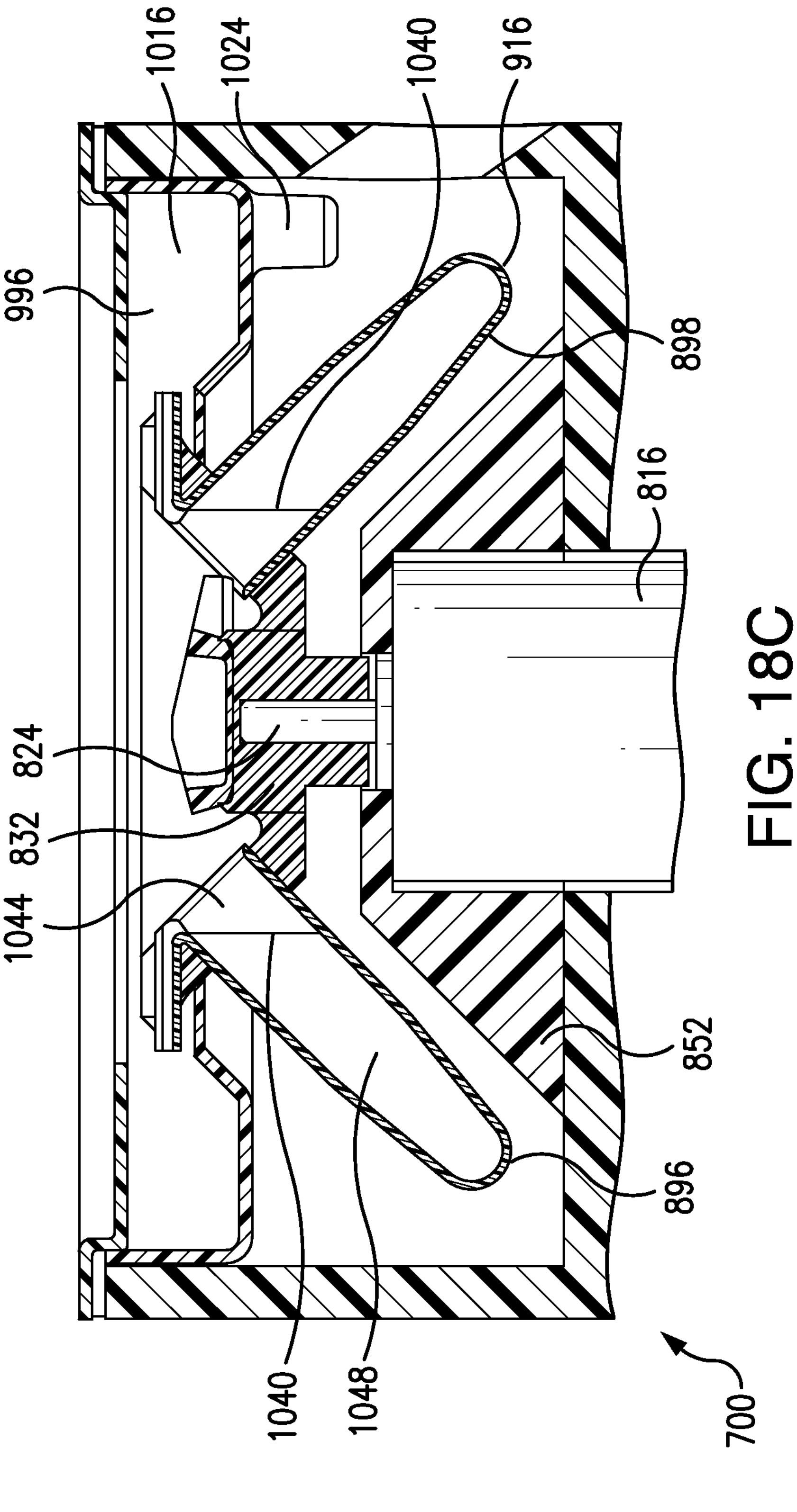
FIG. 18C is a cross sectional view of the centrifuge subsystem assembly as shown in FIG. 18A.

A cross-sectional view of the assembled centrifuge subsystem 700 is shown in FIG. 18C. Rotor 832 rests on and is connected to rotor axle 824 of motor 816. First and second collection tubes 896, 898 are shown filled with fluid comprising an oil/water interface 1040 separating an oil phase 1044 from an aqueous phase 1048. Collection tubes 896,898 can comprise at least one mixing ball each in addition aqueous solution. Such bead or beads are located at the base or second tube end 916. When the rotor is in angular momentum the oil phase can exit the collection tubes through the respective exit tube channels and land in peripheral gutter 996.

The centrifuge of the present teachings is particular suitable for the breaking of emulsions. The emulsion can be in form a sample, i.e., source fluid. Any means or mechanism can be employed to deliver source fluid to the centrifuge. The sample fluid can be delivered through an inlet supply line (fluid supply line). When a lid is not employed, or is not in a closed configuration, the fluid line can be delivered directly into the centrifuge through the top centrifuge opening afforded by the centrifuge housing sidewalls. When a lid is employed and is in a closed configuration, the fluid supply line can pass through at least one of a lid aperture and a housing aperture to gain access to the interior of the centrifuge. For example, the lid can comprise a housing with a top lid surface and a bottom lid surface, a lid aperture extending from the top lid surface to the bottom lid surface. The lid aperture can be located anywhere on the lid, for example, it can be centrally located. More than one lid aperture can be provided. The lid aperture can be configured to accept a fluid supply line and positioned above the fluid distribution device when the lid is in a closed configuration. A fluid supply source can be in fluid communication with the fluid supply line. A fluid supply pump can be configured to pump fluid from the fluid supply source, through the fluid supply line and into the centrifuge.

Figure 19:
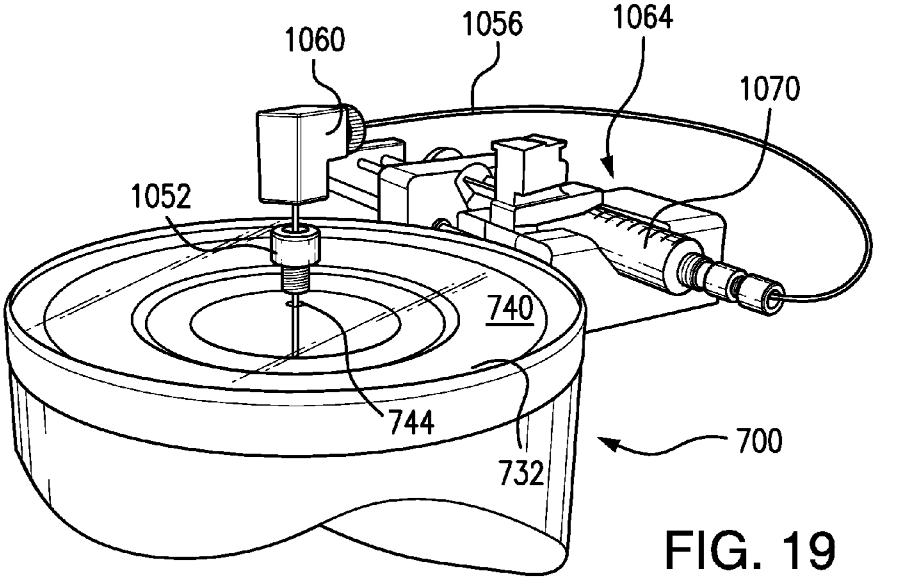
FIG. 19 is a perspective view of a centrifuge subsystem operably connected with a source fluid and source fluid pump in accordance with various embodiments of the present teachings.

Centrifuge subsystem 700 is shown in FIG. 19 in a closed configuration and operably connected to a fluid source. A lid aperture adapter 1052 is connected to centrifuge subsystem 700 through central lid aperture 744. Inlet fluid line 1056 can pass either directly into centrifuge subsystem 700 or through one or more of a lid aperture adapter and a fluid line connector 1060. Fluid line 1056 can originate from a fluid sample source 1070. Fluid sample source 1070 can be supplied to centrifuge subsystem 700 by means of a fluid sample source pump 1064. As shown in FIG. 19, pump 1064 is a syringe style pump. The present teachings allow for use of other types of pumps as well or in addition to a syringe style pump. For example, a peristaltic pump or diaphragm pump could be employed as pump 1064. Fluid line 1056 can originate from an emulsion subsystem 300. The sample fluid supplied by inlet fluid 1056 can comprise a water-in-oil emulsion. The water phase of the water and oil emulsion can comprise microreactors that in turn can contain PCR product or products.

Figure 20:
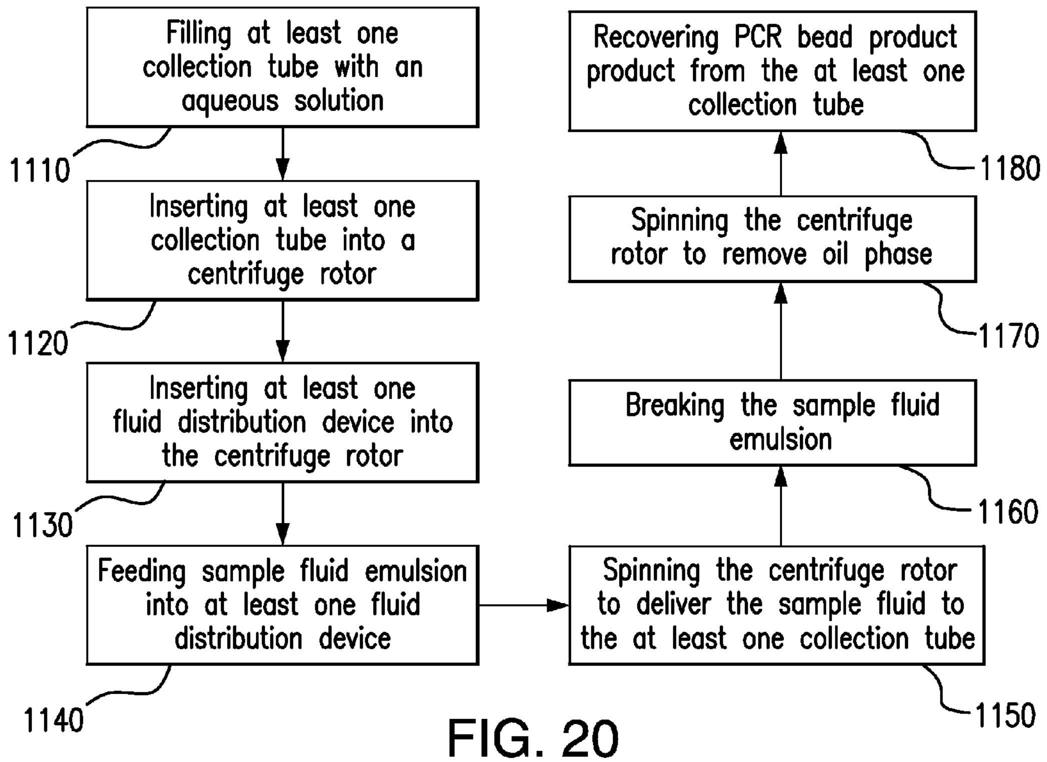
FIG. 20 is a flow chart depicting a method of centrifugation and collection of a sample in accordance with various embodiments of the present teachings.

A method of recovering a polymerase chain reaction (PCR) product from a water-in-oil emulsion is provided in accordance with the present teachings. The method can be performed using the centrifuge or centrifuge components of the present teachings. The method can comprise one or more of the following steps. One or more step can be repeated or omitted. The order of the method steps can be varied. An example of such a method is shown in FIG. 20 (1100). At least one collection tube is filled with an aqueous solution (1110). At least one collection tube is inserted into a tube receptacle of a centrifuge rotor (1120). At least one fluid distribution device (slinger) is inserted into a fluid distribution device receptacle of the centrifuge rotor (1130). Sample fluid, which can comprise a PCR product in a water-in-oil emulsion, is fed into the fluid distribution device (1140). The centrifuge rotor is spun to deliver the sample fluid to the at least one collection tube (1150). The emulsion is partly or completely broken in the at least one collection tube (1160). The centrifuge rotor motor can also be spun to remove an oil phase from the collection tube (1170). The method can further comprise collecting the oil phase in a peripheral gutter, that is, the oil phase removed from the collection tube. The method can further comprise recovering PCR product from the at least one collection tube (1180).

Any suitable aqueous solution can be employed in the collection tubes and generally comprises at least water. The aqueous solution can contain a surfactant, a detergent, or both. A component that is both a surfactant and a detergent can be employed. Multiple surfactants or detergents can be used. Any surfactant or detergent can be used, for example, those described in U.S. Pat. No. 4,938,876, which is herein incorporated in its entirety. For example, the aqueous solution can comprise sodium dodecyl sulfate (SDS). The aqueous solution can comprise an alcohol, for example, ethanol. The surfactant, detergent, SDS, alcohol, or ethanol, alone, or in any combination can be present in the aqueous solution in an amount less than about 0.001 vol. %, from about 0.001 vol. % to about 100 vol. %, from about 0.01 vol. % to about 95 vol. %, from about 0.1 vol. % to about 90 vol. %, from about 0.5 vol. % to about 85 vol. %, from about 1.0 vol. % to about 80 vol. %, from about 5.0 vol. % to about 75 vol. %, from about 10 vol. % to about 60 vol. %, from about 15 vol. % to about 50 vol. %, from about 20 vol. % to about 40 vol. %, or from about 25 vol. % to about 35 vol. % of the total volume of the aqueous solution. An SDS solution can also be used as a wash solution. The aqueous solution can comprise one or more salts to aid in the breaking of the emulsion. One or more acid or base can be added to the aqueous solution to adjust pH to assist in breaking the emulsion.

Use of a mixing ball can aid in the recovery of PCR product laden beads. The at least one collection tube can contain at least one mixing ball capable of capturing PCR product associated beads. The mixing ball can be constructed from any suitable material, for example, one or more material described herein for constructing fluid collection tubes, slingers, and housings. Any number of beads can be recovered. For example, from about 1 bead to about 1 trillion beads can be recovered, from about 100 beads to about 100 million beads can be recovered, from about 1,000 beads to about 10 million beads, from about 10,000 beads to about a million beads, from about 100,000 beads to about 500,000 beads, or more than 1 trillion beads can be recovered. Percent recovery of beads can be any desired percentage based on the number of beads supplied to the centrifuge tube. Bead recovery can be quite high such as 120 million beads recovered out of 140 million input. For example, bead recovery can be less than 1.0%, from about 1.0% to about 100%, from about 5.0% to about 95%, from about 10% to about 90%, from about 15% to about 85%, from about 20% to about 80%, from about 25% to about 75%, from about 30% to about 60%, or from about 40% to about 50% of input beads.

The fluid distribution device (slinger) can be inserted into a corresponding receptacle of the rotor so that at least one fluid distribution outlet is displaced off center from a center of the at least one collection tube, and the spinning occurs in the direction of the displacement. The degree of slinger displacement can be relative to at least one of an angular velocity and an angular acceleration of the spinning rotor. The degree of the displacement can result in the sample fluid entering the at least one collection tube at a center of the tube. The rotor can be spun at any desired speed. For example, the rotor can be spun less than 1 rpm, from about 1 rpm to about 100,000 rpm, from about 10 rpm to about 60,000 rpm, from about 50 rpm to about 30,000 rpm, from about 100 rpm to about 10,000 rpm, from about 500 rpm to about 5,000 rpm, or from about 1,000 rpm to about 2,500 rpm or more. The acceleration of the rotor can be held constant, varied, or both. For example, the acceleration can be less than about 1 G, from about 1 G to about 1,000 G, from about 3 G to about 300 G, from about 5 G to about 100 G, from about 10 G to about 50 G, from about 15 G to about 30 G, or greater than 1,000 G.

The contents of the at least one collection tube can be mixed or oscillated by alternating the direction of the spinning rotor. Oscillation can be employed to resuspend beads or particles. The direction of the rotor can be changed at any desired frequency. The rate of frequency can also be varied over time. For example, the direction of the rotor can be changed about every 1 millisecond, about every 10 milliseconds, about every 100 milliseconds, about every 1 second, about every 10 seconds, about every 30 seconds, about every minute, about every 5 minutes, about 10 minutes, about every 15 minutes, about every 20 minutes, about every 30 minutes, or about every hour.

According to various embodiments of the present teachings, amplified DNA fragments tethered to a particle or bead can be prepared. Device, systems, apparatuses, and methods are described herein relating to the amplified polynucleic acid tethered particles or beads. The method can begin by forming an inverse emulsion comprising a plurality of aqueous droplet microreactors encapsulated and separated from one another by a carrier fluid, for example, an immiscible oil or a fluorinated liquid. Each microreactor, or at least one of them, can contain a template bead, also referred to as a P1 bead or a primer 1 bead, and PCR ingredients. The amplification process may be referred to as a bead-based emulsion amplification. Beads along with DNA templates can be suspended in an aqueous reaction mixture (a microreactor mixture) and then droplets of the mixture can be encapsulated by the immiscible liquid in an inverse (water-in-oil) emulsion. The template DNA may be either bound to the bead prior to emulsification or may be included in solution in the amplification reaction mixture.

According to various embodiments, a method and system are provided for automated sample preparation for sequencing applications. In some embodiments, bead-based emulsion amplification is performed upon formation of an emulsion which encapsulates aqueous droplets. Each droplet can contain a template DNA strand and a bead upon which amplicons to be formed from the template DNA. The droplet can also contain a reagent mixture for enabling the amplification reaction. The emulsion can comprise an inverse (water-in-oil) emulsion with the aqueous phase (e.g., the microreactor mixture) including the reagent mixture and the bead, and the carrier fluid including oil or other non-aqueous liquid that is partially or completely immiscible with the aqueous phase.

According to various embodiments, an emulsion thermocycling subsystem is provided. The thermocycling subsystem can comprise a first thermocycling plate, as described herein, and a heating subassembly, as described herein. The heating subassembly of the thermocycling system can also comprise a complementary heating block as described herein. The heating subassembly of the thermocycling system can also comprise a second thermocycling plate. The thermocycling subsystem can be insulated using any means or mechanism. For example, a gasket can be used for insulating purposes.

In some embodiments, a thermocycling plate is provided in accordance with the present teachings. The thermocycling plate generally comprises a slab housing and a main fluid passage passageway that passes through the slab housing. The main fluid passageway is disposed in the slab housing and can include an inlet, an outlet, and various fluid passage segments in fluid communication with adjoining fluid passages. The main fluid passageway can comprise a number of fluid passages collectively in fluid communication. Such fluid passages can include an initial fluid passage in fluid communication with the inlet, a transition fluid passage in fluid communication with the initial fluid passage, main fluid passage in fluid communication with the transition fluid passage. The main fluid passage can be in direct fluid communication with the outlet or via an exit fluid passage. The main fluid passage, the initial fluid passage, or both can have a tortuous shape. The main fluid passage, the initial fluid passage, or both can have a plurality of cycles (paths) between their respective partitions.

A heating subassembly is also provided by the present teachings and can be used in combination with one or more thermocycling plates described herein. The heating subassembly can comprise a first heating block, a first heat control unit, a second heat control unit, and, optionally, a negative load device. The first heating block can comprise a first static heating zone, a heating zone partition, and a second static heating zone separated from the first static heating zone by the heating zone partition. The first heat control unit is operably associable with the first static heating zone. The second heat control unit is operably associable with the second static heating zone. The first temperature or temperature range, or the second temperature or temperature range, can be a temperature or temperature range sufficient to allow for denaturing of double-stranded nucleic acid, annealing of nucleic acids, or extension of nucleic acids, or any combination thereof. While a single heating block can be employed in the heating subassembly, use of a second, complementary heating block can provide additional temperature control and is particularly advantageous when two thermocycling plates are used. Accordingly, the heating subassembly of the present teachings can comprise a complementary heating block.

In some embodiments, a method of thermocycling is provided in accordance with the present teachings. The method can comprise one or more of the following steps, the order of which can be varied, or wherein one or more of the steps can be repeated. A source solution can be passed through a thermocycling plate comprising a plurality of regions. A hot start region corresponding to an initial fluid passage of the thermocycling plate can be heated and a denaturation region corresponding to a portion of a main fluid passage proximal a second partition of the thermocycling plate can be heated to a first temperature or temperature range. An annealing/extension region corresponding to a portion of the main fluid passage proximal a third partition of the thermocycling plate can be heated to a second temperature or temperature range. The sample fluid passed through the fluid passageway can comprise a water-in-oil emulsion comprising a plurality of aqueous polymerase chain reaction (PCR) reaction droplets.

In accordance yet other embodiments of the present teachings, a centrifuge subsystem is provided that is suitable for integration into an emulsion thermocycling system or equivalent device. The centrifuge can comprise a centrifuge housing, a motor comprising a rotor axle mounted in the housing motor aperture, and a rotor mounted on the rotor axle.

A fluid collection tube is provided that can comprise a main tube body and a tube extension. The main tube body can comprise a main body sidewall surrounding a tube interior with a tube opening at a first end, and a second end distal to the first end providing a sealed base. The tube extension can comprise a tube extension sidewall defining a fluid exit channel in fluid communication with the tube interior through a tube channel inlet proximal to the tube opening and extending to a tube channel outlet distal to the tube opening.

A fluid distribution device, also referred to herein as a "slinger," is provided by the present teachings. The slinger can comprise sidewalls defining a central channel comprising a first end, a central zone, and a second end along a longitudinal axis. Sidewall lateral extensions, also referred to as "wings" herein, can be provided extending away from the sidewalls on either side of the central channel. The wings are useful in mating with and ensuring a secure connection with a fluid distribution device receptacle of a centrifuge rotor. Rather than use an insertable/detachable slinger, a slinger can be employed that is permanently or integrally associated with the rotor housing.

A centrifuge rotor is provided by the present teachings, which is particularly suitable for separating water-in-oil emulsions and removing the oil phase of such an emulsion. The centrifuge rotor can comprise a rotor housing having a bisecting rotor axis perpendicular to a central rotor axis, a rotor basin formed by the rotor housing, a rotor basin floor, and a rotor basin sidewall lining the rotor housing basin and extending up toward a rotor top rim having an inner perimeter and an outer perimeter. The rotor can further comprise at least one collection tube receptacle comprising an opening formed in the basin sidewall, and at least one tube extension receptacle having a grove formed in the rotor top rim and extending from the inner perimeter to the outer perimeter. The rotor can also comprise at least one liquid distribution device (slinger) receptacle extending from the rotor basin floor and having a distribution device receptacle longitudinal axis.

A method of recovering a polymerase chain reaction (PCR) product from a water-in-oil emulsion is provided in accordance with the present teachings. The method can be performed using the centrifuge or centrifuge components of the present teachings. The method can comprise one or more of the following steps. At least one collection tube can be filled with an aqueous solution and inserted into a tube receptacle of a centrifuge rotor. At least one fluid distribution device (slinger) can also be inserted into a fluid distribution device receptacle of the centrifuge rotor. Sample fluid, which can comprise a PCR product in a water-in-oil emulsion, can be fed into the fluid distribution device. The centrifuge rotor is spun to deliver the sample fluid to the at least one collection tube, and the emulsion is partly or completely broken in the at least one collection tube. The centrifuge rotor motor can also be spun to remove an oil phase from the collection tube. The method can further comprise recovering PCR product from the at least one collection tube.

Taken together it will be appreciated that the disclosed systems and methods of the present teachings provide an enhanced mechanism by which to conduct PCR and ePCR reactions using easy to fabricate sample chambers with minimum operator interaction.

It is to be understood that although DNA is referred to often herein, the present teachings also apply to reactions with and emulsions containing RNA, PNA, other nucleic acid molecules, other template molecules, other reactants, or combinations thereof, instead of or in addition to DNA.

It is to be understood that each of the publications referenced herein is independently incorporated herein in its entirety by reference.

In a first aspect, a system for making membrane-based emulsion droplets includes an emulsion-generating device comprising a top channel gasket, a bottom channel gasket, an emulsion-generating membrane disposed between top channel gasket and bottom channel gasket, a first chamber defined between top channel gasket and emulsion-generating membrane, and a second chamber defined between emulsion-generating membrane and bottom channel gasket; a microreactor mixture supply in communication with the top channel gasket; a carrier fluid supply in communication with the bottom channel gasket; and an emulsion collection device in communication with the top or bottom channel gasket for collecting the membrane-based emulsion droplets; wherein the emulsion-generating membrane comprises at least two through holes.

In an example of the first aspect, each of the membrane-based emulsion droplets comprises a volume of a microreactor mixture at least partially surrounded by the carrier liquid, and the carrier liquid is immiscible with the microreactor mixture.

In another example of the first aspect and the above examples, the top channel gasket, the bottom channel gasket, and the emulsion-generating membrane are rigidly mounted in a container.

In a further example of the first aspect and the above examples, the top channel gasket comprises at least one flow path defined therein. For example, the at least one flow path is defined in a bottom surface of the top channel gasket. In another example, the at least one flow path comprises a first flow path and a second flow path.

In an additional example of the first aspect and the above examples, the bottom channel gasket comprises at least one flow path defined therein. For example, the at least one flow path is defined in a top surface of the top channel gasket. In another example, the at least one flow path comprises a third flow path, a fourth flow path, and a fifth flow path.

In an example of the first aspect and the above examples, at least some of the membrane-based emulsion droplets comprise a microreactor.

In another example of the first aspect and the above examples, the membrane-based emulsion droplets are uniformly sized.

In a further example of the first aspect and the above examples, the microreactor supply mixture and the carrier fluid supply are pressurized.

In an additional example of the first aspect and the above examples, the emulsion-generating membrane comprises a rubber material.

In an example of the first aspect and the above examples, the first chamber comprises a volume of microreactor mixture.

In another example of the first aspect and the above examples, the first chamber comprises a volume of microreactor mixture and at least one emulsion droplet.

In a further example of the first aspect and the above examples, the second chamber comprises a volume of carrier liquid.

In an additional example of the first aspect and the above examples, the second chamber comprises a volume of carrier liquid and at least one emulsion droplet.

In an example of the first aspect and the above examples, the top channel gasket comprises a first gasket port defined therethrough.

In another example of the first aspect and the above examples, the bottom channel gasket comprises a second gasket port and a third gasket port defined therethrough.

In a second aspect, a method of making membrane-based emulsion droplets includes mixing together an aqueous phase solution, a plurality of template beads, a library of templates from a sample, DNA polymerase, and a pair of primers, to form a microreactor mixture; forcing the microreactor mixture through at least two through holes of an emulsion-generating membrane in an emulsion-generating device, from a first chamber of the emulsion-generating device and into a carrier fluid disposed in a second chamber of the emulsion-generating device; forming a plurality of membrane-based emulsion droplets after the microreactor mixture passes through the at least two through holes of the emulsion-generating membrane from the first chamber of the emulsion-generating membrane and into the carrier fluid in the second chamber of the emulsion-generating membrane; and forcing the plurality of emulsion droplets in the second chamber through the at least two through holes of the emulsion-generating membrane into the first chamber.

In an example of the second aspect, each of the membrane-based emulsion droplets comprises a volume of a microreactor mixture at least partially surrounded by the carrier liquid, and the carrier liquid is immiscible with the microreactor mixture.

In another example of the second aspect and the above examples, the method further includes flowing the membrane-based emulsion droplets in at least one flow-path in the first chamber.

In a further example of the second aspect and the above examples, the method further includes flowing the membrane-based emulsion droplets in at least one flow-path in the second chamber.

In an additional example of the second aspect and the above examples, at least some of the membrane-based emulsion droplets comprise a microreactor having at least one template bead.

In an example of the second aspect and the above examples, the method further includes forcing the membrane-based emulsion droplets back and forth through the one or more through holes of the emulsion-generating membrane from the first and second chambers.

In another example of the second aspect and the above examples, the membrane-based emulsion droplets are uniformly sized.

In a third aspect, a device for making emulsion droplets includes a substrate comprising an emulsion-generating plate; a cover in contact with a top surface of the emulsion-generating plate; a flow cell defined between the emulsion-generating plate and the cover; at least two through holes extending through at least a portion of the emulsion-generating plate and in fluid communication with the flow cell, the at least two through holes being arranged in a line; a carrier fluid input port formed through the cover and in fluid communication with the flow cell; and an inverse emulsion outlet port formed through the cover and in fluid communication with the flow cell; wherein the line is arranged at least substantially perpendicularly with respect to a direction from the carrier fluid input port toward the inverse emulsion outlet port.

In an example of the third aspect, the device further includes a flow cell wall extending between a bottom of the flow cell to the cover.

In another example of the third aspect and the above examples, the device further includes a volume of carrier fluid in the flow cell, the carrier fluid comprising a non-aqueous liquid partially or completely immiscible in water.

In a further example of the third aspect and the above examples, the device further includes a cavity formed in or below the emulsion-generating plate, the cavity comprising a volume of microreactor mixture and being in fluid communication with the at least two through holes.

In an additional example of the third aspect and the above examples, the microreactor mixture comprises an aqueous phase solution, a plurality of template beads, a library of templates from a sample, DNA polymerase, and a pair of primers.

In an example of the third aspect and the above examples, the cavity is formed in the emulsion-generating plate.

In another example of the third aspect and the above examples, the at least two through holes comprises from about 50 to about 100 through holes.

In a further example of the third aspect and the above examples, the at least two through holes each has an inner diameter of from about 3 microns to about 15 microns.

In an additional example of the third aspect and the above examples, the flow cell comprises nozzles, one around each of the at least two through holes. For example, the at least two through holes comprises from about 50 to about 100 through holes. In another example, each nozzle comprises an inner diameter of from about 11 microns to about 18 microns.

In a fourth aspect, a method of making an inverse emulsion using the device of the first aspect and examples relating thereto includes flowing a pressurized volume of a microreactor mixture into the cavity, the microreactor mixture comprising an aqueous phase solution, a plurality of template beads, a library of templates from a sample, DNA polymerase, and a pair of primers; flowing a pressurized volume of a carrier fluid into the flow cell of the device; forcing the pressurized volume of microreactor mixture through the at least two through holes and into the carrier fluid in the flow cell; and forming a plurality of droplets of the microreactor mixture as the mixture passes through the at least two through holes and into the carrier fluid in the flow cell, thus forming an inverse emulsion.

In an example of the fourth aspect, each of the emulsion droplets comprises a volume of a microreactor mixture at least partially surrounded by the carrier liquid, and the carrier liquid is immiscible with the microreactor mixture.

In another example of the fourth aspect and the above examples, the method further includes forcing the inverse emulsion out of the device through the emulsion outlet port.

In a further example of the fourth aspect and the above examples, the forcing the pressurized volume of the microreactor mixture through the at least two through holes comprises forcing the microreactor mixture to flow in a direction that is perpendicular to the top surface of the emulsion-generating plate.

In an additional example of the fourth aspect and the above examples, the method further includes forcing the microreactor mixture through nozzles, one nozzle around each of the at least two through holes. For example, the flowing the pressurized volume of carrier fluid into the flow cell comprises forcing the pressurized volume of carrier fluid to flow in a direction that is perpendicular to the nozzles around the at least two through holes.

In an example of the fourth aspect and the above examples, the plurality of droplets of the microreactor mixture in the inverse emulsion are uniformly sized.

In a fifth aspect, an emulsion-generating device includes (a) a first channel plate, said first channel plate comprising (a1) a first fluid port comprising an orifice passing through said first channel plate in a thickness direction, and (a2) at least one first flow channel disposed on a bottom surface of said first channel plate; (b) a second channel plate, said second channel plate comprising (b1) a second fluid port comprising an orifice passing though said second channel plate in a thickness direction, and (b2) at least one second flow channel disposed on a top surface of said second channel plate; and (c) a first filter comprising a plurality of pores, wherein said first filter is disposed between said first channel plate and said second channel plate such that said emulsion-generating device comprises a first chamber comprising said bottom surface of said first channel plate and said first filter and a second chamber comprising said top surface of said second channel plate and said first filter.

In an example of the fifth aspect, said at least one first flow channel comprises two or more flow channels. For example, said two or more flow channels do not cross each other. In an example, at least two of said two or more flow channels cross each other.

In another example of the fifth aspect and the above examples, said at least one first flow channel comprises one or more flow channels not connecting to said first fluid port. For example, said two or more flow channels do not cross each other. In another example, at least two of said two or more flow channels cross each other.

In a further example of the fifth aspect and the above examples, said at least one second flow channel comprises a flow channel connecting to said second fluid port.

In an additional example of the fifth aspect and the above examples, said at least one second flow channel comprises one or more flow channels not connecting to said second fluid port.

In an example of the fifth aspect and the above examples, one of said first channel plate and said second channel plate further comprises a third fluid port comprising an orifice passing through said first or second channel plate in a thickness direction. For example, said at least one first or second flow channel comprises a flow channel connecting to said third fluid port. In an example, said at least one first and second flow channel comprises one or more flow channels not connecting to said third fluid port.

In another example of the fifth aspect and the above examples, the device further includes one or more second filters disposed between said first channel plate and said first filter or disposed between said second channel plate and said first filter, each said second filter comprising a plurality of pores.

In an additional example of the fifth aspect and the above examples, the device further includes one or more second filters disposed between said first channel plate and said first filter and one or more third filters disposed between said second channel plate and said first filter, said second and third filter comprising a plurality of pores.

In an example of the fifth aspect and the above examples, said plurality of pores have a size of about 1 to about 50 microns.

In another example of the fifth aspect and the above examples, said first filter is a membrane.

In a further example of the fifth aspect and the above examples, said first filter is a track-etched filter.

In an additional example of the fifth aspect and the above examples, said first filter is a laser-etched filter.

In an example of the fifth aspect and the above examples, the device further includes a housing, wherein said first channel plate, said second channel plate, and said first filter are mounted in said housing.

In another example of the fifth aspect and the above examples, said at least one first flow channel or said at least one second flow channel is configured to have low fluid resistance.

In a further example of the fifth aspect and the above examples, said at least one first flow channel or said at least one second flow channel is disposed such that fluid passes said first filter a plurality of times.

In an additional example of the fifth aspect and the above examples, said at least one first flow channel or said at least one second flow channel has a depth of not greater than 500 μm, and wherein said first chamber or said second chamber has a depth from said first or second channel plate to said first filter of not greater than 500 μm.

In a sixth aspect, a system for making emulsion droplets includes an emulsion-generating device comprising: (a) a first channel plate, said first channel plate comprising (a1) a first fluid port comprising an orifice passing through said first channel plate in a thickness direction, and (a2) at least one first flow channel disposed on a bottom surface of said first channel plate; (b) a second channel plate, said second channel plate comprising (b1) a second fluid port comprising an orifice passing though said second channel plate in a thickness direction, and (b2) at least one second flow channel disposed on a top surface of said second channel plate; and (c) a first filter comprising a plurality of pores, wherein said first filter is disposed between said first channel plate and said second channel plate such that said emulsion-generating device comprises a first chamber comprising said bottom surface of said first channel plate and said first filter and a second chamber comprising said top surface of said second channel plate and said first filter; a reaction mixture supply in fluid communication with said first chamber by way of said first fluid port; a carrier fluid supply in fluid communication with said second chamber by way of said second fluid port; and an emulsion collection device in fluid communication with said second chamber by way of said third fluid port.

In an example of the sixth aspect, said reaction mixture supply and said carrier fluid supply are pressurized.

In a seventh aspect, a method of making emulsion droplets in an emulsion-generating device includes (i) a first channel plate, said first channel plate comprising (i1) a first fluid port comprising an orifice passing through said first channel plate in a thickness direction, and (i2) at least one first flow channel disposed on a bottom surface of said first channel plate; (ii) a second channel plate, said second channel plate comprising (ii1) a second fluid port comprising an orifice passing though said second channel plate in a thickness direction, and (ii2) at least one second flow channel disposed on a top surface of said second channel plate; and (iii) a first filter comprising a plurality of pores, wherein said first filter is disposed between said first channel plate and said second channel plate such that said emulsion-generating device comprises a first chamber comprising said bottom surface of said first channel plate and said first filter and a second chamber comprising said top surface of said second channel plate and said first filter; said method comprising: (a) flowing a reaction mixture into said first fluid port of said emulsion-generating device; (b) flowing a carrier fluid into said second fluid port of said emulsion-generating device, wherein said carrier fluid is immiscible with said reaction mixture; and (c) recovering an emulsion fluid from said third fluid port, wherein said emulsion fluid comprises droplets of said reaction mixture in said carrier fluid.

In an example of the seventh aspect, said reaction mixture comprises a plurality of template beads, a plurality of templates, a DNA polymerase, and a pair of primers In another example of the seventh aspect and the above examples, the method further includes adjusting a fluid pressure of said reaction mixture or adjusting a fluid pressure of said carrier fluid such that said droplets of said reaction mixture in said carrier fluid in said step (c) have a predetermined size.

In an eighth aspect, a method of making emulsion droplets includes (a) passing a flow of reaction mixture and carrier fluid such that said reaction mixture passes through a filter from a first side to a second side and said carrier fluid flows, said filter comprising a plurality of pores, (b) creating a shear flow of a carrier fluid at said second side to generate a first emulsion comprising a plurality of first droplets of said reaction mixture in said carrier fluid, wherein said carrier fluid is immiscible with said reaction mixture; (c) passing a flow of said first emulsion through said filter from said second side to said first side; (d) creating a shear flow by said carrier fluid at said first side to generate a second emulsion comprising a plurality of second droplets of said reaction mixture in said carrier fluid; and (e) recovering said second emulsion fluid.

In a ninth aspect, am emulsion-generating device includes a first plate and a second plate configured to form a flow chamber; a fluid input port and a fluid output port in fluid communication with said flow chamber; at least said first or second plate comprising a plurality of through holes passing through said first or second plate in a plate thickness direction; said plurality of through holes being disposed in one or more lines oriented at a substantially perpendicular direction with respect to a direction from said fluid input port toward said fluid outlet port.

In an example of the ninth aspect, said first plate is a top plate and said second plate is a bottom plate, and wherein said bottom plate comprises said plurality of through holes.

In another example of the ninth aspect and the above examples, said plurality of through holes comprises from about 50 to about 100 through holes. For example, said plurality of through holes each has an inner diameter of from about 3 microns to about 15 microns.

In a further example of the ninth aspect and the above examples, the device further includes a respective elevated rim around each of said through hole.

In an additional example of the ninth aspect and the above examples, each said elevated rim has an inner diameter from about 11 microns to about 18 microns.

In a tenth aspect, a system for making emulsion droplets includes the emulsion-generating device of the ninth aspect and its associated examples; a reaction mixture supply in fluid communication with said flow chamber by way of said plurality of through holes; a carrier fluid supply in fluid communication with said flow chamber by way of said fluid inlet port; and an emulsion collection device in fluid communication with said flow chamber by way of said outlet fluid port.

In an example of the tenth aspect, said reaction mixture supply and said carrier fluid supply are pressurized.

In another example of the tenth aspect and the above example, said reaction mixture supply includes a sample tube.

In an eleventh aspect, a method of making an inverse emulsion includes providing a reaction mixture, a carrier fluid, and a device of the ninth aspect and associated examples, wherein said carrier fluid is immiscible with said reaction mixture; flowing a reaction mixture into said flow chamber through said through holes; flowing a carrier fluid into said flow chamber through said fluid inlet; and forming a plurality of droplets of said reaction mixture in said carrier fluid, thus forming an inverse emulsion.

In an example of the eleventh aspect, the reaction mixture comprises an aqueous phase solution, a plurality of template beads, a library of templates from a sample, DNA polymerase, and a pair of primers.

In another example of the eleventh aspect and the above examples, the method further includes recovering said inverse emulsion from said fluid outlet port.

In a further example of the eleventh aspect and the above examples, the method further includes adjusting a fluid pressure of said reaction mixture or adjusting a fluid pressure of said carrier fluid such that said droplets of said reaction mixture in said carrier fluid have a predetermined size.

In a twelfth aspect, a sample reaction plate includes a slab housing having a width, a length, and a thickness less than both the width and the length, and comprising a plurality of corners comprising a first corner, a second corner, a third corner, and a fourth corner, a plurality of edges comprising a first edge extending from the first corner to the second corner, a second edge extending from the second corner to the third corner, a third edge extending from the third corner to the fourth corner, and a fourth edge extending from the fourth corner to the first corner; a plurality of partitions extending across the width and comprising a first partition proximal the first edge, a second partition between the first partition and a third partition, and the third partition proximal the third edge; and a fluid passageway disposed in the housing, said fluid passageway comprising an inlet proximal the first corner, an initial fluid passage in fluid communication with the inlet and extending to proximal the second corner along the width of the slab housing, between the first partition and the second partition, a transition fluid passage in fluid communication with the initial fluid passage and extending from proximal the second corner to proximal the third corner along the length of the slab housing, a main fluid passage in fluid communication with the transition fluid passage, extending from proximal the third corner to proximal the fourth corner along the width of the slab housing, comprising a plurality of repeats between the second partition and the third partition, and having a tortuous shape, and an outlet in fluid communication with the main fluid passage.

In an example of the twelfth aspect, the second partition is parallel to at least one of the first partition and the third partition.

In another example of the twelfth aspect and the above examples, the distance between the second and third partitions is greater than the distance between the first and second partitions.

In a further example of the twelfth aspect and the above examples, the distance between the second and third partitions is at least five times greater than the distance between the first and second partitions.

In an additional example of the twelfth aspect and the above examples, the distance between the second and third partitions is at least ten times greater than the distance between the first and second partitions.

In an example of the twelfth aspect and the above examples, the initial fluid passage has a tortuous shape and comprises a plurality of repeats between the first partition and the second partition.

In another example of the twelfth aspect and the above examples, the initial fluid passage has a tortuous shape and comprises: a plurality of repeats between the first partition and the second partition formed by a plurality of initial straight members, and a plurality of initial turn members joining the initial straight members at the first and second partitions; and the main fluid passage comprising said plurality of repeats between the second partition and the third partition formed by a plurality of main straight members, and a plurality of main turn members joining the main straight members at the second and third partitions. For example, the main straight members are longer than the initial straight members. In an example, the main straight members are at least five times longer than the initial straight members. In another example, the main straight members are at least ten times longer than the initial straight members.

In a further example of the twelfth aspect and the above examples, the main fluid passage comprises from about 5 to about 500 repeats between the second partition and the third partition.

In an additional example of the twelfth aspect and the above examples, the main fluid passage comprises from about 10 to about 100 repeats between the second partition and the third partition.

In an example of the twelfth aspect and the above examples, the initial fluid passage comprises from about 10 repeats to about 100 repeats between the first partition and the second partition.

In another example of the twelfth aspect and the above examples, the method further includes an exit fluid passage in fluid communication with the main fluid passage and extending from proximal the fourth corner to proximal the first corner along the length of the slab housing, and wherein the outlet is proximal the first corner in fluid communication with the exit fluid passage.

In a further example of the twelfth aspect and the above examples, at least one initial turn member or main turn member has an average cross-section area less than an average cross-section area of an adjacent initial straight member or adjacent main straight member. For example, a plurality of the initial turn members along the second partition each have an average cross-sectional area less than the average cross-sectional area of an adjacent initial straight member. In another example, a plurality of the main turn members along the third partition each have an average cross-sectional area less than the average cross-sectional area of an adjacent initial straight member. In a further example, a plurality of the initial turn members along the first partition each have an average cross-sectional area less than the average cross-sectional area of an adjacent initial straight member. In an additional example, a plurality of the main turn members along the second partition each have an average cross-sectional area less than the average cross-sectional area of an adjacent initial straight member.

In an additional example of the twelfth aspect and the above examples, the plate further includes a first face bounded by the plurality of edges and plurality of corners; and a second face parallel to the first face; bounded by the plurality of edges and plurality of corners; wherein the inlet and outlet are comprised by the first face or the second face.

In a thirteenth aspect, a pair of thermocycling plates includes a first thermocycling plate corresponding to the thermocycling plate of the twelfth aspect and associated examples; and a second thermocycling plate comprising a mirror-image configuration of the thermocycling plate.

In a fourteenth aspect, a heating subassembly includes a first heating block comprising a first static heating zone, a heating zone partition, and a second static heating zone separated from the first static heating zone by the heating zone partition; a first heat control unit operably associated with the first static heating zone; a second heat control unit operably associated with the second static heating zone; and a power source electrically associated with the first and second heat control units.

In an example of the fourteenth aspect, the subassembly further includes a negative load device operably associated with the second heat control unit and the second static heating zone. For example, the first heat control unit is configured to maintain the first static heating zone at a first temperature or within in a first temperature range; the second heat control unit is configured to maintain the first static heating zone at a second temperature or within in a second temperature range; and the first temperature is higher than the second temperature, and the first temperature range is higher than second temperature range. In another example, the first temperature range does not overlap with the second temperature range. In a particular example, the first temperature or temperature range differs by at least 10° C. from the second temperature or temperature range. In another example, the first temperature range is from about 85° C. to about 100° C.; and the second temperature range is from about 45° C. to about 75° C.

In another example of the fourteenth aspect and the above examples, the negative load device comprises a fan.

In a further example of the fourteenth aspect and the above examples, the subassembly further includes a recess configured to allow passage of a sample reaction plate inlet, a sample reaction plate outlet, or tubing associated with at least one of the inlet and the outlet, or any combination thereof.

In an additional example of the fourteenth aspect and the above examples, the subassembly further includes a complementary heating block comprising: a first complementary static heating zone; a complementary heating zone partition; and a second complementary static heating zone separated from the first complementary static heating zone by the complementary heating zone partition. For example, the complementary heating block comprises: a first complementary heat control unit operably associated with the first complementary static heating zone; a second complementary heat control unit operably associated with the second complementary static heating zone; and a complementary negative load device operably associated with the second complementary heat control unit and the second complementary static heating zone. In an example, the second heating block is electrically associated with the second first and second complementary heat control units.

In a fifteenth aspect, an amplification system includes a first sample reaction plate comprising a slab housing having a width, a length, and a thickness less than both the width and the length, and comprising a plurality of corners comprising a first corner, a second corner, a third corner, and a fourth corner, a plurality of edges comprising a first edge extending from the first corner to the second corner, a second edge extending from the second corner to the third corner, a third edge extending from the third corner to the fourth corner, and a fourth edge extending from the fourth corner to the first corner; a plurality of partitions extending across the width and comprising a first partition proximal the first edge, a second partition between the first partition and a third partition, and the third partition proximal the third edge, and a fluid passageway disposed in the housing and comprising an inlet proximal the first corner, an initial fluid passage in fluid communication with the inlet and extending to proximal the second corner along the width of the slab housing, between the first partition and the second partition, a transition fluid passage in fluid communication with the initial fluid passage and extending from proximal the second corner to proximal the third corner along the length of the slab housing, a main fluid passage in fluid communication with the transition fluid passage, extending from proximal the third corner to proximal the fourth corner along the width of the slab housing, comprising a plurality of repeats between the second partition and the third partition, and having a tortuous shape, and an outlet in fluid communication with the main fluid passage; and a heating subassembly comprising a first heating block comprising a first static heating zone, a heating zone partition, and a second static heating zone separated from the first static heating zone by the heating zone partition, a first heat control unit operably associated with the first static heating zone, a second heat control unit operably associated with the second static heating zone, wherein the first sample reaction plate and first heating block are adjacent, parallel, and in thermal communication with each other, with the first static heating zone in alignment with a hot start region corresponding to the initial fluid passage and a denaturation region corresponding to a portion of the main fluid passage proximal the second partition, and the second static heating zone in alignment with an annealing/extension region corresponding to a portion of the main fluid passage proximal the third partition.

In an example of the fifteenth aspect, the system further includes a negative load device operably associated with the second heat control unit and the second static heating zone.

In another example of the fifteenth aspect and the above examples, the system further includes a complementary heating block comprising: a first complementary static heating zone; a complementary heating zone partition; and a second complementary static heating zone separated from the first complementary static heating zone by the complementary heating zone partition; wherein the first sample reaction plate and complementary heating block are adjacent, parallel, and in thermal communication with each other, the first complementary static heating zone in alignment with a hot start region corresponding to the initial fluid passage and a denaturation region corresponding to a portion of the main fluid passage proximal the second partition, and the second complementary static heating zone in alignment with an annealing/extension region corresponding to a portion of the main fluid passage proximal the third partition.

In another example of the fifteenth aspect and the above examples, the system further includes a second sample reaction plate comprising the same characteristics of the first sample reaction plate; and a complementary heating block comprising a first complementary static heating zone, a complementary heating zone partition, and a second complementary static heating zone separated from the first complementary static heating zone by the complementary heating zone partition; wherein the first and second sample reaction plates are adjacent to one another, and the second sample reaction plate and complementary heating block are adjacent, parallel, and in thermal communication with each other, the first complementary static heating zone in alignment with a hot start region corresponding to the initial fluid passage of the second sample reaction plate and a denaturation region corresponding to a portion of the main fluid passage proximal the second partition of the second sample reaction plate, and the second complementary static heating zone in alignment with an annealing/extension region corresponding to a portion of the main fluid passage proximal the third partition of the second sample reaction plate.

In a further example of the fifteenth aspect and the above examples, the system further includes a gasket adjacent to at least three sides of each of the first sample reaction plate and the first heating block.

In an additional example of the fifteenth aspect and the above examples, the system further includes a gasket adjacent to at least three sides of each of the first sample reaction plate, the second sample reaction plate, the first heating block, and the complementary heating block.

In a sixteenth example, a method of thermocycling includes passing a sample fluid through a sample reaction plate comprising a plurality of regions; heating a hot start region corresponding to an initial fluid passage of the sample reaction plate and heating a denaturation region corresponding to a portion of a main fluid passage proximal a second partition of the sample reaction plate to a first temperature or temperature range; heating an annealing/extension region corresponding to a portion of the main fluid passage proximal a third partition of the sample reaction plate to a second temperature or temperature range; wherein the first temperature is higher than the second temperature, and the first temperature range is higher than second temperature range, and wherein the sample reaction plate comprises a slab housing having a width, a length, and a thickness less than both the width and the length, and comprising a plurality of corners comprising a first corner, a second corner, a third corner, and a fourth corner, a plurality of edges comprising a first edge extending from the first corner to the second corner, a second edge extending from the second corner to the third corner, a third edge extending from the third corner to the fourth corner, and a fourth edge extending from the fourth corner to the first corner, a plurality of partitions extending across the width and comprising a first partition proximal the first edge, a second partition between the first partition and a third partition, and the third partition proximal the third edge; and a fluid passageway disposed in the housing and comprising an inlet proximal the first corner, an initial fluid passage in fluid communication with the inlet and extending to proximal the second corner along the width of the slab housing, between the first partition and the second partition, a transition fluid passage in fluid communication with the initial fluid passage and extending from proximal the second corner to proximal the third corner along the length of the slab housing, a main fluid passage in fluid communication with the transition fluid passage, extending from proximal the third corner to proximal the fourth corner along the width of the slab housing, comprising a plurality of repeats between the second partition and the third partition, and having a tortuous shape, and an outlet in fluid communication with the main fluid passage wherein said passing said fluid through said sample reaction plate comprises feeding said fluid into said inlet.

In an example of the sixteenth aspect, the sample fluid comprises a water-in-oil emulsion comprising a plurality of aqueous polymerase chain reaction (PCR) reaction droplets.

In another example of the sixteenth aspect and the above examples, the method further includes annealing a sample nucleic acid in the reactor droplet to a template in the reactor droplet; extending the sample nucleic acid to form a double-stranded nucleic acid; and denaturing the double-stranded nucleic acid.

In an additional example of the sixteenth aspect and the above examples, the method further includes sending PCR product from the outlet to a centrifuge for recovery of the PCR product.

In a seventeenth aspect, a fluid collection tube includes a main tube body comprising a main body housing surrounding a tube interior comprising a tube opening at a first end, and a second end distal to the first end providing a sealed base; and a tube extension comprising a tube extension sidewall defining a fluid exit channel in fluid communication with the tube interior through a tube channel inlet proximal to the tube opening and extending to a tube channel outlet distal to the tube opening.

In an example of the seventeenth aspect, the tube further includes a tube lip disposed about the perimeter of the tube opening and allowing fluid communication of the tube exit channel with the tube interior.

In another example of the seventeenth aspect and the above examples, the tube further includes a tube buttress disposed between the tube extension sidewall and the main tube housing.

In an additional example of the seventeenth aspect and the above examples, the tube extension sidewall and the main tube housing are positioned at an angle of from about 15° to about 90° to each other.

In a further example of the seventeenth aspect and the above examples, the tube extension sidewall and the main tube housing are positioned at an angle of from about 30° to about 60° relative to each other.

In an example of the seventeenth aspect and the above examples, the main tube body comprises a generally cylindrical portion proximal the first end, a conically tapered portion proximal the second end, and a rounded second end.

In another example of the seventeenth aspect and the above examples, the tube exit channel and tube extension sidewall have a U-shaped cross-section along a longitudinal axis.

In a further example of the seventeenth aspect and the above examples, an average cross-sectional area of the exit tube channel is less than an average cross-sectional area of the tube interior.

In an additional example of the seventeenth aspect and the above examples, the average cross-sectional area of the exit tube channel is less than about 25% of the average cross-sectional area of the tube interior.

In an example of the seventeenth aspect and the above examples, the tube further includes a cap.

In an eighteenth aspect, a fluid distribution device includes sidewalls defining a central channel comprising a first end, a central zone, and a second end along a longitudinal axis; wings extending away from the sidewalls on either side of the central channel; a first spout extending from the central zone to the first end and terminating at a first spout outlet, the sidewalls tapering along the central zone toward the first spout; and a second spout extending from the central zone to the second end and terminating at a second spout outlet, the sidewalls tapering along the central zone toward the second spout.

In an example of the eighteenth aspect, the device is configured to mate with a fluid distribution device receptacle of a centrifuge rotor.

In a nineteenth aspect, a centrifuge rotor includes a rotor housing having a bisecting rotor axis perpendicular to a central rotor axis; a rotor basin formed by the rotor housing; a rotor basin floor; a rotor basin sidewall lining the rotor housing basin and extending up toward a rotor top rim having an inner perimeter and an outer perimeter; at least one collection tube receptacle comprising an opening formed in the basin sidewall; at least one tube extension receptacle comprising a grove formed in the rotor top rim and extending from the inner perimeter to the outer perimeter; and at least one liquid distribution device receptacle extending from the rotor basin floor and having a distribution device receptacle longitudinal axis.

In an example of the nineteenth aspect, the collection tube receptacle opening and the tube extension groove are positioned at an angle of from about 15° to about 90° relative to each other.

In another example of the nineteenth aspect and the above examples, the collection tube receptacle opening and the tube extension groove are positioned at an angle of from about 30° to about 60° relative to each other.

In a further example of the nineteenth aspect and the above examples, the fluid distribution device receptacle comprises opposing sidewalls on either side of the distribution device receptacle longitudinal axis.

In an additional example of the nineteenth aspect and the above examples, the bisecting rotor axis is not parallel to the distribution device receptacle longitudinal axis. For example, the axes are positioned from about 0.15° to about 15.0° relative to each other. In another example, the axes are positioned from about 0.5° to about 5.0° relative to each other.

In an example of the nineteenth aspect and the above examples, the sidewalls comprise a substantially flat inset region about the collection tube receptacle and adjacent the tube receptacle opening.

In another example of the nineteenth aspect and the above examples, the rotor includes first and second tube receptacles positioned opposite each other along the bisecting rotor axis; and first and second tube extension grooves opposite each other along the bisecting rotor axis.

In a twentieth aspect, a centrifuge includes a centrifuge housing comprising centrifuge housing sidewalls extending from a base portion to a top portion comprising a top housing rim surrounding a top housing aperture, a lid operably associable with the top housing rim, a housing bottom recess extending from the base to an interior of the centrifuge housing and comprising bottom recess sidewalls and a bottom recess ceiling, a housing basin defined by the top housing rim, the top housing aperture, and housing basin sidewalls surrounding a receiving platform, and a housing motor aperture configured to accept a motor through the bottom recess ceiling and the receiving platform; a motor comprising a rotor axle and mounted in the housing motor aperture; and a rotor mounted on the rotor axle and comprising a rotor housing having a bisecting rotor axis perpendicular to a central rotor axis; a rotor basin formed by the rotor housing; a rotor basin floor; a rotor basin sidewall lining the rotor housing basin and extending up from the rotor basin floor toward a rotor top rim having an inner perimeter and an outer perimeter; at least one collection tube receptacle comprising an opening formed in the basin sidewall; at least one tube extension receptacle having a grove formed in the rotor top rim and extending from the inner perimeter to the outer perimeter; and at least one liquid distribution device (slinger) receptacle extending from the rotor basin floor and having a distribution device receptacle longitudinal axis.

In an example of the twentieth aspect, the centrifuge further includes a housing hinge assembly including a housing hinge plate operatively connectable to the centrifuge housing and comprising a top plate portion; first and second hinge receiving arms extending from the top plate portion and comprising respective first and second hinge axle apertures; and a hinge axle extending from the first and second hinge axle apertures and passing through a lid hinge portion extending from the lid.

In another example of the twentieth aspect and the above examples, the lid further comprises a top lid surface and a bottom lid surface; a central lid aperture extending from the top lid surface to the bottom lid surface; wherein the central lid aperture is configured to accept a fluid supply line and positioned above the fluid distribution device when the lid is in a closed configuration. For example, the centrifuge further includes a fluid supply source in fluid communication with the fluid supply line; and a fluid supply pump configured to pump fluid from the fluid supply source, through the fluid supply line and into the centrifuge.

In a further example of the twentieth aspect and the above examples, the centrifuge further includes a peripheral gutter comprising: a gutter housing providing a top gutter surface, a bottom gutter surface, and gutter sidewalls extending between the top and bottom gutter surfaces along an outer gutter perimeter of the gutter housing; a gutter inlet along an inner perimeter of the gutter housing; and a gutter flange extending around the gutter outer perimeter and adapted for placement on the top housing rim. For example, the centrifuge further includes a gutter outlet in the gutter housing; a housing drainage aperture in the housing sidewall; a basin drainage aperture in the housing basin sidewall; and drainage tubing operatively associated with the gutter outlet and passing through the drainage apertures.

In a twenty-first aspect, a method of recovering a polymerase chain reaction (PCR) product from a water-in-oil emulsion includes filling at least one collection tube with an aqueous solution; inserting the at least one collection tube into a tube receptacle of a centrifuge rotor; inserting at least one fluid distribution device (slinger) into a fluid distribution device receptacle of the centrifuge rotor; feeding sample fluid comprising an emulsion into the fluid distribution device; spinning the centrifuge rotor to deliver the sample fluid to the at least one collection tube; breaking the emulsion in the at least one collection tube; and spinning the centrifuge rotor to remove an oil phase from the collection tube.

In an example of the twenty-first aspect, the emulsion comprises a water-in-oil emulsion In another example of the twenty-first aspect and the above examples, the aqueous solution comprises at least one of a surfactant and a detergent. For example, the aqueous solution comprises sodium dodecyl sulfate. In another example, the aqueous solution further comprises ethanol.

In a further example of the twenty-first aspect and the above examples, the at least one collection tube comprises at least one mixing ball capable of capturing PCR product associated beads.

In an additional example of the twenty-first aspect and the above examples, the method further includes collecting the oil phase in a peripheral gutter.

In an example of the twenty-first aspect and the above examples, the sample fluid comprises a PCR product and further comprising recovering PCR product from the at least one collection tube.

In another example of the twenty-first aspect and the above examples, the fluid distribution device is inserted such that at least one fluid distribution outlet is displaced off center from a center of the at least one collection tube; and the spinning occurs in the direction of the displacement. For example, a degree of the displacement is relative to at least one of an angular velocity and an angular acceleration of the spinning rotor. In an example, the degree of the displacement results in sample fluid entering the at least one collection tube at or near a center of the tube.

In a further example of the twenty-first aspect and the above examples, the method further includes mixing the contents of the at least one collection tube by alternating the direction of the spinning rotor.

In an twenty-second aspect, a centrifuge includes a rotor comprising a rotor housing having a bisecting rotor axis perpendicular to a central rotor axis; a rotor basin formed by the rotor housing; a rotor basin floor; a rotor basin sidewall lining the rotor housing basin and extending up from the rotor basin floor toward a rotor top rim having an inner perimeter and an outer perimeter; at least one collection tube receptacle comprising an opening formed in the basin sidewall; at least one tube extension receptacle having a grove formed in the rotor top rim and extending from the inner perimeter to the outer perimeter; and at least one liquid distribution device (slinger) receptacle extending from the rotor basin floor and having a distribution device receptacle longitudinal axis.

In an example of the twenty-second aspect, the centrifuge further includes a centrifuge housing comprising centrifuge housing sidewalls extending from a base portion to a top portion comprising a top housing rim surrounding a top housing aperture, a lid operably associable with the top housing rim, a housing bottom recess extending from the base to an interior of the centrifuge housing and comprising bottom recess sidewalls and a bottom recess ceiling, a housing basin defined by the top housing rim, the top housing aperture, and housing basin sidewalls surrounding a receiving platform, and a housing motor aperture configured to accept a motor through the bottom recess ceiling and the receiving platform; a motor comprising a rotor axle and mounted in the housing motor aperture; wherein said rotor is mounted on the rotor axle. For example, the centrifuge further includes a housing hinge assembly comprising: a housing hinge plate operatively connectable to the centrifuge housing and comprising a top plate portion; first and second hinge receiving arms extending from the top plate portion and comprising respective first and second hinge axle apertures; and a hinge axle extending from the first and second hinge axle apertures and passing through a lid hinge portion extending from the lid.

In another example of the twenty-second aspect and the above examples, the lid further comprises: a top lid surface and a bottom lid surface; a central lid aperture extending from the top lid surface to the bottom lid surface; wherein the central lid aperture is configured to accept a fluid supply line and positioned above the fluid distribution device when the lid is in a closed configuration. For example, the centrifuge further includes a fluid supply source in fluid communication with the fluid supply line; and a fluid supply pump configured to pump fluid from the fluid supply source, through the fluid supply line and into the centrifuge.

In a further example of the twenty-second aspect and the above examples, the centrifuge further includes a peripheral gutter comprising: a gutter housing providing a top gutter surface, a bottom gutter surface, and gutter sidewalls extending between the top and bottom gutter surfaces along an outer gutter perimeter of the gutter housing; a gutter inlet along an inner perimeter of the gutter housing; and a gutter flange extending around the gutter outer perimeter and adapted for placement on the top housing rim. For example, the centrifuge further includes a gutter outlet in the gutter housing; a housing drainage aperture in the housing sidewall; a basin drainage aperture in the housing basin sidewall; and drainage tubing operatively associated with the gutter outlet and passing through the drainage apertures.

In a twenty-third aspect a method of separating a product in an aqueous phase from an inverse emulsion comprising an aqueous phase and a water immiscible phase using a centrifuge including a rotor comprising a rotor housing having a bisecting rotor axis perpendicular to a central rotor axis; a rotor basin formed by the rotor housing; a rotor basin floor; a rotor basin sidewall lining the rotor housing basin and extending up from the rotor basin floor toward a rotor top rim having an inner perimeter and an outer perimeter; at least one collection tube receptacle comprising an opening formed in the basin sidewall, wherein said collection tube receptacle containing a collection tube filled with an aqueous solution; at least one tube extension receptacle having a grove formed in the rotor top rim and extending from the inner perimeter to the outer perimeter; and at least one liquid distribution device (slinger) receptacle extending from the rotor basin floor and having a distribution device receptacle longitudinal axis, wherein said liquid distribution device receptacle containing a liquid distribution device, the method comprising: feeding a sample fluid comprising said inverse emulsion into the fluid distribution device; spinning the centrifuge rotor to deliver the sample fluid to the at least one collection tube and to remove said water immiscible phase from the collection tube, wherein the emulsion is broken in the at least one collection tube.

In an example of the twenty-third aspect, the method further includes, prior to said step of feeding sample fluid, inserting a collection tube into said tube receptacle; and inserting a fluid distribution device (slinger) into said fluid distribution device receptacle.

In another example of the twenty-third aspect and the above examples, the inverse emulsion comprises a water-in-oil emulsion.

In a further example of the twenty-third aspect and the above examples, the aqueous solution comprises at least one of a surfactant and a detergent. For example, the aqueous solution comprises sodium dodecyl sulfate.

In an additional example of the twenty-third aspect and the above examples, the aqueous solution further comprises ethanol.

In an example of the twenty-third aspect and the above examples, the at least one collection tube comprises at least one mixing ball capable of capturing PCR product associated beads.

In another example of the twenty-third aspect and the above examples, the method further includes collecting the water immiscible phase of said inverse emulsion in a peripheral gutter.

In a further example of the twenty-third aspect and the above examples, the sample fluid comprises a PCR product and said method further comprising recovering PCR product from the at least one collection tube.

In an additional example of the twenty-third aspect and the above examples, the fluid distribution device is inserted such that at least one fluid distribution outlet is displaced off center from a center of the at least one collection tube; and the spinning occurs in the direction of the displacement. For example, a degree of the displacement is relative to at least one of an angular velocity and an angular acceleration of the spinning rotor. In another example, the degree of the displacement results in sample fluid entering the at least one collection tube at or near a center of the tube.

In an example of the twenty-third aspect and the above examples, the method further includes mixing the contents of the at least one collection tube by alternating the direction of the spinning rotor.

In another example of the twenty-third aspect and the above examples, the method further includes performing said feeding said sample fluid into the fluid distribution device and said spinning the centrifuge rotor continuously.

In a twenty-fourth aspect, an emulsion generating device includes a first gasket including a first set of channels; a second gasket including a second set of channels complementary to the first set of channels, a carrier fluid inlet and an emulsion outlet fluidically coupled to the second set of channels; and a membrane disposed between the first and second gaskets, wherein fluid is to pass through the membrane at least three times when traversing the first and second sets of channels between the carrier fluid inlet and the emulsion outlet.

In an example of the twenty-fourth aspect, the first and second sets of channels are concurrently complementary.

In another example of the twenty-fourth aspect and the above examples, the first and second set of channels are countercurrently complementary.

In a further example of the twenty-fourth aspect and the above examples, the membrane comprises laser etched holes.

In an additional example of the twenty-fourth aspect and the above examples, the depth of the first or second set of channels is not greater than 500 micrometers.

In an example of the twenty-fourth aspect and the above examples, the device further includes a housing, the first and second channel gasket and the membrane disposed within the housing. For example, the housing defines a carrier fluid inlet port in fluidic communication with the carrier fluid inlet of the second gasket and defines an emulsion outlet port in fluid communication with the emulsion outlet of the second gasket. In another example, the housing defines a sample tube receptacle. In a further example, the housing further defines a displacement fluid inlet port in fluid communication with the sample tube receptacle. In an additional example, the device further includes a sample fluid tube.

In a twenty-fifth aspect, an emulsion generating system includes an emulsion generating device comprising: a housing defining a sample inlet port, a carrier fluid inlet port, an emulsion outlet port, and a displacement fluid inlet port; first and second channel gaskets; and a membrane disposed between the first and second channel gaskets; and a sample tube disposed on the sample inlet port and in fluid communication with the displacement fluid inlet port.

In an example of the twenty-fifth aspect, the carrier fluid inlet port and the emulsion outlet port are disposed on a lower surface of the housing.

In another example of the twenty-fifth aspect and the above examples, the sample inlet port is disposed on an upper surface of the housing. For example, the displacement fluid port is disposed on the upper surface of the housing. In another example, the displacement fluid port is disposed on a lower surface of the housing, a passageway defined between the displacement fluid port and the sample tube through the first and second channel gaskets and the membrane.

In a further example of the twenty-fifth aspect and the above examples, the first and second channel gaskets define a first set and a second set of complementary channels. For example, the first and second set of complementary channels are concurrently complementary. In another example, the first and second set of complementary channels are countercurrently complementary. In an additional example, the first and second set of complementary channels have a depth of not greater than 500 micrometers.

In a twenty-sixth aspect, a method of generating an emulsion includes applying an aqueous sample solution to the sample tube of the emulsion generating system of the twenty-fifth aspect and associated examples, applying a displacement fluid through the displacement fluid inlet port; applying a carrier fluid through the carrier fluid inlet port; and collecting an emulsion through the emulsion outlet port.

In an example of the twenty-sixth aspect, the displacement fluid and the carrier fluid comprise an oil.

In another example of the twenty-sixth aspect and the above examples, the displacement fluid displaces the aqueous sample fluid from the sample tube.

In a twenty-eighth aspect, a thermocycling device includes a plate comprising an inlet port and an outlet port and defining a first channel on a first side of the plate and a second channel on a second side of the plate; and first face piece to engage the first channel to define a first fluid pathway; and a second face piece to engage the second channel to define a second fluid pathway, the first fluid pathway in fluid communication with the second fluid pathway and with the inlet port and the outlet port.

In an example of the twenty-eighth aspect, the first and second face piece comprise films.

In another example of the twenty-eighth aspect and the above examples, the film has a thickness of not greater than 1000 micrometers.

In an additional example of the twenty-eighth aspect and the above examples, the film comprises a metal layer.

In another example of the twenty-eighth aspect and the above examples, the film is polymeric.

In a further example of the twenty-eighth aspect and the above examples, the device further includes a third channel on the first side of the plate and a fourth fluid channel on the second side of the plate, the third and fourth channels cooperative with the first and second face pieces to define third and fourth fluid pathways in fluid communication with the first and second fluid pathways.

In a twenty-ninth aspect, a thermocycling system includes a thermocycling device of the twenty-eighth aspect and associated examples; and a first heat plate in proximity to the first fluid pathway and defining a first heating zone; and a second heat plate in proximity to the second fluid pathway and defining a second heating zone.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, as illustrated by the range of from 1 to 5.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. An emulsion generating device comprising:

a first gasket including a first set of channels;

a second gasket including a second set of channels complementary to the first set of channels, a carrier fluid inlet and an emulsion outlet fluidically coupled to the second set of channels; and a membrane disposed between the first and second gaskets, wherein the first set of channels and second set of channels are complementary and align to permit fluid flow from a first channel of the first set of channels to a first channel of the second set of channels, from the first channel of the second set of channels to a second channel of the first set of channels, and from the second channel of the first set of channels to a second channel of the second set of channels, and wherein fluid is to pass through the membrane at least three times when traversing the first and second sets of channels between the carrier fluid inlet and the emulsion outlet.

2. The emulsion generating device of claim 1, wherein the first and second sets of channels are concurrently complementary.

3. The emulsion generating device of claim 1, wherein the first and second sets of channels are countercurrently complementary.

4. The emulsion generating device of claim 1, wherein the membrane comprises laser etched holes.

5. The emulsion generating device of claim 1, wherein a depth of at least one of the first and second sets of channels is not greater than 500 micrometers.

6. The emulsion generating device of claim 1, further comprising a housing, the first and second channel gasket and the membrane disposed within the housing.

7. The emulsion generating device of claim 6, wherein the housing defines a carrier fluid inlet port in fluidic communication with the carrier fluid inlet of the second gasket and defines an emulsion outlet port in fluidic communication with the emulsion outlet of the second gasket.

8. The emulsion generating device of claim 6, wherein the housing defines a sample tube receptacle.

9. The emulsion generating device of claim 8, wherein the housing further defines a displacement fluid inlet port in fluidic communication with the sample tube receptacle.

10. The emulsion generating device of claim 8, further comprising a sample fluid tube.

11. An emulsion generating system comprising:

an emulsion generating device comprising:

a housing defining a sample inlet port, a carrier fluid inlet port, an emulsion outlet port, and a displacement fluid inlet port;

a first gasket including a first set of channels;

a second gasket including a second set of channels complementary to the first set of channels, a carrier fluid inlet and the emulsion outlet port fluidically coupled to the second set of channels; and a membrane disposed between the first and second gaskets, wherein the first set of channels includes at least two channels each having at least two portions and the second set of channels includes at least three channels each having at least two portions, and wherein the first gasket and the second gasket are aligned such that each channel in the first set of channels has one portion overlapping one of the channels in the second set of channels and another portion overlapping a different one of the channels in the second set of channels; and a sample tube disposed on the sample inlet port and in fluidic communication with the displacement fluid inlet port.

12. The emulsion generating system of claim 11, wherein the carrier fluid inlet port and the emulsion outlet port are disposed on a lower surface of the housing.

13. The emulsion generating system of claim 11, wherein the sample inlet port is disposed on an upper surface of the housing.

14. The emulsion generating system of claim 13, wherein the displacement fluid port is disposed on the upper surface of the housing.

15. The emulsion generating system of claim 13, wherein the displacement fluid port is disposed on a lower surface of the housing, a passageway defined between the displacement fluid port and the sample tube through the first and second channel gaskets and the membrane.

16. The emulsion generating system of claim 11, wherein the first and second sets of channels are concurrently complementary.

17. The emulsion generating system of claim 11, wherein the first and second sets of channels are countercurrently complementary.

18. A method of generating an emulsion, the method comprising:

applying an aqueous sample solution to a sample tube of an emulsion generating system comprising:

an emulsion generating device comprising:

a housing defining a sample inlet port, a carrier fluid inlet port, an emulsion outlet port, and a displacement fluid inlet port;

a first gasket including a first set of channels;

a second gasket including a second set of channels complementary to the first set of channels, a carrier fluid inlet and the emulsion outlet port fluidically coupled to the second set of channels; and a membrane disposed between the first and second gaskets, wherein the first set of channels includes at least two channels each having at least two portions and the second set of channels includes at least three channels each having at least two portions, and wherein the first gasket and the second gasket are aligned such that each channel in the first set of channels has one portion overlapping one of the channels in the second set of channels and another portion overlapping a different one of the channels in the second set of channels; and a sample tube disposed on the sample inlet port and in fluidic communication with the displacement fluid inlet port, applying a displacement fluid through the displacement fluid inlet port;

applying a carrier fluid through the carrier fluid inlet port; and collecting an emulsion through the emulsion outlet port.

19. The method of claim 18, wherein the displacement fluid and the carrier fluid comprise an oil.

20. The method of claim 18, wherein the displacement fluid displaces the aqueous sample fluid from the sample tube.

* * * * *